US010041079B2

(12) United States Patent
Moellering et al.

(10) Patent No.: US 10,041,079 B2
(45) Date of Patent: Aug. 7, 2018

(54) COMPOSITIONS AND METHODS FOR EXPRESSING GENES IN ALGAE

(71) Applicant: Synthetic Genomics, Inc., La Jolla, CA (US)

(72) Inventors: Eric R. Moellering, San Diego, CA (US); Amanda R. Edwards, Carmichael, CA (US); Nicholas Bauman, San Diego, CA (US)

(73) Assignee: Synthetic Genomics, Inc., La Jolla, CA (US)

( * ) Notice: Subject to any disclaimer, the term of this patent is extended or adjusted under 35 U.S.C. 154(b) by 0 days.

(21) Appl. No.: 15/365,844

(22) Filed: Nov. 30, 2016

(65) Prior Publication Data

US 2017/0152520 A1 Jun. 1, 2017

Related U.S. Application Data

(60) Provisional application No. 62/323,480, filed on Apr. 15, 2016, provisional application No. 62/261,777, filed on Dec. 1, 2015, provisional application No. 62/261,217, filed on Nov. 30, 2015.

(51) Int. Cl.
*C12N 15/82* (2006.01)
*C07K 14/405* (2006.01)
*C12N 15/79* (2006.01)

(52) U.S. Cl.
CPC ........ *C12N 15/8216* (2013.01); *C07K 14/405* (2013.01); *C12N 15/79* (2013.01); *C12N 15/8209* (2013.01); *C12N 15/8218* (2013.01); *C12N 15/8247* (2013.01); *C12N 15/8269* (2013.01)

(58) Field of Classification Search
CPC . C07H 21/04; C12Q 1/68; C12M 1/34; G06F 19/20; C12N 9/22; C12N 15/113
USPC ......... 435/320.1, 375, 6.14, 287.2; 536/24.3, 536/24.5
See application file for complete search history.

(56) References Cited

U.S. PATENT DOCUMENTS

2006/0281107 A1 12/2006 Davis et al.
2006/0292572 A1 12/2006 Stuart et al.
2014/0142160 A1 5/2014 Lee et al.
2014/0186919 A1 7/2014 Zhang et al.

FOREIGN PATENT DOCUMENTS

WO WO 2016/109840 A2 7/2016

OTHER PUBLICATIONS

EH636437, GenBank Accession No. EH636437, "EST7545 LKO4 *Laupala kohalensis* cDNA clone 1061021797615 5-, mRNA sequence", May 17, 2007 [online]. [Retrieved on Mar. 21, 2017] Retrieved from the Internet: https://www.ncbi.nlm.nih.gov/nucest/EH636437> entire document.
International Search Report dated Apr. 5, 2017, regarding PCT/US2016/064275.

*Primary Examiner* — Jana A Hines
(74) *Attorney, Agent, or Firm* — DLA Piper LLP (US)

(57) ABSTRACT

The present application provides novel regulatory elements including promoter sequences from microorganisms. The application further discloses DNA constructs containing these novel regulatory elements, and recombinant microorganisms comprising these regulatory elements. Methods of modifying, producing, and using the regulatory elements are also disclosed. The regulatory elements and transformation methods disclosed herein are particularly suited for use in *Parachlorella* and other microalgae.

20 Claims, 10 Drawing Sheets pSGE6450

SEQUENCE LISTING

<160> NUMBER OF SEQ ID NOS: 51

<210> SEQ ID NO 1
<211> LENGTH: 530

```
<212> TYPE: DNA
<213> ORGANISM: Parachlorella sp.
<220> FEATURE:
<221> NAME/KEY: misc_feature
<223> OTHER INFORMATION: RPS4 promoter

<400> SEQUENCE: 1
ccaccatggg ggaggtttga agtgtgcgcc tgatataatc atacacctaa aagcaccact      60
tgctgattgt gaagggacta tgtcgtttat gacgggacgt tacgctggcc gatggtttga     120
atttggacgc tgtggtagaa tgttatatgg acgtaaaggt tggcatattg aaaatcgtct     180
tcgcaggcaa acttctagac gtgtgaccca ccggtaaaac gacaagcgtg gcgcgtcgat     240
tgcgctttga acgtcgtttg ttggactcca gatgaacctc aaaatcaaag cggtgattga     300
cgaaaatcaa atgacagccc gcaaaatttc atcagccttc ggatcggatt ctcagaatct     360
gattgtccct gctggctaca tttatgaaat ttcgtacatt ttggcagaaa tgtcccaata     420
ccatagcact gccgcctgag ctcacccgag caatgcatac tgggtacctc gcccatctcg     480 ccctcttttcc aagcccagtg ctgttgtaat agccaaaggg ctcagtaaca                530

<210> SEQ ID NO 2
<211> LENGTH: 375
<212> TYPE: DNA
<213> ORGANISM: Artificial Sequence
<220> FEATURE:
<223> OTHER INFORMATION: Synthetic
<220> FEATURE:
<221> NAME/KEY: misc_feature
<223> OTHER INFORMATION: Bleomycin resistance gene, codon-optimized for
      Parachlorella

<400> SEQUENCE: 2
atggccaaac tgcatccgc tgttcctgtg ttgacagcaa gagatgttgc aggtgcagtg       60
gagttttgga cagatagact ggggtttagc agggactttg tggaggacga ttttgcagga    120
gtggtgaggg atgatgtgac actgtttatc tcagccagtgc aggatcaagt ggtgcccgat    180
aatacactgg catgggtttg ggtgagagga ttggatgaac tgtatgcaga gtggtctgaa    240
gtggtgagca ccaactttag ggatgcaagc ggacctgcaa tgacagagat tggagaacaa    300
ccttggggaa gggagtttgc attgagagat cctgcaggga attgcgtgca ctttgttgca    360
gaagaacagg actga                                                      375

<210> SEQ ID NO 3
<211> LENGTH: 111
<212> TYPE: DNA
<213> ORGANISM: Nannochloropsis gaditana
<220> FEATURE:
<221> NAME/KEY: misc_feature
<223> OTHER INFORMATION: T4 terminator

<400> SEQUENCE: 3
tggatgacct tttgaatgac ctttaataga ttatattact aattaattgg ggaccctaga      60
ggtccccttt tttatttaa aaatttttc acaaaacggt ttacaagcat a                111

<210> SEQ ID NO 4
<211> LENGTH: 1000
<212> TYPE: DNA
<213> ORGANISM: Parachlorella sp.
<220> FEATURE:
<221> NAME/KEY: misc_feature
<223> OTHER INFORMATION: PsbR promoter

<400> SEQUENCE: 4
```

```
aagttgagca aggatgtggt ttgctgtttt agtcggggcc acagccttct catagggatt      60 tgttttgtg ctgggtactg tgacaattca tgtccttgtt cgcccgcatc tctgtttctg      120
gcgacctgtg ttaggctggc agagtacctc aagaacagca gggtgatcgc ttttccact      180 ttttcaataa actagtgtgc aagctaagta ggtacttggc agccagcggt caaatggtga      240
gcagattcat catattctaa gaatctcagc aattcaaaca tgcgtatgaa tcaacaacac      300
acgacttatt gcttatgcca agctactgca gatttcgaac aaatactcgt ctctgcttga      360
acaagtactt ttactcttgc aaaaaaacca ttcatgtttc tgtgatcata accgtgtgca      420
ccccgacagt acagacgcag ttatagtgac gtagatctgc acaggtaaac gattatgaca      480
ggctgccttt gagacgtggg tggatcacaa agttgtgtc ttgcggtaga ttgatgctgt      540
caaaaaccaa aacttcaaag ccacaacgtt tgcaatgaat acctgataac aagccaacaa      600
tttgtgtctg accttgtgta catcgaaggt tcaaagagga cttcacagaa cttagtaaat      660
gaaactggcg tattgcctac agacaaggtt gtaagacaat cttcgggcgt cttttctcaa      720
gctaggatgt tcgataatga acaattaggg tttatattag attctagaag atattagaag      780
aaactgcaac cagccgcaga gggtttccgc tatatccgcc gttcaaagtt ttggcgcggt      840
gctattgtca ttccaccgca gtgtttgacc cggggacctc atccaatcgc tggcgtatcc      900
cactggcgcc agaaattctg aacaaacatg ctcactccgc agttgtgacc atctgttttc      960
ctgataaaac cagctgcgtt gtcattgtaa gcagatcata                          1000
```

<210> SEQ ID NO 5
<211> LENGTH: 702
<212> TYPE: DNA
<213> ORGANISM: Artificial Sequence
<220> FEATURE:
<223> OTHER INFORMATION: Synthetic
<220> FEATURE:
<221> NAME/KEY: misc_feature
<223> OTHER INFORMATION: TurboGFP coding sequence, codon-optimized for
      Parachlorella

<400> SEQUENCE: 5

```
atgttggaga gcgacgagag cggcctgccc gccatggaga tcgagtgccg catcaccggc      60
accctgaacg gcgtggagtt cgagctggtg ggcggcggag agggcacccc cgagcagggc     120
cgcatgacca acaagatgaa gagcaccaaa ggcgccctga ccttcagccc ctacctgctg     180
agccacgtga tgggctacgg cttctaccac ttcggcacct accccagcgg ctacgagaac     240
cccttcctgc acgccatcaa caacggcggc tacaccaaca cccgcatcga agtacgag      300 gacggcggcg tgctgcacgt gagcttcagc taccgctacg aggccggccg cgtgatcggc     360
gacttcaagg tgatgggcac cggcttcccc gaggacagcg tgatcttcac cgacaagatc     420
atccgcagca acgccaccgt ggagcacctg caccccatgg gcgataacga tctggatggc     480
agcttcaccc gcaccttcag cctgcgcgac ggcggctact acagctccgt ggtggacagc     540
cacatgcact tcaagagcgc catccacccc agcatcctgc agaacggggg ccccatgttc     600
gccttccgcc gcgtggagga ggatcacagc aacaccgagc tgggcatcgt ggagtaccag     660
cacgccttca gacccccgga tgcagatgcc ggtgaagaat aa                        702
```

<210> SEQ ID NO 6
<211> LENGTH: 200
<212> TYPE: DNA
<213> ORGANISM: Nannochloropsis gaditana
<220> FEATURE:

<221> NAME/KEY: misc_feature
<223> OTHER INFORMATION: T5 terminator

<400> SEQUENCE: 6

```
gggtgggaag gagtcgggga gggtcctggc agagcggcgt cctcatgatg tgttggagac      60
ctggagagtc gagagcttcc tcgtcacctg attgtcatgt gtgtataggt taaggggggcc    120
cactcaaagc cataaagacg aacacaaaca ctaatctcaa caaagtctac tagcatgccg    180
tctgtccatc tttatttcct                                                200
```

<210> SEQ ID NO 7
<211> LENGTH: 546
<212> TYPE: DNA
<213> ORGANISM: Parachlorella sp.
<220> FEATURE:
<221> NAME/KEY: misc_feature
<223> OTHER INFORMATION: RSP4 Terminator

<400> SEQUENCE: 7

```
gcatagcatc agcctgtggc agggttgtgg tagggctgag tggcagggtt aaaggggttg      60
cctaccccac ccctactctc atgacaccag caacagcagc agctcatgca gtactcaaat    120
cactgatgtc aatggtgtga cacatttggt taaggctgct ttttaaagtg ctgctttggg    180
ggcagtgact gtgcagagct tggagcgtat ccccatgtaa tcagaaccga cgagagttcg    240
gggcaaccct tcatcttcac attttttgtg atcagctaca gagtctgaaa tcaaatagag    300
gctgccatct aaacgcagga gtcacaacga aggcgaaaac tccaattgct gtactcaatg    360
cactaagtga ttgttcaatg gataaataca ctatgctcaa ttcatgccag cagagctgct    420
ccttccagcc agctacaatg gcttttccca cgccttttga agtatgaatg ttcagcttgc    480
tgtgcttgat gcatcaccat aaacacaatt ctacaacatt tcatgccaac aacagtacgg    540
gctttc                                                               546
```

<210> SEQ ID NO 8
<211> LENGTH: 572
<212> TYPE: DNA
<213> ORGANISM: Parachlorella sp.
<220> FEATURE:
<221> NAME/KEY: misc_feature
<223> OTHER INFORMATION: ACP1 Promoter

<400> SEQUENCE: 8

```
agtttgcata gttaagtatg ctggctattg cagtaccctta tatgcaaaca agtgctcaat     60
ctgtttcatc attgtctgtg ggcaaattgc ctgccaatat tctccagtta ttgcctgttg    120
tttcaaatga ttgaaattgg aagttgtatt gctctacatt tttgacttgt gatttttca    180
tttgttgata tctgacaact gtgaactgca ctgaacttgc tgtgcttata aatgcatttt    240
tttgtttggg ccacgttga ttccttgtga tactttcctg ctatcaaacc aaaaatatac    300
tctcatgact gacgtgcaac aaatgcatgg aagctttcaa cgttacgaca gctgcttgcc    360
ccccatcagc tattctacat gtgtaaccta ccttgcatgg ccaccacaac gctactgcat    420
gcaagatctg gcgcaactgg atgtcccaat agtagaagta tccggattat ctccgagagt    480
tttacatatg taatcgacgc catttctgtc atcaactata aatccattgc tcctgcattt    540
ctggcactga cattctacca caagcaatac ca                                  572
```

<210> SEQ ID NO 9
<211> LENGTH: 869
<212> TYPE: DNA

<213> ORGANISM: Parachlorella sp.
<220> FEATURE:
<221> NAME/KEY: misc_feature
<223> OTHER INFORMATION: ACP1 Terminator

<400> SEQUENCE: 9

| | | | | | | |
|---|---|---|---|---|---|---|
| gcagcagctt | gttatgcctt | ccccatgggc | atcagcatgc | tgcaagctgt | ctagatatcc | 60 |
| agctttcagt | ggaggttgag | cgagggtcag | cagcggttcc | ctggcgatgg | cggtcagctt | 120 |
| ttctggaagc | cttcactagg | actgcgccca | gcgcatgtga | cgccaatcga | acttgtgtgc | 180 |
| aaggccaaat | tttgtgaccc | tgtgctgcac | ttcatgtatt | caagaattga | aagaaattt | 240 |
| cattgctgcc | cttctttcac | tttaatttcc | atccctggat | ccacctccca | ccattgtggt | 300 |
| tgatgggtag | gggttttggg | taggtgcagt | tcgttgtgca | cgttgacatg | tgtaacggtg | 360 |
| agcaaaggaa | ttgctgggca | agtagctatt | gcagcttaag | gcatggtga | aacacttgtg | 420 |
| ctgtatttac | agaggaagcc | agacaggtaa | ggagtgtgtg | gcagcttgga | acaggagggc | 480 |
| tggtcgcaac | aagtatgcat | atcccatgat | tgttgacata | agagcagcag | gtgcatattg | 540 |
| ccagcctttg | tgaaagtgga | ttgaaaatcg | attagttggt | gtgatagctg | aggctaggca | 600 |
| ctgccaacct | gcagtgaaat | gaggctccaa | gaccgggtaa | taatacaggc | aatcgaatcc | 660 |
| agttgaaatt | acggcgatta | aatccaagcg | agcgttgtaa | gaacatctgc | acctgtctga | 720 |
| agtagtgagc | ggataatgag | cattgcttgc | cttctatcac | tatacctgac | agttacgtgt | 780 |
| cacacactct | caagcacaac | acacagcggc | aaagttactt | gctaaacctc | acagtcaagc | 840 |
| tgaaaataaa | ggctaaatta | cgtgagacc | | | | 869 |

<210> SEQ ID NO 10
<211> LENGTH: 1707
<212> TYPE: DNA
<213> ORGANISM: Parachlorella sp.
<220> FEATURE:
<221> NAME/KEY: misc_feature
<223> OTHER INFORMATION: encodes cpSRP54

<400> SEQUENCE: 10

| | | | | | | |
|---|---|---|---|---|---|---|
| atgcttcggc | agcagctgtt | gcacagcggc | aggcagccgg | gtgcgacatg | cagcttacta | 60 |
| acctgctcga | catggcgacc | gtctgccttg | ttcggccgtc | ctaagcccca | aaaactgcac | 120 |
| agccagcgct | tgcagcatca | gggccgcccc | tcccgcctcg | tcgtgcgcag | cgcaatgttc | 180 |
| gacaacctga | gccgcagcct | ggagagggcg | tgggacatgg | tgcgcaagga | cgggcggcta | 240 |
| acggcggaca | acatcaagga | gcccatgcgg | gagattcgca | gggcgctgct | tgaggcggat | 300 |
| gtgaggctgg | gggcgccgct | gatcagattc | ttggtatcta | ccccccccc | ctcccaggtc | 360 |
| tccctccccg | tggtgcgcaa | gtttgtgaag | gcggtggagg | agaaggcgct | gggttctgca | 420 |
| gtgaccaagg | gtgtcacccc | cgaccagcag | ctggtgaagg | tggtgtacga | ccagctgcgg | 480 |
| gagctgatgg | gggggcagca | ggaagggctg | gtgcccactt | cgccagagga | gccgcaggtg | 540 |
| atcttgatgg | cggggctgca | gggcacgggg | aagacgacag | ctgcggggaa | gctggccttg | 600 |
| ttcctgcaga | agaaggggca | gaaggtgctg | ctggtggcca | ccgacatcta | ccgccccgcc | 660 |
| gccatcgacc | agctggtgaa | gctgggcgac | aggataggg | tgccggtgtt | ccagctggga | 720 |
| acccaggtgc | agccgccgga | gattgcaagg | caggggctgg | agaaggcgcg | agcagagggg | 780 |
| tttgacgccg | tcatcgtcga | cacggcgggg | cggctgcaga | tcgaccagag | catgatggag | 840 |
| gagctggtgc | agatcaagtc | cacggtgaag | ccctccgaca | cgctgctagt | ggtcgatgcg | 900 |
| atgacggggc | aggaggcagc | cgggctggtg | aaggcgttca | atgatgccgt | ggacatcaca | 960 |

| | | |
|---|---|---|
| ggcgccgtgc tgaccaagct tgacggggac agccgcggcg gcgccgcgct gagcgtgcgc | 1020 | |
| caggtcagcg gcggcccat caagtttgtg ggcatggggg agggcatgga ggcgctggag | 1080 | |
| cccttctacc ccgagcgcat ggccagcagg attctgggca tgggtgacgt ggtcaccctg | 1140 | |
| gtggagaagg ctgaggagag catcaaggaa gaggaggcgc aggagatatc gcggaagatg | 1200 | |
| ctgtcggcca aatttgactt tgacgacttc ctgaagcagt acaagatggt ggcggggatg | 1260 | |
| gggaacatgg cccaaatcat gaagatgctg ccaggcatga acaagtttac ggagaagcag | 1320 | |
| ctggcgggcg ttgagaagca gtacaaggtg tacgagagca tgatccagag catgacggtg | 1380 | |
| aaggagcgca agcagccgga gctgttggtg aagtcgccct ccaggaggcg cgcatagcg | 1440 | |
| cgcgggtcgg ggcgctcgga gcgggaggtc acagagctgc tgggggtgtt caccaacctg | 1500 | |
| cggacgcaga tgcagagctt ctccaaaatg atggccatgg gggggatggg catgggctcc | 1560 | |
| atgatgagcg acgaggagat gatgcaggcc acgctggcag gcgccggccc ccgccccgtg | 1620 | |
| ccagctggca aggtgcggcg gaagaagctg gccgcggcgg gcgggtcgcg gggcatggct | 1680 | |
| gagctggcat ccctgaaggc agaatga | 1707 | |

<210> SEQ ID NO 11
<211> LENGTH: 1044
<212> TYPE: DNA
<213> ORGANISM: Parachlorella sp.
<220> FEATURE:
<221> NAME/KEY: misc_feature
<223> OTHER INFORMATION: OCP-A Promoter

<400> SEQUENCE: 11

| | | |
|---|---|---|
| tgtgcatgta gatggcaagt taaagaagtg gtatacctgc aagtcatgtg tgcaacgtat | 60 | |
| agagggtgtc atcccctcat gatcaacatg cgcggtaagg ttgcaaatca gacgggaggc | 120 | |
| tgttactggt atgcaacgtt tcatcaaacc ataagatgtg tggggtgaaa tgcatactgg | 180 | |
| ttttcagaat gatagtccag actggagtat ataacaatac acatcattgc attcaaatac | 240 | |
| aaatatgttt atggtgagta tgcccgtgca cgagtgtcag agttacgctg ggactgaatt | 300 | |
| tatcacacag cgcagcagtg ccctcccatc accggaagtc atttcatata ataccatat | 360 | |
| acctatgtca acccgccaga accgtgtacg cactgttcca gatcatgcag ctgcttcaag | 420 | |
| catagatgaa tctttcagca tcaactgttg ttaggtgaag accagctacc tacttcgcac | 480 | |
| gcacaaaaat tgcacctgca ttcctgtgtc atctaaatct ctcctattga tgcctggtag | 540 | |
| ctctgaattg attggaaact catactgtgt aatctaatat gtctgaaaca agatgaatc | 600 | |
| cacttgtttg aagcaaacag gaccgctgtg ctgtgcattg cacgtgagga ttgggtgtga | 660 | |
| tcactttcat caaatcacgt tttttgtttt gcttgcagct tcacatcttt tccctgcta | 720 | |
| accacacacc cggaacaaaa acaaagccgt tatgtttgta tactccaaag cacggtcagt | 780 | |
| cgtgatgctt taaggacaat aagtgcatat aatttgcaac aatagaaatt atgcatgtta | 840 | |
| cagttgtatc gccctgtgtt cctcccatga cagccttgca aaaacttccc aatcgtgtgg | 900 | |
| cagctgatga ggtggccagc tgctttgcat gcttcgcccg aggtttcact gaggatgata | 960 | |
| cacagaaatt caggagaatg acacattgtt gattccaact ggctccctca acatcgtatc | 1020 | |
| gtcagttcca ttggtacccg ccat | 1044 | |

<210> SEQ ID NO 12
<211> LENGTH: 598
<212> TYPE: DNA
<213> ORGANISM: Parachlorella sp.

<220> FEATURE:
<221> NAME/KEY: misc_feature
<223> OTHER INFORMATION: OCP-A Terminator

<400> SEQUENCE: 12

| | | | | | |
|---|---|---|---|---|---|
| ggaggaggac | ctggtccccc | tgctcgaaaa | gcaggatttg | ggcgggaggg | tgcagggtct | 60 |
| gcagctaacc | ggcagggccc | tgcgcatctc | agggtctcag | ctcagctccc | gcacagggtg | 120 |
| cagtgcagtg | agatcagggc | tgctggcccc | gactgcagac | gtgtgtacgg | ctgcgtgcgt | 180 |
| aaccctgcgt | catgcggcac | agcattgcat | ggctcccagt | aggggacagc | tgctgtgagt | 240 |
| ggagcccccc | cccccctcca | catcttgttg | aggaacgcgc | cgggatggtt | gcatgcagcc | 300 |
| aggggtggca | taaataggcc | ttgattgttc | ggctgccgat | atgtactgcc | atgtaaggtt | 360 |
| gccgggccac | ccagctgccc | aggtccagca | gggtgaagtg | ggatggcaat | cacgcagctc | 420 |
| gttcatgtca | tctcaagttt | aagactcgac | ctcgttttgt | ctgcggctgg | gtgaatgagc | 480 |
| acccaatgca | cctcttgctg | gagctgggcc | cccttgggag | ctagctggca | gctgcaggcc | 540 |
| tagcacgctg | tgggagggat | gacttacact | ttgggaaagt | aagaaaaaaa | ataaagat | 598 |

<210> SEQ ID NO 13
<211> LENGTH: 832
<212> TYPE: DNA
<213> ORGANISM: Parachlorella sp.
<220> FEATURE:
<221> NAME/KEY: misc_feature
<223> OTHER INFORMATION: FBPase Promoter

<400> SEQUENCE: 13

| | | | | | |
|---|---|---|---|---|---|
| ttggtgtttt | taaggtgctc | atccggtgaa | gatgaatggg | gtggttgagt | tagtgcaggc | 60 |
| acgctggtgt | gcagtaccca | gtgtatggat | ggaagtttgg | gggcctgata | tgtgtgctcc | 120 |
| cgcctttttg | gtcgtttctt | gcttcaaacc | agtggcggat | gccagttttt | cgtccacagg | 180 |
| ccaattcgtt | attttgcagt | tctatttaat | tggaaaggtt | caaatgtatc | atttgtgtaa | 240 |
| tatcacatga | catctctgtc | acgaagcaga | atgaaattaa | ctaatgatca | ttattcgcac | 300 |
| atatgtactc | caccataagt | accatggtgt | tgtgacgttg | gaatcagcag | caaggtcaaa | 360 |
| tcacatgtct | tttcctcttt | caccaacaca | ggtaggcaca | ccttcaaact | gttctgatat | 420 |
| atactgagga | cgtacattaa | gtcgttaata | cacgacgcga | aatgatcaga | ggcagttcat | 480 |
| gctattgaca | gtctgaccac | agtctgatgc | acaccagaac | taccaaaatg | gcatctcgac | 540 |
| ggggtcacac | ggggtagcga | gcaatgcaaa | ctcgtaccgt | caataaagct | tgcaagcatt | 600 |
| ccagcaccga | atcttgacgg | gcgggtaccc | ttcgtcagga | acaaccgtc | attcaatatc | 660 |
| ggctgtttca | ttctggcgtt | cccgccaagg | accctaagcc | ctaatcacag | ctttatcccc | 720 |
| gttcgcaaag | cctgcatcag | ccgttgagta | tttgtgttca | gcccactgac | aactaagtcc | 780 |
| tccacaactt | ctgcttgatt | ctgtttggtt | gctctgaaac | acatacacaa | cc | 832 |

<210> SEQ ID NO 14
<211> LENGTH: 703
<212> TYPE: DNA
<213> ORGANISM: Parachlorella sp.
<220> FEATURE:
<221> NAME/KEY: misc_feature
<223> OTHER INFORMATION: FBPase Terminator

<400> SEQUENCE: 14

| | | | | | |
|---|---|---|---|---|---|
| gcgctctgtg | actaatccgt | tgacctattt | agtcattgca | tgattagtca | gtgcagcagg | 60 |
| ctgtgtccat | tgtcgcctcc | tgactgccag | agcctttgtt | tggtctttgc | cttaacattg | 120 |

```
tacacccttt gtcgtgcttt tcctgagaca gcatttaatt ttgttgggcg tggagcctgt      180
ggcttacgtg tcctctggtc cgtagttgct cggtgcaaca cggggggtatg ggtggcagag      240 gggctcagtc ccgctcttac ccttgcctgc tgctggccct gatcaatttg agatttattt      300
tcctcttttc gacactgagc ttgcatgact gctgagatgg cggtggtagt tgtctgcatg      360
taatgtgtgg cgttttttgg aagtggccct gccctgccac attggtgcta ccacaccttc      420
tttgatggct taatgggcag accctcctgc aggatcgccg aaacctctgc accgccagtc      480
tgtgtaatta aaattcgaga cgctgttaag tggaacactt tgctacagct gaaatgcgaa      540
gcgaatgcgc agtgatgctc aacttttgca actatgctga gctaggcgac tggtgtttaa      600
ttgcacctac tccctactac ggcctcagct catcacagca gataagaagt aagagcacaa      660
tgataatgcg cttaacaacc ccttagcact gcagcatctg tgg                        703
```

```
<210> SEQ ID NO 15
<211> LENGTH: 642
<212> TYPE: DNA
<213> ORGANISM: Parachlorella sp.
<220> FEATURE:
<221> NAME/KEY: misc_feature
<223> OTHER INFORMATION: EF2 Promoter

<400> SEQUENCE: 15
gaggactgac gattttgcac catgttagcc aagataagga tgttatgttt gcccagctcg       60
tgaagatttt tgatttccat gcacgtgaag caaagaatat gaataaactt gggctacagt      120
tgtcagcaca aacgcataac tttgctggta cacatcgttc gtagaaaaga tataaattat      180
tatagagcaa ttgtatttgg tgaaattttg tgtgtcttgt cgctgatgga actatcatca      240
cacgcgatgc ggagtgtaga aaacatcta tagattcgcg ctgaacctcc tcccaccttc      300
caatagctga tgagataaca gcatttgtga ttgcgacgga ttaaagtgtt gagtataaaa      360
aagttagagc atttttcatg cgatcaagtc tcccactcga gaactattac taactttact      420
caggcatgca ataatgtcat aatgttatat tgtcggcgca tctcccccgt ggccttgata      480
ggcaacgctg cgaccacaat ctctccttct ccctgctgtt cataacagcg attcattttc      540
aattcaagtg tgcagtccct gcgactcaca ctaattgcgg ctacctcgag ttgctgcatt      600
acctagcccc tgttggctgc tgtgtattga aactcagcaa cc                         642
```

```
<210> SEQ ID NO 16
<211> LENGTH: 668
<212> TYPE: DNA
<213> ORGANISM: Parachlorella sp.
<220> FEATURE:
<221> NAME/KEY: misc_feature
<223> OTHER INFORMATION: EF2 Terminator

<400> SEQUENCE: 16
gctacttgtt ggagacgtgg cggctgccag agtcaacagc agtgacagca gcattgctgg       60
gagacttgtg cgctattgcc gcccgacagt tgcagcagtg ggctacagcg cagatgctgt      120
gctacacggt ttatagagtt ccttttttgat tttgtggaag agcgcttttg ctgtcagctg      180
gcctgaagta cggggagcta tgggagtgca ccagggcgac ggtgcatcac ctatggagca      240
gccatgtaga gtagcattgc tgcatttacc catgggcagc tgcgttgtgg atgaattcat      300
tttccttgaa tgccttgccc tggttataag taataaaatt caattggcca taggtcgagg      360
aaagaagttg cacgtaccaa acgcagcttt tttggcaaat tgcctgccct gagcactgtg      420
```

```
tgtttttcgc tctggagacc gaggccatca gaacttttac cgcagctggc aatagcaggc    480
gatttcaatg ctctggcagt gttgctcgag gataaggtac aatctactgc aaagaaacgg    540
tcgtgcccaa tatgtacacg cgccctaccc tcactgcaac gcacgatagg cagagtatat    600
caaccactca ctggtatact gttgttcaca ggcaacatat catttcaacg tatgcaaagc    660
cattgaac                                                             668
```

<210> SEQ ID NO 17
<211> LENGTH: 588
<212> TYPE: DNA
<213> ORGANISM: Parachlorella sp.
<220> FEATURE:
<221> NAME/KEY: misc_feature
<223> OTHER INFORMATION: RPS17 Promoter

<400> SEQUENCE: 17

```
caacacctag ttggtaaata ccgttgctga tattgctctg taccagtaaa agagggctgc     60
gatgagcgtt tttagtgcac ttcttcaaca cggaatattt ttcacaaatt ggtatgagaa    120
ccaattttgc aaaatgttcg ccctgtaaag tatcgctctg gacgatcag cttgacgtaa    180 ttgtaggcga aaagggcgtt caaagtgcag ctttatgtat aacgtcata aaatataaag    240 catagcacaa tcactgatag aaaatatttg tgcgcattaa aactctcact tctgttgcgg    300
atacaacgac ggaaatgaga agcttgtgta agaagcaatt caagttttca ttttgtcatc    360
taaggtgtga tcctccgata ttcattaccg aatgctgatc tgagttggaa agatggcaat    420
atttagctgt gcacactttg acctccaggc cttggcggga atttagtatt ctagcttttcc    480 tattggaacg ataggccagc caagtctcca gcttgtatac gctacaccag cagacatgct    540
ctcaatttag ctgacagtgt cttcatattt gtattatctg ttgtgtct                 588
```

<210> SEQ ID NO 18
<211> LENGTH: 455
<212> TYPE: DNA
<213> ORGANISM: Parachlorella sp.
<220> FEATURE:
<221> NAME/KEY: misc_feature
<223> OTHER INFORMATION: RSPS17 Terminator

<400> SEQUENCE: 18

```
ggtgcgaata gtgcttcagt aaaaaagtag caacttggtg caatatcgtc agggtcgtgt     60
ggtctgctcg ccagcaagtt ttttggcaca ggagagcgct ttttccgagt accgccaaag    120
ttcaagcatg tgctgtgatt cgctgttgcc tcttatgata attgctcaaa gtttccaagc    180
attctatgtc caccctgcac cactaagttg tatggtgctt attctgcagg ggatgattca    240
tggtgcctaa aaattttgtg ctgctgtcgc gtctgttttc gtcgcagtt tagtgaatgt    300 aactccaaat accaaacttt tcatcacaat catattgatg cctttgtaag tgaattacag    360
cgttttttgc cataaaaaga agtaccgtga cattggggtc gtcataacaa gaagctttat    420
gaacaagcag cttgatctac gagacttata cataa                              455
```

<210> SEQ ID NO 19
<211> LENGTH: 707
<212> TYPE: DNA
<213> ORGANISM: Parachlorella sp.
<220> FEATURE:
<221> NAME/KEY: misc_feature
<223> OTHER INFORMATION: mitoATPSD Promoter

<400> SEQUENCE: 19

| cctgccagcc tcctgtgctt ttcagcctta tatcacacag gcaatgcga gcaggtgcag | 60 |
| tgggtgcaca cgatcatgca cttgttatgc gtgcacaagg aaatacaata acgggatgag | 120 |
| taaattcaga aagcggattc tgagtgtgga tcatctagat taattaggca tgctgcagtt | 180 |
| aatggattta tcaaaatgca gctagagggt agctgtgatt gggatgcaca gatgttgatg | 240 |
| acagtttatt gaagaaaatg gaaagcgtgc acatgaagat gatgaatgcg agtcaattgc | 300 |
| agatgatttg tctgtgtcag tctgtgatgc ttcttatcat ggtgtgcgct tctcatccag | 360 |
| ctgaaaatac atcagaatgt aatacttgta caatgcaagc gcaaacattc agcaacagtc | 420 |
| acggaaaggc aattgaatgg gcgatatctt cgttttggta aaatttgcat caaatccgct | 480 |
| ttggttatcc tcgatgaacg ccttgaagca tttaatccaa ctgtgctgta ctacatggga | 540 |
| acttgttgac ccagaggttg cttcccgcca ttcaaggccc ctaacaaatg ttaccaaacc | 600 |
| ctcactcttc tatccttcga ttggtccgca aattaccaag gaatcgaggt gtttggtaac | 660 |
| attcttagct ttactgctct aggttttgtg taggagactt aggcaac | 707 |

```
<210> SEQ ID NO 20
<211> LENGTH: 519
<212> TYPE: DNA
<213> ORGANISM: Parachlorella sp.
<220> FEATURE:
<221> NAME/KEY: misc_feature
<223> OTHER INFORMATION: mitoATPSD Terminator

<400> SEQUENCE: 20
```

| taggttcagt tgcgagaaca aaatacagtc cctgaacatt ttcggaacgg cgttttatgc | 60 |
| ggctttgttg ttccctagtg catgtggggg tttagaagac taggttttgt cactatcatt | 120 |
| gtgggcttga tgcccaccca tgcagcagac ctacaggact gcaggtgggt gaacctgttt | 180 |
| ctagaagttt tctggtcaat tgtaatgcca actagatgaa gagaacagaa gagttttctt | 240 |
| cattacatct gatggattat gctgaccatg cagccacacc aatgtggttt ctatgctgct | 300 |
| ttcagtcatg attagcattg caagcacgta ttctattcaa cacccaacca acgagatgaa | 360 |
| cataccaaat gtcaattgct tgcaaagcaa tcactcctgc acgagtgcca atttatcatg | 420 |
| atggcagtat ttatgcatgt acctttcaac aatatttttt ttcgcatacg aaaaatcgaa | 480 |
| cggaaatcta ccttgggcct atgtcaagtg acaggttcg | 519 |

```
<210> SEQ ID NO 21
<211> LENGTH: 874
<212> TYPE: DNA
<213> ORGANISM: Parachlorella sp.
<220> FEATURE:
<221> NAME/KEY: misc_feature
<223> OTHER INFORMATION: RBCS1 Promoter

<400> SEQUENCE: 21
```

| tggtcagaac ttcactcggc gttctgtctg gaaagggcta tgcagcgctc aattcatttt | 60 |
| tatcgactta aacgcaaata cgttcatcca gcagcaccag actcacgaga cgagtggtta | 120 |
| cggtgttggc aaaagtgcga ctgatataca aggagaatca gatgtaatat tcgtatctgg | 180 |
| attttatctg gtaactgtgc gcgagggtga gttgcgagga ttactgttcc ctgagtgtaa | 240 |
| caaattgata tttcccgttc tgcaaaccaa aaagggaata ctttggcaac tatttcacag | 300 |
| cctttcccgg gagatttcca tctgcaaatg aaaccggcat caccgcttgc gaagtacaga | 360 |
| actcgctgcg tgtgggcgac agcttcgaac ggccgcacta ttttggcaga gggagataag | 420 |
| ttgactgcga cacgtaacag gtgtacacat accaaattta acaaagaaaa cgttgtgaag | 480 |

```
gacagtcatt taaggtactg aagcaggaac ggataaactt cagtgaagat aataatgtag    540
aactatctgt gcgcaatgct cttctactgg gtttgttgaa tatagaacga acaagaaaag    600
agaaaaaagc aatcaggcgt agttcaatgc tgcaaaggtg tctcacaagg tagtccgacg    660
ccacccaagc aagatcgttg atgttggtgt tcatttgaaa gcgacccctc cccggggtcc    720
cagggaaata ctgttgcgcg ccaaatgtgg tagttatctt tctttctttt tgacacagag    780
ataatatgca tcgaaagcac cacaaaagtc cttctcggtc ttgcctgcaa gcttgtcctt    840
tgcgttgctc ctctcaaaaa aacttttgca cgca                                874

<210> SEQ ID NO 22
<211> LENGTH: 322
<212> TYPE: DNA
<213> ORGANISM: Parachlorella sp.
<220> FEATURE:
<221> NAME/KEY: misc_feature
<223> OTHER INFORMATION: RBCS1 Terminator

<400> SEQUENCE: 22
atgagtgccc atatgtaatt cgtagttgat gccatctgaa ggctattcga gaggaaaatc     60
cattttgatg tctttggttt gtaatattac tggtactgct tttcaggtag tatgtgctct    120
attgggacca ggttttttgtg atcgctgaat tgcgctgctc agcctggcgt gatggttttc    180
atctgctgtt ccttgtggat tgctatttttg ttgccatgag ttccttctag tgcacaagcc    240
cactgtaaag cgctcgcccc agtcaattat cgatcaatgt caagtgcagt tatcacatga    300
gttaattatt ggttcgtcaa ag                                             322

<210> SEQ ID NO 23
<211> LENGTH: 874
<212> TYPE: DNA
<213> ORGANISM: Parachlorella sp.
<220> FEATURE:
<221> NAME/KEY: misc_feature
<223> OTHER INFORMATION: RBCS2 Promoter

<400> SEQUENCE: 23
gaaagcttag cgatacagta ttttcttgtg aagcagaaga agggcaagtg aggtcgttgc     60
ataatgttgt acaccgttgc aattgcatag taaatcagtt tctcaacaga gacatcagtt    120
gggcaattcc atgaaatgca tgttgcaggc caatcatttg cactgtacaa tttgggttgc    180
tcgagaattt gagagtgtac atcagctcga ctgaaagccg ctcaattttg tgcagagaag    240
caatcatcag gtggtaaata ttgaagtgtc gttctctgca agcccattg aaattacaca     300 ttgacgctgc gacaaagtca ggacaacgtc cgatttgtga tccttgacga ataactaaga    360
ctatttatca agcacgcagg tctgcacttg agcgtaggca acaaccgctc catactgggt    420
agcaggaaac ggcccacagc ggaagcaacc cccgtggcat tctagtatta ttgaatatgc    480
agcctgtaac aagacaaagt aggagccaca tgcttggatg taaacacatg catgtttgtt    540
aaataagcaa gcttaagttg ccaagcactc tgcttgacag cttgaaatta agatgcccac    600
caagtgcaac aatctgcgtg ttctttgagg cagtgtcctg atgtattgca agtaccacaa    660
tgggttgatg cattatcgtg gcactcttgc aagcgcatat cagcgtgcat tgggtgcgct    720
aactggccat cggcgcgggt aattttacgc gcgtcacgtg ctgtggatat aggagtattc    780
tgactttctt caaacagtgc ttatcagaac gctttgcggc tgtgtgcatc agttcacacc    840
ttcttggcaa aattctctgc acattgttga cgca                                874
```

-continued

<210> SEQ ID NO 24
<211> LENGTH: 510
<212> TYPE: DNA
<213> ORGANISM: Parachlorella sp.
<220> FEATURE:
<221> NAME/KEY: misc_feature
<223> OTHER INFORMATION: RBCS2 Terminator

<400> SEQUENCE: 24

```
actttcacac ttcacagaag ctcttacttc aatgccaggg agcatagctc gagaagataa      60
attgatgtgg ctgtgactgt cgggcagttg aactgtgaat gtacgtgctg tagttttgt      120 tctcattcgt gggtgggtga ttgtctgcct acttttcctg ttcccttcat tcccatttct     180
tgcctgtact cgtggcgcag ctcaccaatt aatttgagca tcgctggtca tctaccacct     240
gattgcgaac atttgctcaa ttctactgtt ccctggtgcg tggtctgcaa taattagctg     300
gggcgagcgc ttgcagttcc actgactgtg ggttatggtt tgttttaaac aaattttgtt    360 ttactaatttt cttgtagtgc gttggtcgtt gccatttgca gcattgaaaa gtcaggaagc    420
agacaatcta cccacccatc caatgtaggc gaaaatccag cagtagtccg ctgtatacaa     480
aaaccgatca ctcagcagcc cccccgatga                                      510
```

<210> SEQ ID NO 25
<211> LENGTH: 156
<212> TYPE: DNA
<213> ORGANISM: Parachlorella sp.
<220> FEATURE:
<221> NAME/KEY: misc_feature
<223> OTHER INFORMATION: RPS4 Intron 1

<400> SEQUENCE: 25

```
gtgagttctg agaagctgat tgttgtttaa cttctttgaa agctttatcg aagattctgc      60
aagcgatgaa cattgcttgt caagaccgag agctgcatgc ccacttgaca tccagctttg     120
aacggctctt catgtttgat ttgtttctga ttgtag                                156
```

<210> SEQ ID NO 26
<211> LENGTH: 292
<212> TYPE: DNA
<213> ORGANISM: Parachlorella sp.
<220> FEATURE:
<221> NAME/KEY: misc_feature
<223> OTHER INFORMATION: RPS4 Intron 2

<400> SEQUENCE: 26

```
gtgagtgcag cgtcagctgt ggcagttgtt ggctttcgtc tcagtcagta gtttgctggg      60
attgattatg gagggcacag ttgcaatttt gagttgcacg ttgcgacaag cgtgttgaca     120
aagcgtggtc aagccggcca gtcttgccgg tggcgggtgg cttggtctaa cttccgctct     180
acagcaatcg tttttgttcat ggttacgggg ctggcgtgcc agaaagtcct ggtcagccac    240
cctcgcttca aagccgtagc ccaacaactt tgcgaatatg ttcgatttgc ag             292
```

<210> SEQ ID NO 27
<211> LENGTH: 1322
<212> TYPE: DNA
<213> ORGANISM: Parachlorella sp.
<220> FEATURE:
<221> NAME/KEY: misc_feature
<223> OTHER INFORMATION: RPS4 Intron 3

<400> SEQUENCE: 27

```
gtacagctct gcgtgcaaca ggttgcaaga tgcagcgcag gtcttccctg gtcaaacgat      60
```

| | |
|---|---|
| gtatgcagag ttgagaggca cttgagctgg gtgaatggcg tgggctcgta ggtagtgtgc | 120 |
| agggcaggaa gggcagccaa ttttggagtt gtggtccggt gtcgttgctt cgagccttat | 180 |
| taggactctt gctcatcaaa gcgttagttg tgaataagtt gatctgaaag gatgttatgt | 240 |
| acagcaagca gcagcagtta agagtctggg gagtagctgc acagggcgag gtgtcaagat | 300 |
| gggaagggtc ctgcctcctt atgtgttttt ccctgtaggg gaggaagcct cttatgggca | 360 |
| atggttgggc atattttcca gccagcccct ctttctatag gggccagggt gggcccagct | 420 |
| cgtcttggct tccaccacca ggagagtgag ggcattgaag gccataaat agtcctccca | 480 |
| tctacgtgca ccagagggtg tcgtctaggc tgtgcatgcc acgaggggaa ggagccaaga | 540 |
| atgagtgtat gggttgtttt catgtttagg ctgggataaa actgttttca attgcgcctg | 600 |
| ccgggtgaaa accacagcag catcagcaag cttggagaag gccagcccgc ccagcacagg | 660 |
| ctcacgttcc cactcaggcg gtcagtcggg cgggggtgtg agtcaggcag gcgagggtgt | 720 |
| ctgtgcctga catcagcacc tctgcttagc cactgcagcc cctggagcag ggtagggcgt | 780 |
| catttgcagc aatcacctgc tgcctcacac gtcgcagctt ggaatttcaa cgaccatcag | 840 |
| cgctggggtt gttgagggat catagcagat tttggtgcag cctggttgtc atgctctttg | 900 |
| tggaatggcc tctatgttcg agcaattcgt tggatgttga ggtgcttggg gacagagagt | 960 |
| cgaatgatgg gccagggtca aacatgcgag cgtttggctg agtcagcggt ttttgctggt | 1020 |
| cacttttttct tttgtttctt atttaggttt gatggatgtg ttttgtgctg ctgccctgaa | 1080 |
| gctgcagcag cgtgtctgcc ctgcgctact gcgggcacca aggctatgtg ctggtgcact | 1140 |
| cggctgcgct gcacctgtgc acctcgcact ccgtccagcc tccatgcagc acacgtactc | 1200 |
| acggtgtcct cctgacctgt cgtacgtat tccaaacttg ctcttttgct gccgctgctc | 1260 |
| tcgtacacaa ttgctgttga ttatcgatat ctaatcgagc gcctgctgac tgaactccgc | 1320 |
| ag | 1322 |

<210> SEQ ID NO 28
<211> LENGTH: 326
<212> TYPE: DNA
<213> ORGANISM: Parachlorella sp.
<220> FEATURE:
<221> NAME/KEY: misc_feature
<223> OTHER INFORMATION: RPS4 Intron 4

<400> SEQUENCE: 28

| | |
|---|---|
| gtgggtgggc tctgaaggag gaggagggag cgggtgatta aacagggcct gcatgaagag | 60 |
| gagcaggggc tgcgtggaca gcaggggggaa ggtgcagaag ggagggtcaa gcggggttca | 120 |
| ggtggctgtg ggtttctgca cgagcagtga aagaagctgt atccttccac ctgcttccac | 180 |
| tggcgaaagg ttgaaaacag gatgtcgcag ctggaaagat gttgcgctgt caagtgcaag | 240 |
| ccatggttga gggtatgcct gtgtgcatgt gcttcttaaa gttactcctg ttctatggtt | 300 |
| ctgggtgctt gttgtttgtg gtgcag | 326 |

<210> SEQ ID NO 29
<211> LENGTH: 196
<212> TYPE: DNA
<213> ORGANISM: Parachlorella sp.
<220> FEATURE:
<221> NAME/KEY: misc_feature
<223> OTHER INFORMATION: RPS4 Intron 5

<400> SEQUENCE: 29

| | |
|---|---:|
| gtgaggggc atgtaagcaa tggcaggcaa ttcaagaacg aatcattgct gcaaatgctg | 60 |
| ggatggtatg cagctgaggt atctattgcc ttgtattttg tctcgcattg catcggtggt | 120 |
| gcgttctgtg gcctgaggca cagttcttgc tgtttgataa gggttcgact gagttgtcgt | 180 |
| gtgtgctgtg ctgcag | 196 |

<210> SEQ ID NO 30
<211> LENGTH: 2667
<212> TYPE: DNA
<213> ORGANISM: Artificial Sequence
<220> FEATURE:
<223> OTHER INFORMATION: Synthetic
<220> FEATURE:
<221> NAME/KEY: misc_feature
<223> OTHER INFORMATION: Intronylated, codon-optimized BleR gene

<400> SEQUENCE: 30

| | |
|---|---:|
| atggccaaac tgacatccgc tgttcctgtg ttgacagcaa gagatgttgc aggtgcagtg | 60 |
| gagttttgtg agttctgaga agctgattgt tgtttaactt ctttgaaagc tttatcgaag | 120 |
| attctgcaag cgatgaacat tgcttgtcaa gaccgagagc tgcatgccca cttgacatcc | 180 |
| agctttgaac ggctcttcat gtttgatttg tttctgattg tagggacaga tagactgggg | 240 |
| tttagcaggg actttgtgga ggacgatttt gcaggagtgg tgagggatga tgtgacactg | 300 |
| tttatctcag cagtgcagga tcaagtgagt gcagcgtcag ctgtggcagt tgttggcttt | 360 |
| cgtctcagtc agtagtttgc tgggattgat tatggagggc acagttgcaa ttttgagttg | 420 |
| cacgttgcga caagcgtgtt gacaaagcgt ggtcaagccg ccagtcttg ccggtggcgg | 480 |
| gtggcttggt ctaacttccg ctctacagca atcgttttgt tcatggttac ggggctggcg | 540 |
| tgccagaaag tcctggtcag ccaccctcgc ttcaaagccg tagcccaaca actttgcgaa | 600 |
| tatgttcgat ttgcaggtgg tgcccgataa tacactggca tgggtttggg tgagaggtac | 660 |
| agctctgcgt gcaacaggtt gcaagatgca gcgcaggtct ccctggtca acgatgtat | 720 |
| gcagagttga gaggcacttg agctgggtga atggcgtggg ctcgtaggta gtgtgcaggg | 780 |
| caggaagggc agccaatttt ggagttgtgg tccggtgtcg ttgcttcgag ccttattagg | 840 |
| actcttgctc atcaaagcgt tagttgtgaa taagttgatc tgaaaggatg ttatgtacag | 900 |
| caagcagcag cagttaagag tctggggagt agctgcacag ggcgaggtgt caagatggga | 960 |
| agggtcctgc ctccttatgt gttttttccct gtaggggagg aagcctctta tgggcaatgg | 1020 |
| ttgggcatat tttccagcca gcccttcttt ctatagggc cagggtgggc ccagctcgtc | 1080 |
| ttggcttcca ccaccaggag agtgagggca ttgaagggcc ataaatagtc ctcccatcta | 1140 |
| cgtgcaccag agggtgtcgt ctaggctgtg catgccacga ggggaaggag ccaagaatga | 1200 |
| gtgtatgggt tgtttttcatg tttaggctgg ataaaactg ttttcaattg cgcctgccgg | 1260 |
| gtgaaaacca cagcagcatc agcaagcttg agaaggcca gcccgcccag cacaggctca | 1320 |
| cgttcccact caggcggtca gtcgggcggg ggtgtgagtc aggcaggcga gggtgtctgt | 1380 |
| gcctgacatc agcacctctg cttagccact gcagcccctg gagcagggta gggcgtcatt | 1440 |
| tgcagcaatc acctgctgcc tcacacgtcg cagcttggaa tttcaacgac catcagcgct | 1500 |
| ggggttgttg agggatcata gcagattttg gtgcagcctg gttgtcatgc tcttttgtgga | 1560 |
| atggcctcta tgttcgagca attcgttgga tgttgaggtg cttggggaca gagagtcgaa | 1620 |
| tgatgggcca gggtcaaaca tgcgagcgtt ggctgagtc agcggttttt gctggtcact | 1680 |
| ttttctttg tttcttattt aggtttgatg gatgtgtttt gtgctgctgc cctgaagctg | 1740 |

```
cagcagcgtg tctgccctgc gctactgcgg gcaccaaggc tatgtgctgg tgcactcggc    1800
tgcgctgcac ctgtgcacct cgcactccgt ccagcctcca tgcagcacac gtactcacgg    1860
tgtcctcctg acctgtcgta cgctattcca aacttgctct tttgctgccg ctgctctcgt    1920
acacaattgc tgttgattat cgatatctaa tcgagcgcct gctgactgaa ctccgcaggt    1980
ttggatgaac tgtatgcaga gtggtctgaa gtggtgagca ccaactttag gtgggtgggc    2040
tctgaaggag aggagggag cgggtgatta acaggcct gcatgaagag agcaggggc       2100 tgcatggaca gcaggggaa ggtgcagaag ggagggtcaa gcggggttca ggtggctgtg    2160
ggtttctgca cgagcagtga agaagctgt atccttccac ctgctttcac tggcgaaagg    2220
ttgaaaacag gatgtcgcag ctggaaagat gttgcgctgt caagtgcaag ccatggttga    2280
gggtatgcct gtgtgcatgt gcttcttaaa gttactcctg ttctatggtt ctgggtgctt    2340
gttgtttgtg gtgcagggat gcaagcggac ctgcaatgac agagattgga gaacaacctt    2400
ggggaaggga gtttgcattg agagatcctg caggtgaggg ggcatgtaag caatggcagg    2460
caattcaaga acgaatcatt gctgcaaatg ctgggatggt atgcagctga ggtatctatt    2520
gccttgtatt tgtctcgca ttgcatcggt ggtgcgttct gtggcctgag cacagttct     2580 tgctgtttga taagggttcg actgagttgt cgtgtgtgct gtgctgcagg caattgcgtg    2640
cactttgttg cagaagaaca ggactga                                       2667

<210> SEQ ID NO 31
<211> LENGTH: 71
<212> TYPE: DNA
<213> ORGANISM: Artificial Sequence
<220> FEATURE:
<223> OTHER INFORMATION: Synthetic
<220> FEATURE:
<221> NAME/KEY: misc_feature
<223> OTHER INFORMATION: plasmid cloning site

<400> SEQUENCE: 31
cctgcaggca gttggtacgg catattatgg tttaaacatc tatcctccag atcaccaggg    60
ccagtgaggc c                                                        71

<210> SEQ ID NO 32
<211> LENGTH: 399
<212> TYPE: DNA
<213> ORGANISM: Artificial Sequence
<220> FEATURE:
<223> OTHER INFORMATION: Synthetic
<220> FEATURE:
<221> NAME/KEY: misc_feature
<223> OTHER INFORMATION: Codon-optimized Bsd gene

<400> SEQUENCE: 32
atggcaaaac ctctctccca ggaagagtct accctgattg aaagggcaac agcaaccatc    60
aacagcattc ccattagcga ggactactct gttgcatctg cagcattgag ctctgatgga    120 aggatctttta caggagtgaa cgtgtaccac tttacaggag gaccttgtgc agaattggtg    180
gtgttaggta cagcagctgc agcagcagca ggaaatttga catgcattgt ggcaataggg    240
aacgagaata gggggatttt gtcaccttgc ggaagatgta gacaggtgtt gttggatctg    300
catcccggga ttaaggcaat cgtgaaggat tcagatgggc agcctacagc agtgggaatt    360
agagaactgc tgccttctgg gtatgtgtgg gaaggataa                          399

<210> SEQ ID NO 33
<211> LENGTH: 2691
```

<212> TYPE: DNA
<213> ORGANISM: Artificial Sequence
<220> FEATURE:
<223> OTHER INFORMATION: Synthetic
<220> FEATURE:
<221> NAME/KEY: misc_feature
<223> OTHER INFORMATION: Bsd gene, intronylated

<400> SEQUENCE: 33

| | | | | | |
|---|---|---|---|---|---|
| atggcaaaac | ctctctccca | ggaagagtct | accctgattg | aaagggcaac | agcaaccatc | 60 |
| aacagcattc | ccattagcga | ggactactct | gttgtgagtt | ctgagaagct | gattgttgtt | 120 |
| taacttcttt | gaaagcttta | tcgaagattc | tgcaagcgat | gaacattgct | tgtcaagacc | 180 |
| gagagctgca | tgcccacttg | acatccagct | ttgaacggct | cttcatgttt | gatttgtttc | 240 |
| tgattgtagg | catctgcagc | attgagctct | gatggaagga | tctttacagg | agtgagtgca | 300 |
| gcgtcagctg | tggcagttgt | tggctttcgt | ctcagtcagt | agtttgctgg | gattgattat | 360 |
| ggagggcaca | gttgcaattt | tgagttgcac | gttgcgacaa | gcgtgttgac | aaagcgtggt | 420 |
| caagccggcc | agtcttgccg | gtggcgggtg | gcttggtcta | acttccgctc | tacggcaatc | 480 |
| gttttgttca | tggttacggg | gctggcgtgc | cagaaagtcc | tggtcagcca | ccctcgcttc | 540 |
| aaagcctag | cccaacaact | ttgcgaatat | gttcgatttg | caggtgaacg | tgtaccactt | 600 |
| tacaggagga | ccttgtgcag | aattggtggt | gttaggtaca | gctctgcgtg | caacaggttg | 660 |
| caagatgcag | cgcaggtctt | ccctggtcaa | acgatgtatg | cagagttgag | aggcacttga | 720 |
| gctgggtgaa | tggcgtgggc | tcgtaggtag | tgtgcagggc | aggaagggca | gccaattttg | 780 |
| gagttgtggt | ccgtgtcgt | tgcttcgagc | cttattagga | ctcttgctca | tcaaagcgtt | 840 |
| agttgtgaat | aagttgatct | gaaaggatgt | tatgtacagc | aagcagcagc | agttaagagt | 900 |
| ctggggagta | gctgcacagg | gcgaggtgtc | aagatgggaa | gggtcctgcc | tccttatgtg | 960 |
| tttttccctg | tagggagga | agcctcttat | gggcaatggt | tgggcatatt | ttccagccag | 1020 |
| cccttctttc | tataggggcc | agggtgggcc | cagctcgtct | tggcttccac | caccaggaga | 1080 |
| gtgagggcat | tgaagggcca | taaatagtcc | tcccatctac | gtgcaccaga | gggtgtcgtc | 1140 |
| taggctgtgc | atgccacgag | gggaaggagc | caagaatgag | tgtatgggtt | gttttcatgt | 1200 |
| ttaggctggg | ataaaactgt | tttcaattgc | gcctgccggg | tgaaaaccac | agcagcatca | 1260 |
| gcaagcttgg | agaaggccag | cccgcccagc | acaggctcac | gttcccactc | aggcggtcag | 1320 |
| tcgggcgggg | gtgtgagtca | ggcaggcgag | ggtgtctgtg | cctgacatca | gcacctctgc | 1380 |
| ttagccactg | cagcccctgg | agcagggtag | ggcgtcattt | gcagcaatca | cctgctgcct | 1440 |
| cacacgtcgc | agcttggaat | tcaacgacc | atcagcgctg | gggttgttga | gggatcatag | 1500 |
| cagattttgg | tgcagcctgg | ttgtcatgct | ctttgtggaa | tggcctctat | gttcgagcaa | 1560 |
| ttcgttggat | gttgaggtgc | ttggggacag | agagtcgaat | gatgggccag | ggtcaaacat | 1620 |
| gcgagcgttt | ggctgagtca | gcggttttg | ctggtcactt | tttctttgt | ttcttattta | 1680 |
| ggtttgatgg | atgtgttttg | tgctgctgcc | ctgaagctgc | agcagcgtgt | ctgccctgcg | 1740 |
| ctactgcggg | caccaaggct | atgtgctggt | gcactcggct | gcgctgcacc | tgtgcacctc | 1800 |
| gcactccgtc | cagcctccat | gcagcacacg | tactcacggt | gtcctcctga | cctgtcgtac | 1860 |
| gctattccaa | acttgctctt | tgctgccgc | tgctctcgta | cacaattgct | gttgattatc | 1920 |
| gatatctaat | cgagcgcctg | ctgactgaac | tccgcaggta | cagcagctgc | agcagcagca | 1980 |
| ggaaatttga | catgcattgt | ggcaataggt | gggtgggctc | tgaaggagga | ggagggagcg | 2040 |
| ggtgattaaa | cagggcctgc | atgaagagga | gcaggggctg | cgtggacagc | aggggggaagg | 2100 |

```
tgcagaaggg agggtcaagc ggggttcagg tggctgtggg tttctgcacg agcagtgaaa    2160
gaagctgtat ccttccacct gcttccactg gcgaaaggtt gaaaacagga tgtcgcagct    2220
ggaaagatgt tgcgctgtca agtgcaagcc atggttgagg gtatgcctgt gtgcatgtgc    2280
ttcttaaagt tactcctgtt ctatggttct gggtgcttgt tgtttgtggt gcagggaacg    2340
agaatagggg gattttgtca ccttgcggaa gatgtagaca ggtgttgttg gatctgcatc    2400
ccgggattaa ggtgaggggg catgtaagca atggcaggca attcaagaac gaatcattgc    2460
tgcaaatgct gggatggtat gcagctgagg tatctattgc cttgtatttt gtctcgcatt    2520
gcatcggtgg tgcgttctgt ggcctgaggc acagttcttg ctgtttgata agggttcgac    2580
tgagttgtcg tgtgtgctgt gctgcaggca atcgtgaagg attcagatgg gcagcctaca    2640
gcagtgggaa ttagagaact gctgccttct gggtatgtgt gggaaggata a             2691
```

<210> SEQ ID NO 34
<211> LENGTH: 1385
<212> TYPE: PRT
<213> ORGANISM: Artificial Sequence
<220> FEATURE:
<223> OTHER INFORMATION: Synthetic
<220> FEATURE:
<221> NAME/KEY: misc_feature
<223> OTHER INFORMATION: Encodes S. pyogenes Cas9, codon-optimized for
      Parachlorella, with NLS and C terminal FLAG tag

<400> SEQUENCE: 34

```
Met Ala Pro Lys Lys Arg Lys Val Gly Asp Lys Lys Tyr Ser Ile
1               5                   10                  15

Gly Leu Asp Ile Gly Thr Asn Ser Val Gly Trp Ala Val Ile Thr Asp
            20                  25                  30

Glu Tyr Lys Val Pro Ser Lys Lys Phe Lys Val Leu Gly Asn Thr Asp
        35                  40                  45

Arg His Ser Ile Lys Lys Asn Leu Ile Gly Ala Leu Leu Phe Asp Ser
    50                  55                  60

Gly Glu Thr Ala Glu Ala Thr Arg Leu Lys Arg Thr Ala Arg Arg Arg
65                  70                  75                  80

Tyr Thr Arg Arg Lys Asn Arg Ile Cys Tyr Leu Gln Glu Ile Phe Ser
                85                  90                  95

Asn Glu Met Ala Lys Val Asp Asp Ser Phe Phe His Arg Leu Glu Glu
            100                 105                 110

Ser Phe Leu Val Glu Glu Asp Lys Lys His Glu Arg His Pro Ile Phe
        115                 120                 125

Gly Asn Ile Val Asp Glu Val Ala Tyr His Glu Lys Tyr Pro Thr Ile
    130                 135                 140

Tyr His Leu Arg Lys Lys Leu Val Asp Ser Thr Asp Lys Ala Asp Leu
145                 150                 155                 160

Arg Leu Ile Tyr Leu Ala Leu Ala His Met Ile Lys Phe Arg Gly His
                165                 170                 175

Phe Leu Ile Glu Gly Asp Leu Asn Pro Asp Asn Ser Asp Val Asp Lys
            180                 185                 190

Leu Phe Ile Gln Leu Val Gln Thr Tyr Asn Gln Leu Phe Glu Glu Asn
        195                 200                 205

Pro Ile Asn Ala Ser Gly Val Asp Ala Lys Ala Ile Leu Ser Ala Arg
    210                 215                 220

Leu Ser Lys Ser Arg Arg Leu Glu Asn Leu Ile Ala Gln Leu Pro Gly
225                 230                 235                 240
```

```
Glu Lys Lys Asn Gly Leu Phe Gly Asn Leu Ile Ala Leu Ser Leu Gly
                245                 250                 255

Leu Thr Pro Asn Phe Lys Ser Asn Phe Asp Leu Ala Glu Asp Ala Lys
                260                 265                 270

Leu Gln Leu Ser Lys Asp Thr Tyr Asp Asp Leu Asp Asn Leu Leu
                275                 280                 285

Ala Gln Ile Gly Asp Gln Tyr Ala Asp Leu Phe Leu Ala Ala Lys Asn
                290                 295                 300

Leu Ser Asp Ala Ile Leu Leu Ser Asp Ile Leu Arg Val Asn Thr Glu
305                     310                 315                 320

Ile Thr Lys Ala Pro Leu Ser Ala Ser Met Ile Lys Arg Tyr Asp Glu
                325                 330                 335

His His Gln Asp Leu Thr Leu Leu Lys Ala Leu Val Arg Gln Gln Leu
                340                 345                 350

Pro Glu Lys Tyr Lys Glu Ile Phe Phe Asp Gln Ser Lys Asn Gly Tyr
                355                 360                 365

Ala Gly Tyr Ile Asp Gly Gly Ala Ser Gln Glu Glu Phe Tyr Lys Phe
                370                 375                 380

Ile Lys Pro Ile Leu Glu Lys Met Asp Gly Thr Glu Glu Leu Leu Val
385                     390                 395                 400

Lys Leu Asn Arg Glu Asp Leu Leu Arg Lys Gln Arg Thr Phe Asp Asn
                405                 410                 415

Gly Ser Ile Pro His Gln Ile His Leu Gly Glu Leu His Ala Ile Leu
                420                 425                 430

Arg Arg Gln Glu Asp Phe Tyr Pro Phe Leu Lys Asp Asn Arg Glu Lys
                435                 440                 445

Ile Glu Lys Ile Leu Thr Phe Arg Ile Pro Tyr Tyr Val Gly Pro Leu
                450                 455                 460

Ala Arg Gly Asn Ser Arg Phe Ala Trp Met Thr Arg Lys Ser Glu Glu
465                     470                 475                 480

Thr Ile Thr Pro Trp Asn Phe Glu Glu Val Val Asp Lys Gly Ala Ser
                485                 490                 495

Ala Gln Ser Phe Ile Glu Arg Met Thr Asn Phe Asp Lys Asn Leu Pro
                500                 505                 510

Asn Glu Lys Val Leu Pro Lys His Ser Leu Leu Tyr Glu Tyr Phe Thr
                515                 520                 525

Val Tyr Asn Glu Leu Thr Lys Val Lys Tyr Val Thr Glu Gly Met Arg
                530                 535                 540

Lys Pro Ala Phe Leu Ser Gly Glu Gln Lys Lys Ala Ile Val Asp Leu
545                     550                 555                 560

Leu Phe Lys Thr Asn Arg Lys Val Thr Val Lys Gln Leu Lys Glu Asp
                565                 570                 575

Tyr Phe Lys Lys Ile Glu Cys Phe Asp Ser Val Glu Ile Ser Gly Val
                580                 585                 590

Glu Asp Arg Phe Asn Ala Ser Leu Gly Thr Tyr His Asp Leu Leu Lys
                595                 600                 605

Ile Ile Lys Asp Lys Asp Phe Leu Asp Asn Glu Glu Asn Glu Asp Ile
                610                 615                 620

Leu Glu Asp Ile Val Leu Thr Leu Thr Leu Phe Glu Asp Arg Glu Met
625                     630                 635                 640

Ile Glu Glu Arg Leu Lys Thr Tyr Ala His Leu Phe Asp Asp Lys Val
                645                 650                 655
```

```
Met Lys Gln Leu Lys Arg Arg Arg Tyr Thr Gly Trp Gly Arg Leu Ser
                660                 665                 670

Arg Lys Leu Ile Asn Gly Ile Arg Asp Lys Gln Ser Gly Lys Thr Ile
            675                 680                 685

Leu Asp Phe Leu Lys Ser Asp Gly Phe Ala Asn Arg Asn Phe Met Gln
        690                 695                 700

Leu Ile His Asp Asp Ser Leu Thr Phe Lys Glu Asp Ile Gln Lys Ala
705                 710                 715                 720

Gln Val Ser Gly Gln Gly Asp Ser Leu His Glu His Ile Ala Asn Leu
                725                 730                 735

Ala Gly Ser Pro Ala Ile Lys Lys Gly Ile Leu Gln Thr Val Lys Val
            740                 745                 750

Val Asp Glu Leu Val Lys Val Met Gly Arg His Lys Pro Glu Asn Ile
        755                 760                 765

Val Ile Glu Met Ala Arg Glu Asn Gln Thr Thr Gln Lys Gly Gln Lys
770                 775                 780

Asn Ser Arg Glu Arg Met Lys Arg Ile Glu Glu Gly Ile Lys Glu Leu
785                 790                 795                 800

Gly Ser Gln Ile Leu Lys Glu His Pro Val Glu Asn Thr Gln Leu Gln
                805                 810                 815

Asn Glu Lys Leu Tyr Leu Tyr Tyr Leu Gln Asn Gly Arg Asp Met Tyr
            820                 825                 830

Val Asp Gln Glu Leu Asp Ile Asn Arg Leu Ser Asp Tyr Asp Val Asp
        835                 840                 845

His Ile Val Pro Gln Ser Phe Leu Lys Asp Asp Ser Ile Asp Asn Lys
850                 855                 860

Val Leu Thr Arg Ser Asp Lys Asn Arg Gly Lys Ser Asp Asn Val Pro
865                 870                 875                 880

Ser Glu Glu Val Val Lys Lys Met Lys Asn Tyr Trp Arg Gln Leu Leu
                885                 890                 895

Asn Ala Lys Leu Ile Thr Gln Arg Lys Phe Asp Asn Leu Thr Lys Ala
            900                 905                 910

Glu Arg Gly Gly Leu Ser Glu Leu Asp Lys Ala Gly Phe Ile Lys Arg
        915                 920                 925

Gln Leu Val Glu Thr Arg Gln Ile Thr Lys His Val Ala Gln Ile Leu
930                 935                 940

Asp Ser Arg Met Asn Thr Lys Tyr Asp Glu Asn Asp Lys Leu Ile Arg
945                 950                 955                 960

Glu Val Lys Val Ile Thr Leu Lys Ser Lys Leu Val Ser Asp Phe Arg
                965                 970                 975

Lys Asp Phe Gln Phe Tyr Lys Val Arg Glu Ile Asn Asn Tyr His His
            980                 985                 990

Ala His Asp Ala Tyr Leu Asn Ala Val Val Gly Thr Ala Leu Ile Lys
        995                 1000                1005

Lys Tyr Pro Lys Leu Glu Ser Glu Phe Val Tyr Gly Asp Tyr Lys
    1010                1015                1020

Val Tyr Asp Val Arg Lys Met Ile Ala Lys Ser Glu Gln Glu Ile
    1025                1030                1035

Gly Lys Ala Thr Ala Lys Tyr Phe Phe Tyr Ser Asn Ile Met Asn
    1040                1045                1050

Phe Phe Lys Thr Glu Ile Thr Leu Ala Asn Gly Glu Ile Arg Lys
    1055                1060                1065

Arg Pro Leu Ile Glu Thr Asn Gly Glu Thr Gly Glu Ile Val Trp
```

Asp Lys Gly Arg Asp Phe Ala Thr Val Arg Lys Val Leu Ser Met
    1085            1090                1095

Pro Gln Val Asn Ile Val Lys Lys Thr Glu Val Gln Thr Gly Gly
    1100            1105                1110

Phe Ser Lys Glu Ser Ile Leu Pro Lys Arg Asn Ser Asp Lys Leu
    1115            1120                1125

Ile Ala Arg Lys Lys Asp Trp Asp Pro Lys Lys Tyr Gly Gly Phe
    1130            1135                1140

Asp Ser Pro Thr Val Ala Tyr Ser Val Leu Val Val Ala Lys Val
    1145            1150                1155

Glu Lys Gly Lys Ser Lys Lys Leu Lys Ser Val Lys Glu Leu Leu
    1160            1165                1170

Gly Ile Thr Ile Met Glu Arg Ser Ser Phe Glu Lys Asn Pro Ile
    1175            1180                1185

Asp Phe Leu Glu Ala Lys Gly Tyr Lys Glu Val Lys Lys Asp Leu
    1190            1195                1200

Ile Ile Lys Leu Pro Lys Tyr Ser Leu Phe Glu Leu Glu Asn Gly
    1205            1210                1215

Arg Lys Arg Met Leu Ala Ser Ala Gly Glu Leu Gln Lys Gly Asn
    1220            1225                1230

Glu Leu Ala Leu Pro Ser Lys Tyr Val Asn Phe Leu Tyr Leu Ala
    1235            1240                1245

Ser His Tyr Glu Lys Leu Lys Gly Ser Pro Glu Asp Asn Glu Gln
    1250            1255                1260

Lys Gln Leu Phe Val Glu Gln His Lys His Tyr Leu Asp Glu Ile
    1265            1270                1275

Ile Glu Gln Ile Ser Glu Phe Ser Lys Arg Val Ile Leu Ala Asp
    1280            1285                1290

Ala Asn Leu Asp Lys Val Leu Ser Ala Tyr Asn Lys His Arg Asp
    1295            1300                1305

Lys Pro Ile Arg Glu Gln Ala Glu Asn Ile Ile His Leu Phe Thr
    1310            1315                1320

Leu Thr Asn Leu Gly Ala Pro Ala Ala Phe Lys Tyr Phe Asp Thr
    1325            1330                1335

Thr Ile Asp Arg Lys Arg Tyr Thr Ser Thr Lys Glu Val Leu Asp
    1340            1345                1350

Ala Thr Leu Ile His Gln Ser Ile Thr Gly Leu Tyr Glu Thr Arg
    1355            1360                1365

Ile Asp Leu Ser Gln Leu Gly Gly Asp Tyr Lys Asp Asp Asp
    1370            1375                1380

Asp Lys
    1385

<210> SEQ ID NO 35
<211> LENGTH: 221
<212> TYPE: DNA
<213> ORGANISM: Parachlorella sp.
<220> FEATURE:
<221> NAME/KEY: misc_feature
<223> OTHER INFORMATION: FBPase Intron 1

<400> SEQUENCE: 35
gtgagtgaga acagttttca gatcgaatag caccccccg cctctgcagc agtcgcatac    60
cggctgcagt aatagcttgg ttcaacggcg acctgaacaa gtactgtagt ttctatgcat   120

```
acgaacttta tcgaatagaa tcacgcttgg gtatcgatca taccttagcg ctcaatttca      180
ttggctgcta cagaccatat tttcctcttc acttgttgca g                         221

<210> SEQ ID NO 36
<211> LENGTH: 184
<212> TYPE: DNA
<213> ORGANISM: Parachlorella sp.
<220> FEATURE:
<221> NAME/KEY: misc_feature
<223> OTHER INFORMATION: FBPase Intron 2

<400> SEQUENCE: 36
gtgagaagag tttggctacc aaatctatct tttcatatca catataccgc ctgatattct      60
gaggtggtgg cttttgtctt tttctttcag tattttctt cgttgggaac ctaccgcgag      120
ggcattcatt gtggcggatc tgtaagtgcg accaggctgt atccaatatt ttttcctatc     180
gcag                                                                 184

<210> SEQ ID NO 37
<211> LENGTH: 266
<212> TYPE: DNA
<213> ORGANISM: Parachlorella sp.
<220> FEATURE:
<221> NAME/KEY: misc_feature
<223> OTHER INFORMATION: FBPase Intron 3

<400> SEQUENCE: 37
gtgagaatct ctgcttgtcg aatgtgtcca gttgtgtctt gaatcctggc aagatgttct     60
tttcaccatc cgtcctgcaa aagtgtcaga agtagcatct ctcgatcgcg ttgtcacttc    120
aacgcctccg caactccccc cgttgtgaat cctgtggtca tggctcagct tttcagatct   180
ctacctgcat gttgtttgcc tgtctcagtc ctgcctgcac aaatcatcgc ccttgtttac   240
tccttgcaat cacggattgt gtgcag                                         266

<210> SEQ ID NO 38
<211> LENGTH: 429
<212> TYPE: DNA
<213> ORGANISM: Parachlorella sp.
<220> FEATURE:
<221> NAME/KEY: misc_feature
<223> OTHER INFORMATION: FBPase Intron 4

<400> SEQUENCE: 38
gtgagtggag ggctggggtt tgggggtggg gggtggggag ggaggcacgg atggtgtttt     60
ctcatgtcca accgtggttc atgcaaccga acagcagttt cacaagatgg ttccaacagg    120
gtgctccatt tctccctgac aaaacctcgt gcggtccatc tggtatagct gggttagtag   180
ggggttgtgg gctgtccaca gtcagtgcga agcaggctct attgagcgtg tgctagtgtg   240
tgctgtgctg attggcattt tgttgggccg agtgttagga ttagggtaaa tcaccctaat   300
taaccttaca taataggact gtatgcaaat ttgttttcca aaaactctac ccagcgtggt   360
cagactgcat gcactgtgga gcatgcatgg ggctgaccct gttgatcctg ctcattctgc   420
ttcctccag                                                            429

<210> SEQ ID NO 39
<211> LENGTH: 256
<212> TYPE: DNA
<213> ORGANISM: Parachlorella sp.
<220> FEATURE:
<221> NAME/KEY: misc_feature
```

<223> OTHER INFORMATION: FBPase Intron 5

<400> SEQUENCE: 39

```
gtaggtgcag gaagaagtga atgatgcaca catggtggaa tcgtgataca agcagcagca      60
agtgttggac caagacatgt gcgtgctttg ctgctgccaa gctggcactg caccaggtcg     120
tgcattgatc tgcacatttg atatactgtg agagtcagac gacgtccttt cagagcctgt     180
gtgtgattct ccaggggtta acacgagttt cctttctgcc agtgagtcac cctctcgctg     240
ctcgctcctg gtgcag                                                     256
```

<210> SEQ ID NO 40
<211> LENGTH: 338
<212> TYPE: DNA
<213> ORGANISM: Parachlorella sp.
<220> FEATURE:
<221> NAME/KEY: misc_feature
<223> OTHER INFORMATION: FBPase Intron 6

<400> SEQUENCE: 40

```
gtgataatta tgcaagaaaa tgaaaaaaat catagaaagg aaggaggggga tgttgatgtt      60
tggtgtgtgg cagggtgtgt gttggactga tgcctattgg attgccggtg gcctgcatgt     120
cagctgcttc tcactaaatt atcgctcggg aaatgcgcag tccacaacta ttcccaacat     180
caatgcccaa acagttgcaa acagctgct gcttgcccca ccctttgatg gtcttctgca     240
cctggaaagg gtgcactgtt tgtcttcttt gagcttcaag ctcgtctccc tgctccttgc     300
ctcacttgcc ttcctcgtct gcccctccct ttctgcag                             338
```

<210> SEQ ID NO 41
<211> LENGTH: 259
<212> TYPE: DNA
<213> ORGANISM: Parachlorella sp.
<220> FEATURE:
<221> NAME/KEY: misc_feature
<223> OTHER INFORMATION: FBPase Intron 7

<400> SEQUENCE: 41

```
gtgagtgcgg gacatcacat agggagggga gggagggatt gggtggaggg ggagatgctg      60
gtcttttgct gagatgcaag tgtgggtcca cgcagacgtg ggttgactgt ccaacagacc     120
agcagctatc acaagttata ccaccatgca cttatgagaa cttccatcag tttcctttgg     180
catgcacctg aatgccaatt ggtcttgctt tggcctgcac tcatgcttgc actcctgccc     240
ctctccccgc tacatgcag                                                  259
```

<210> SEQ ID NO 42
<211> LENGTH: 231
<212> TYPE: DNA
<213> ORGANISM: Parachlorella sp.
<220> FEATURE:
<221> NAME/KEY: misc_feature
<223> OTHER INFORMATION: FBPase Intron 8

<400> SEQUENCE: 42

```
gtgagtggca ttaagtagca ggattgaatt tatttcctgg acttggccag ataacatgtg      60
acacaccatg gtagagaagt tgtttgttct ggcgaagaac ccttgacaaa ttgtgtcatc     120
cgttttgga ctatatatcg tttgaaatgc aaaggcctcc ataaaagatc aggcagtgcg     180
cccaagtttt gagcaggaag ctgacccctg tgcaccatgc tgtgctgtgc a              231
```

<210> SEQ ID NO 43

```
<211> LENGTH: 237
<212> TYPE: DNA
<213> ORGANISM: Parachlorella sp.
<220> FEATURE:
<221> NAME/KEY: misc_feature
<223> OTHER INFORMATION: FBPase Intron 9

<400> SEQUENCE: 43
gtggggaata cttttggca agagcgtgtt ttgtggtttc tcgctcacct gccctgacta      60
gaacttctgt tgacaggccc acggtctgta ggccacgtct gtcagaccat gtggaacttt    120
cttctattgc ataacgcgag ctgccccaca tgttaatcct tgttgggtgt ctcgcatcac    180
atcatgtcgc ctttcatgca cttctaacca ttatgtgaac ccctcgccc tctgcag        237

<210> SEQ ID NO 44
<211> LENGTH: 5540
<212> TYPE: DNA
<213> ORGANISM: Artificial Sequence
<220> FEATURE:
<223> OTHER INFORMATION: Synthetic
<220> FEATURE:
<221> NAME/KEY: misc_feature
<223> OTHER INFORMATION: Gene encoding Streptococcus pyogenes Cas9 with
      FLAG tag, nuclear localization sequences, peptide linker, and
      FBPase introns 1-5, codon optimized for expression in
      Parachlorella

<400> SEQUENCE: 44
atgcccaaga agaagcggaa agtcggggac tacaaggacg acgatgacaa actggagcct      60
ggggagaagc cctataagtg tcctgagtgc gggaagagct tcagccaatc tggagcactg    120
acaaggcacc agaggacaca tacacgcgac aagaagtaca gcatcgggct ggatatcggg    180
accaattctg tgggatgggc cgtgattacc gacgagtata aggtgcccag caagaagttc    240
aaggtgctgg gaacacagac cgccacagc attaagaaga acctgatcgg ggcgctgctg    300
tttgattctg agagacagc agaggcaacc gtgagtgaga cagttttca gatcgaatag    360 cacccccccg cctctgcagc agtcgcatac cggctgcagt aatagcttgg ttcaacggcg    420
acctgaacaa gtactgtagt ttctatgcat acgaactta tcgaatagaa tcacgcttgg    480
gtatcgatca taccttagcg ctcaatttca ttggctgcta cagaccatat tttcctcttc    540
acttgttgca gcgcctgaaa agaacagcaa gaaggcgcta cacccgccgc aagaatagga    600
tttgctacct gcaagagatc ttcagcaacg agatggccaa ggtggacgac agcttcttcc    660
atagactgga ggagtcgttc ctggtggagg aggataagaa gcacgagagg caccccatct    720
tcggtgagaa gagtttggct accaaatcta tcttttcata tcacatatac cgcctgatat    780
tctgaggtgg tggcttttgt ctttttcttt cagtattttt cttcgttggg aacctaccgc    840
gagggcattc attgtggcgg atctgtaagt gcgaccaggc tgtatccaat atttttcct    900 atcgcaggga acattgtgga tgaggtggcc taccacgaga agtaccccac aatctaccac    960
ctgcgcaaga agctggtgag aatctctgct tgtcgaatgt gtccagttgt gtcttgaatc   1020
ctggcaagat gttctttca ccatccgtcc tgcaaaagtg tcagaagtag catctctcga   1080
tcgcgttgtc acttcaacgc ctccgcaact cccccgttg tgaatcctgt ggtcatggct   1140
cagcttttca gatctctacc tgcatgttgt ttgcctgtct cagtcctgcc tgcacaaatc   1200
atcgcccttg tttactcctt gcaatcacgg attgtgtgca ggtggacagc acagataagg   1260
ccgatctgag gctgatctac ctggcattgg cccacatgat caagtttagg gggcacttcc   1320
tcatcgaggg ggatttgaac cccgacaaca gcgatgtgga caagctgttc atccagctgg   1380
```

```
tgagtggagg gctggggttt ggggggtgggg ggtggggagg gaggcacgga tggtgttttc    1440
tcatgtccaa ccgtggttca tgcaaccgaa cagcagtttc acaagatggt tccaacaggg    1500
tgctccattt ctccctgaca aaacctcgtg cggtccatct ggtatagctg ggttagtagg    1560
gggttgtggg ctgtccacag tcagtgcgaa gcaggctcta ttgagcgtgt gctagtgtgt    1620
gctgtgctga ttggcatttt gttgggccga gtgttaggat tagggtaaat caccctaatt    1680
aaccttacat aataggactg tatgcaaatt tgttttccaa aaactctacc cagcgtggtc    1740
agactgcatg cactgtggag catgcatggg gctgaccctg ttgatcctgc tcattctgct    1800
tcctccaggt gcagacctac aaccagctgt ttgaggagaa ccccatcaac gcatctgggg    1860
ttgacgcaaa ggccattctg tctgcaaggt aggtgcagga agaagtgaat gatgcacaca    1920
tggtggaatc gtgatacaag cagcagcaag tgttggacca agacatgtgc gtgctttgct    1980
gctgccaagc tggcactgca ccaggtcgtg cattgatctg cacatttgat atactgtgag    2040
agtcagacga cgtcctttca gagcctgtgt gtgattctcc aggggttaac acgagttttcc    2100
tttctgccag tgagtcaccc tctcgctgct cgctcctggt gcaggctgag caagtcaagg    2160
agactggaga acctgatcgc ccaattgcct ggagagaaga agaacgggct gttcgggaac    2220
ctgatcgcat tgtctctggg gttgaccccc aacttcaaga gcaacttcga cctggcagag    2280
gacgcaaaac tgcagctgag caaggacacc tacgacgatg atctggacaa cctgctggcc    2340
cagattggag atcagtacgc agacctgttc ctggcagcca agaatctgag cgacgcaatt    2400
ctgctgagcg acattctgcg cgtgaacacc gagatcacca aggcacctct gagcgcaagc    2460
atgatcaaga ggtacgacga gcaccaccaa gacctgacac tgctgaaagc actggtgaga    2520
cagcagctgc ctgagaagta caaggagatc ttcttcgacc agagcaagaa cgggtacgct    2580
gggtacattg atgagggagc aagccaagag gagttctaca agttcatcaa gcccatcctg    2640
gagaagatgg acgggacaga agagttgctg gtgaagctga atcgcgagga tctgctgagg    2700
aagcagagga cattcgacaa tgggagcatc ccacaccaga tccatctggg agagctgcac    2760
gcaattctga ggagacaaga ggacttctac ccgttcctga aggacaatcg cgagaagatc    2820
gagaagatcc tcacgttccg catcccgtac tatgtgggac ctctggcaag ggggaactct    2880
agatttgcct ggatgacccg caagagcgag gagacaatta caccctggaa cttcgaggag    2940
gtggtggata aggggcatc tgcacagagc ttcatcgaga ggatgaccaa cttcgacaag    3000
aacctgccca cgagaaggt actgcctaag cattcactgc tgtacgagta cttcaccgtg    3060
tacaacgagc tgaccaaggt gaagtacgtg acagagggga tgaggaagcc agcatttctg    3120
agcggagagc aaaagaaggc catcgtggat ctgctgttca gaccaaccg caaggtgacc    3180
gtgaagcagc tgaaggagga ctacttcaag aagatcgagt gcttcgacag cgtggagatt    3240
tctggagtgg aggaccgctt caacgcatct ttggggacat accacgacct gctgaagatc    3300
atcaaggaca aggacttcct ggacaacgag gagaacgagg acatcctgga ggacattgtg    3360
ctgacactga ccctgttcga ggatagggag atgatcgagg agcgcctgaa gacatacgca    3420
cacctgtttg acgacaaggt gatgaagcag ctgaagagga ggcgctatac tggatgggga    3480
aggctgtcaa ggaagctgat taacgggatc gcgacaagc agagcgggaa gacaattctg    3540
gacttcctga agagcgacgg gttcgcaaac cgcaacttca tgcagctgat ccacgacgat    3600
agcctgacct tcaaggagga catccagaag gcccaagtgt ctggacaagg ggatagcctg    3660
catgagcaca tcgcaaatct ggctgggtca cccgcaatca gaagggaat tctgcagacc    3720
gtgaaggtgg tggatgagct ggtgaaggtg atgggaaggc acaaacccga gaacatcgtg    3780
```

```
atcgagatgg caagggagaa ccagacaacc cagaagggac agaagaactc tagggagcgc   3840
atgaagcgca tcgaggaggg aattaaggag ctgggaagcc agatcctgaa ggagcatcct   3900
gtggagaaca cccaactgca gaacgagaag ctgtacctgt actacctgca gaacgggagg   3960
gacatgtacg tggatcaaga gctggacatc aaccgcctga cgactatga cgtggaccac   4020
attgtgcctc agtcgttcct gaaggacgac agcatcgaca acaaggtgct gacaaggagc   4080
gacaagaatc gcggaaagag cgacaacgtg ccttcagaag aggtggtgaa gagatgaag    4140
aactactggc gccagctgct gaacgcaaag ctgattacac agcgcaagtt cgacaacctg   4200
accaaggcag agaggggagg actgtcagaa ctggataagg ccgggttcat caagaggcaa   4260
ctggtggaga cacgccagat cacaaagcat gtggcccaga ttctggacag ccgcatgaac   4320
accaagtacg acgagaacga caagctgatc cgcgaggtga aggtgattac cctgaagagc   4380
aagctggtga gcgactttcg caaggacttc cagttctaca aggtgcgcga gatcaacaac   4440
taccaccacg cacacgacgc ctacctgaat gcagttgtgg aacagcccct gatcaagaag   4500
taccccaagc tggagagcga gttcgtgtat ggggactaca aggtgtacga cgtgcgcaag   4560
atgatcgcca agtctgagca agagatcggg aaggcaaccg ccaagtactt cttctacagc   4620
aacatcatga acttcttcaa gaccgagatc accctggcca tggggagat taggaagaga   4680
cccctgatcg agaccaacgg agagactgga gagatcgtgt gggataaggg gagggactt    4740
gcaacagtgc gcaaagtgct gagcatgcct caagtgaaca tcgtgaagaa gaccgaggtg   4800
cagactgggg gattctcaaa ggagagcatt ctgcccaagc gcaacagcga taagctgatt   4860
gcacgcaaga aggactggga ccccaagaag tatgggggt ttgatagccc caccgtggca    4920
tattctgtgt tggttgtggc caaggtggag aaggggaaga gcaagaagct gaagagcgtg   4980
aaggagctgc tggggatcac cattatggag aggagcagct cgagaagaa ccccatcgac    5040
ttcctggagg caaaggggta taaggaggtg aagaaggacc tgatcatcaa gctgcccaag   5100
tacagcctgt tcgagctgga gaatggggagg aagaggatgc tggcatctgc tggagaactg  5160
cagaagggga atgagttggc actgcctagc aagtacgtga acttcctgta cctggccagc   5220
cactacgaga agctgaaggg atcacccgag gacaatgagc agaagcagct gtttgtggag   5280
cagcacaagc actacctgga cgagatcatc gagcagatca gcgagttcag caagcgcgtg   5340
attctggcag acgcaaacct ggataaggtg ctgagcgcct acaacaagca ccgcgataag   5400
cccattcgcg agcaagcaga gaacatcatc cacctgttca ccctgaccaa cctgggagca   5460
cctgcagcat tcaagtactt cgacaccacc atcgaccgca gaggtacac aagcaccaag   5520
gaagtgctgg acgcaaccct                                               5540
```

```
<210> SEQ ID NO 45
<211> LENGTH: 23
<212> TYPE: DNA
<213> ORGANISM: Parachlorella sp.
<220> FEATURE:
<221> NAME/KEY: misc_feature
<223> OTHER INFORMATION: SRP54 CRISPR target sequence (including PAM)

<400> SEQUENCE: 45
ggcgtgggac atggtgcgca agg                                             23

<210> SEQ ID NO 46
<211> LENGTH: 32
<212> TYPE: DNA
<213> ORGANISM: Artificial Sequence
```

```
<220> FEATURE:
<223> OTHER INFORMATION: Synthetic
<220> FEATURE:
<221> NAME/KEY: misc_feature
<223> OTHER INFORMATION: AE596 Primer

<400> SEQUENCE: 46
tgcgacatgc agcttactaa cctgctcgac at                                    32

<210> SEQ ID NO 47
<211> LENGTH: 28
<212> TYPE: DNA
<213> ORGANISM: Artificial Sequence
<220> FEATURE:
<223> OTHER INFORMATION: Synthetic
<220> FEATURE:
<221> NAME/KEY: misc_feature
<223> OTHER INFORMATION: AE597 Primer

<400> SEQUENCE: 47
atgggctcct tgatgttgtc cgccgtta                                         28

<210> SEQ ID NO 48
<211> LENGTH: 21
<212> TYPE: DNA
<213> ORGANISM: Artificial Sequence
<220> FEATURE:
<223> OTHER INFORMATION: Synthetic
<220> FEATURE:
<221> NAME/KEY: misc_feature
<223> OTHER INFORMATION: AE405 Primer

<400> SEQUENCE: 48
acccaaaccc atgccagtgt a                                                21

<210> SEQ ID NO 49
<211> LENGTH: 25
<212> TYPE: DNA
<213> ORGANISM: Artificial Sequence
<220> FEATURE:
<223> OTHER INFORMATION: Synthetic
<220> FEATURE:
<221> NAME/KEY: misc_feature
<223> OTHER INFORMATION: AE406 Primer

<400> SEQUENCE: 49
actgtatgca gagtggtctg aagtg                                            25

<210> SEQ ID NO 50
<211> LENGTH: 570
<212> TYPE: DNA
<213> ORGANISM: Artificial Sequence
<220> FEATURE:
<223> OTHER INFORMATION: Synthetic
<220> FEATURE:
<221> NAME/KEY: misc_feature
<223> OTHER INFORMATION: Nat1 gene encoding nourseothricin
      acetyltransferase from Streptomyces noursei, codon-optimized for
      Parachlorella

<400> SEQUENCE: 50
atgaccacac tcgacgacac cgcatacaga taccgcacaa gcgttcctgg cgacgcagag       60
gcaattgagg cattagatgg cagcttcacc accgacaccg tgtttagagt gacagcaacc      120
ggcgacggct ttacacttag agaggttcca gtggacccgc cattgacaaa ggtgtttcca      180
gacgacgaga gcgacgatga gagcgatgct ggtgaagatg cgacccaga tagccgcaca       240 tttgtggcat acgcgatga tgcgaccctt gctgggtttg tggtggtgag ctactctggc      300
```

```
tggaatagac gcttgaccgt ggaggatatc gaggttgcac cagagcatag aggccatgga      360
gtgggtagag cactgatggg tctggcaacc gagtttgcaa gggagagagg tgctggtcat      420
ctgtggttgg aggtgacaaa cgtgaacgca ccagcgatcc acgcatacag aagaatgggc      480
ttcacgctgt gcggcctgga tacagcactg tatgatggca cagcgagcga tggtgagcaa      540
gcactgtaca tgagcatgcc atgcccgtaa                                       570
```

<210> SEQ ID NO 51
<211> LENGTH: 2862
<212> TYPE: DNA
<213> ORGANISM: Artificial Sequence
<220> FEATURE:
<223> OTHER INFORMATION: Synthetic
<220> FEATURE:
<221> NAME/KEY: misc_feature
<223> OTHER INFORMATION: Nat1 gene Intronylated with Parachlorella RPS4
      Introns

<400> SEQUENCE: 51

```
atgaccactt tgtgagttct gagaagctga ttgttgttta acttctttga aagctttatc       60
gaagattctg caagcgatga acattgcttg tcaagaccga gagctgcatg cccacttgac      120
atccagcttt gaacggctct tcatgttttga tttgtttctg attgtaggga cgacaccgca      180
tacagatacc gcacaagcgt tcctggcgac gcagaggcaa ttgaggcatt agatggcagc      240
ttcaccaccg acaccgtgtt tagagtgagt gcagcgtcag ctgtggcagt tgttggcttt      300
cgtctcagtc agtagtttgc tgggattgat tatggagggc acagttgcaa ttttgagttg      360
cacgttgcga caagcgtgtt gacaaagcgt ggtcaagccg gccagtcttg ccggtggcgg      420
gtggcttggt ctaacttccg ctctacagca atcgttttgt tcatggttac ggggctggcg      480
tgccagaaag tcctggtcag ccaccctcgc ttcaaagccg tagcccaaca actttgcgaa      540
tatgttcgat ttgcaggtaa cagcaaccgg cgacggcttt acactagag aggttccagt      600 ggacccgcca ttgacaaagg tacagctctg cgtgcaacag gttgcaagat gcagcgcagg      660
tcttccctgg tcaaacgatg tatgcagagt tgagaggcac ttgagctggg tgaatggcgt      720
gggctcgtag gtagtgtgca gggcaggaag ggcagccaat tttggagttg tggtccggtg      780
tcgttgcttc gagccttatt aggactcttg ctcatcaaag cgttagttgt gaataagttg      840
atctgaaagg atgttatgta cagcaagcag cagcagttaa gagtctgggg agtagctgca      900
cagggcgagg tgtcaagatg ggaagggtcc tgcctcctta tgtgtttttc cctgtagggg      960
aggaagcctc ttatgggcaa tggttgggca tattttccag ccagcccttc tttctatagg     1020
ggccagggtg ggcccagctc gtcttggctt ccaccaccag gagagtgagg gcattgaagg     1080
gccataaata gtcctcccat ctacgtgcac cagagggtgt cgtctaggct gtgcatgcca     1140 cgagggaag gagccaagaa tgagtgtatg ggttgtttc atgtttaggc tgggataaaa     1200
ctgttttcaa ttgcgcctgc cgggtgaaaa ccacagcagc atcagcaagc ttggagaagg     1260
ccagcccgcc cagcacaggc tcacgttccc actcaggcgg tcagtcgggc gggggtgtga     1320
gtcaggcagg cgagggtgtc tgtgcctgac atcagcacct ctgcttagcc actgcagccc     1380
ctggagcagg gtagggcgtc atttgcagca atcacctgct gcctcacacg tcgcagcttg     1440
gaatttcaac gaccatcagc gctggggttg ttgagggatc atagcagatt ttggtgcagc     1500
ctggttgtca tgctctttgt ggaatggcct ctatgttcga gcaattcgtt ggatgttgag     1560
gtgcttgggg acagagagtc gaatgatggg ccagggtcaa acatgcgagc gtttggctga     1620
```

```
gtcagcggtt tttgctggtc acttttcctt ttgtttctta tttaggtttg atggatgtgt   1680
tttgtgctgc tgccctgaag ctgcagcagc gtgtctgccc tgcgctactg cgggcaccaa   1740
ggctatgtgc tggtgcactc ggctgcgctg cacctgtgca cctcgcactc cgtccagcct   1800
ccatgcagca cacgtactca cggtgtcctc ctgacctgtc gtacgctatt ccaaacttgc   1860
tcttttgctg ccgctgctct cgtacacaat tgctgttgat tatcgatatc taatcgagcg   1920
cctgctgact gaactccgca ggtgtttcca gacgacgaga gcgacgatga gagcgatgct   1980
ggtgaagatg gcgacccaga tagccgcaca tttgtggcat acggcgatga tggcgacctt   2040
gctgggtttg tggtggtgag ctactctggc tggaatagac gcttgaccgt ggaggatatc   2100
gaggttgcac cagagcatag aggccatgga gtgggtagag cactgatggg tctggcaacc   2160
gagtttgcaa ggtgggtggg ctctgaagga ggaggaggga gcgggtgatt aaacagggcc   2220
tgcatgaaga ggagcagggg ctgcatggac agcaggggga aggtgcagaa gggagggtca   2280
agcggggttc aggtggctgt gggtttctgc acgagcagtg aaagaagctg tatccttcca   2340
cctgctttca ctggcgaaag gttgaaaaca ggatgtcgca gctggaaaga tgttgcgctg   2400
tcaagtgcaa gccatggttg agggtatgcc tgtgtgcatg tgcttcttaa agttactcct   2460
gttctatggt tctgggtgct tgttgtttgt ggtgcaggga gagaggtgct ggtcatctgt   2520
ggttggaggt gacaaacgtg aacgcaccag cgatccacgc atacagaaga atgggcttca   2580
cgctgtgcgg cctggataca gcactgtatg atggtgaggg ggcatgtaag caatggcagg   2640
caattcaaga acgaatcatt gctgcaaatg ctgggatggt atgcagctga ggtatctatt   2700
gccttgtatt ttgtctcgca ttgcatcggt ggtgcgttct gtggcctgag gcacagttct   2760
tgctgtttga taagggttcg actgagttgt cgtgtgtgct gtgctgcagg cacagcgagc   2820
gatggtgagc aagcactgta catgagcatg ccatgcccgt aa                      2862
```

COMPOSITIONS AND METHODS FOR EXPRESSING GENES IN ALGAE

CROSS REFERENCE TO RELATED APPLICATIONS

This application claims benefit of priority under 35 U.S.C. 119(e) to U.S. Ser. No. 62/261,217, filed Nov. 30, 2015, U.S. Ser. No. 62/261,777, filed Dec. 1, 2015, and U.S. Ser. No. 62/323,480, filed Apr. 15, 2016, the entire contents of which are incorporated herein by reference in their entireties.

INCORPORATION BY REFERENCE OF SEQUENCE LISTING

The material in the accompanying sequence listing is hereby incorporated by reference into the application. The accompanying sequence listing text file, name SGI-1920_3_Sequence_Listing.txt, was created on Nov. 29, 2016, and is 67 kb. The file can be accessed using Microsoft Word on a computer that uses Window OS.

FIELD OF THE INVENTION

The present invention relates generally to the field of genetic engineering of eukaryotic cells, such as microorganisms such as algae.

BACKGROUND

Algal cells are a promising source of biofuels (Wijffels & Barbosa (2010) *Science* 329:796-799). Their ability to harness solar energy to convert carbon dioxide into carbon-rich lipids already exceeds the abilities of oil-producing agricultural crops, with the added advantage that algae grown for biofuel do not compete with oil-producing crops for agricultural land (Wijffels & Barbosa, 2010). *Parachlorella* phytoplankton are unicellular green algae (phylum Chlorophya) of the Trebouxiophyceae class that can be cultured easily, rapidly, and economically. In order to maximize algal fuel production, new algal strains will need to be engineered for growth and carbon fixation at an industrial scale (Wijffels & Barbosa, 2010).

While it will be necessary to manipulate algal genomes, such as the *Parachlorella* genome, in order to maximize biofuel output, this has proven difficult to date because of the thick cell wall that surrounds many algal cells, including *Parachlorella* cells. In fact, to our knowledge, techniques for reliable and reproducible methods for transformation of *Parachlorella* cells have not been developed or published. There is a lack of knowledge relating to techniques suitable for transforming may species of algae, including algae of the Trebouxiophyceae class, such as *Parachlorella* cells, with transgenes. Consistent procedures for genetic manipulation of these organisms are needed.

Further, modern recombinant strain development requires robust and efficient tools for expressing transgenes to alter cellular metabolism and physiology in desired ways. An essential component of any genetic engineering "toolkit" is a suite of functional promoters to drive transgene-expression. There is a need for endogenous promoters, cloned and verified, from the strains for which recombinant DNA technology is being developed as well as additional strategies for increasing transformation of microorganisms such as algae and improved expression of heterologous genes.

SUMMARY

In some aspects, the disclosure provides an isolated DNA molecule comprising a sequence having at least 80%, at least 85%, at least 90%, at least 95%, at least 96%, at least 97%, at least 98%, or at least 99% identity to at least 100, at least 200, at least 300, at least 400, or at least 500 contiguous nucleotides of a sequence selected from the group consisting of SEQ ID NO:1, SEQ ID NO:4, SEQ ID NO:8, SEQ ID NO:11, SEQ ID NO:13, SEQ ID NO:15, SEQ ID NO:17, SEQ ID NO:19, SEQ ID NO:21, SEQ ID NO:23. For example, the isolated DNA molecule can comprise a sequence having at least 80% at least 85%, at least 90%, at least 95%, at least 96%, at least 97%, at least 98%, or at least 99% identity to at least 100, at least 200, at least 300, at least 400, or at least 500 contiguous nucleotides extending in the 5' direction from the 3' end of a sequence selected from the group consisting of SEQ ID NO:1, SEQ ID NO:4, SEQ ID NO:8, SEQ ID NO:11, SEQ ID NO:13, SEQ ID NO:15, SEQ ID NO:17, SEQ ID NO:19, SEQ ID NO:21, and SEQ ID NO:23.

In some aspects, the present disclosure provides a promoter comprising a nucleic acid sequence having at least 80%, at least 85%, at least 90%, at least 95%, at least 96%, at least 97%, at least 98%, or at least 99% identity to at least 100, at least 200, at least 300, at least 400, or at least 500 contiguous nucleotides of a sequence selected from the group consisting of SEQ ID NO:1, SEQ ID NO:4, SEQ ID NO:8, SEQ ID NO:11, SEQ ID NO:13, SEQ ID NO:15, SEQ ID NO:17, SEQ ID NO:19, SEQ ID NO:21, and SEQ ID NO:23. For example, the promoter can comprise a sequence having at least 80%, at least 85%, at least 90%, at least 95%, at least 96%, at least 97%, at least 98%, or at least 99% identity to at least 100, at least 200, at least 300, at least 400, or at least 500 contiguous nucleotides extending in the 5' direction from the 3' end of a sequence selected from the group consisting of SEQ ID NO:1, SEQ ID NO:4, SEQ ID NO:8, SEQ ID NO:11, SEQ ID NO:13, SEQ ID NO:15, SEQ ID NO:17, SEQ ID NO:19, SEQ ID NO:21, and SEQ ID NO:23. In some embodiments, the promoter comprises a sequence having at least 80%, at least 85%, at least 90%, at least 95%, at least 96%, at least 97%, at least 98%, or at least 99% identity to at least 100, at least 200, at least 300, at least 400, or at least 500 contiguous nucleotides extending in the 5' direction from the 3' end of a sequence selected from the group consisting of SEQ ID NO:1, SEQ ID NO:4, SEQ ID NO:8, and SEQ ID NO:17.

In further aspects, the disclosure provides an isolated DNA molecule comprising a sequence having at least 80%, at least 85%, at least 90%, at least 95%, at least 96%, at least 97%, at least 98%, or at least 99% identity to at least 100, at least 200, at least 300, or at least 400 contiguous nucleotides of a sequence selected from the group consisting of SEQ ID NO:7, SEQ ID NO:9, SEQ ID NO:12, SEQ ID NO:14, SEQ ID NO:16, SEQ ID NO:18, SEQ ID NO:20, SEQ ID NO:22, and SEQ ID NO:24, for example, comprising a sequence having at least 80%, at least 85%, at least 90%, at least 95%, at least 96%, at least 97%, at least 98%, or at least 99% identity to at least 100, at least 200, at least 300, or at least 400 contiguous nucleotides extending in the 3' direction from the 5' end of a sequence selected from the group consisting of SEQ ID NO:7, SEQ ID NO:9, SEQ ID NO:12, SEQ ID NO:14, SEQ ID NO:16, SEQ ID NO:18, SEQ ID NO:20, SEQ ID NO:22, and SEQ ID NO:24. In some embodiments, the DNA molecule comprises a terminator. In some embodiments, the terminator comprises a sequence having at least 80%, at least 85%, at least 90%, at least 95%, at least 96%, at least 97%, at least 98%, or at least 99% identity to at least 100, at least 200, at least 300, or at least 400 contiguous nucleotides of a sequence selected from the group consisting of SEQ ID NO:7, SEQ ID NO:9, and SEQ ID NO:18. The terminator can be operably linked to a heterologous sequence encoding a polypeptide or functional RNA.

In further aspects, provided herein are engineered genes encoding polypeptides in which the engineered genes include two or more introns that are heterologous with respect to the gene encoding the polypeptide, i.e., two or more introns derived from genes other than the genes from with the polypeptide-encoding sequences are derived. The two or more heterologous introns can be derived from the same gene, which is a different from the gene from which the polypeptide-encoding sequences are derived. The engineered genes can include two, three, four, five, six, seven, eight, nine, or more than nine heterologous introns, which can optionally all be derived from the same gene. An engineered gene that includes heterologous introns can be operably linked to a heterologous promoter, where the promoter in some embodiments can be derived from the same gene from which the two or more introns are derived. An engineered gene that include heterologous introns can further include a terminator operably linked to the polypeptide encoding sequence, where the terminator in some embodiments can be derived from the same gene the two or more introns and the promoter are derived from. In some embodiments, the engineered gene includes two or more introns having at least 80%, or at least 85%, 90%, 95%, 96%, 97%, 98%, or 99% identity to a sequence selected from the group consisting of SEQ ID NO:25, SEQ ID NO:26, SEQ ID NO:27, SEQ ID NO:28, SEQ ID NO:29, SEQ ID NO:35, SEQ ID NO:36, SEQ ID NO:37, SEQ ID NO:38, SEQ ID NO:39, SEQ ID NO:40, SEQ ID NO:41, SEQ ID NO:42, or SEQ ID NO:43. For example, an engineered gene can include three or more introns selected from the group of introns having at least 80%, 85%, 90%, 95%, 96%. 97%, 98%, or 99% identity to SEQ ID NO:25, SEQ ID NO:26, SEQ ID NO:27, SEQ ID NO:28, and SEQ ID NO:29. In further examples, an engineered gene can include three or more introns selected from the group of introns having at least 80%, 85%, 90%, 95%, 96%. 97%, 98%, or 99% identity to SEQ ID NO:35, SEQ ID NO:36, SEQ ID NO:37, SEQ ID NO:38, SEQ ID NO:39, SEQ ID NO:40, SEQ ID NO:41, SEQ ID NO:42, and SEQ ID NO:43.

The at least two, at least three, at least four, or at least five heterologous introns that are derived from a different gene than the gene from which the amino acid-encoding sequences of the engineered gene are derived can be derived from a species different from the species from which the polypeptide encoded by the gene is derived. The amino acid-encoding sequences of the gene can be codon-optimized, for example, for expression in a host organism of interest. The at least two, at least three, at least four, or at least five heterologous introns can be naturally-occurring introns or can be derived from naturally-occurring introns, for example, the at least two, at least three, at least four, or at least five introns can be at least 80%, at least 85%, at least 90%, at least 95%, at least 96%, at least 97%, at least 98%, or at least 99% identical to a naturally-occurring intron or to an internally deleted variant of a naturally-occurring intron, for example, an intron having from 1 to at least 2000 bp internally deleted from the naturally-occurring intron sequence. The at least two, at least three, at least four, or at least five heterologous introns engineered into a gene to be expressed in a transgenic organism can all be derived from the same species, and in some embodiments are all derived from the same gene.

A nucleic acid molecule as provided herein can include an engineered gene that includes at least three, at least four, at least five, at least six, at least seven, at least eight, or at least nine heterologous introns, where at least two, at least three, at least four, at least five, at least six, at least seven, at least eight, at least nine, or all of the heterologous introns are derived from the same gene. In particular embodiments, all of the introns of the engineered gene may be derived from a species that is not the source of the amino acid-encoding sequences. In some examples, the polypeptide encoded by the engineered gene is derived from a first species, and the at least three heterologous introns are derived from a second species. The engineered gene can be operably linked to a promoter that in some examples may be derived from the same species as the heterologous introns. A nucleic acid molecule can optionally further comprise a terminator operably linked to the engineered gene, where the terminator may be derived from the same species as the heterologous introns. The engineered gene can optionally be codon-optimized, for example, the engineered gene can be codon-optimized for expression in a species from which the at least three heterologous introns are derived. In various embodiments, an engineered gene that is intronylated as disclosed herein can be a gene encoding a prokaryotic protein, such as a protein conferring resistance to an antibiotic or toxin or, for example, an RNA-guided endonuclease such as a cas protein. In various embodiments an engineered gene can encode a selectable marker protein, detectable marker protein, or an RNA-guided endonuclease, such as but not limited to a Class II RNA-guided endonuclease, that may be, for example, a Cas9, Cpf1, C2c1, C2c2, or C2c3 RNA-guided nuclease. RNA-guided endonuclease. In alternative embodiments, an engineered gene can encode a metabolic enzyme, a kinase, a phosphatase, a nucleotide cyclase, a phosphodiesteras, a G protein, a protein involved in cell signaling, a transcription factor, a transcriptional activator, a cell cycle protein, a receptor, a porin, a channel protein, a transporter, a protein of a secretory system or protein import system, a ribosomal protein, a translation factor, a structural protein, a DNA binding protein, etc.

A nucleic acid molecule that includes an engineered gene that includes at least three heterologous introns, such as any disclosed hereinabove or in the description herein, can demonstrate a higher level of expression when introduced into a cell than is demonstrated by a nucleic acid molecule that includes an engineered gene that does not include at least three heterologous introns introduced into a cell. Increased expression can be reflected in higher transformation rates, where the engineered gene encodes a selectable marker, for example, or a higher frequency of transformed cells exhibiting fully penetrant expression of the engineered gene.

In additional aspects, the disclosure provides an expression cassette comprising a promoter as disclosed herein and a heterologous gene encoding a polypeptide or a functional RNA sequence operably linked to the promoter. In some embodiments the expression cassette further comprises a terminator, such as for example a terminator as disclosed herein having at least 80%, at least 85%, 90%, 95%, 96%, 97%, 98%, or 99% identity to at least 200, at least 300, or at least 400 contiguous nucleotides of a sequence selected from the group consisting of SEQ ID NO:7, SEQ ID NO:9, SEQ ID NO:12, SEQ ID NO:14, SEQ ID NO:16, SEQ ID NO:18, SEQ ID NO:20, SEQ ID NO:22, and SEQ ID NO:24, operably linked to the heterologous gene. In some embodiments, the heterologous gene encodes a polypeptide, such as but not limited to a polypeptide associated with lipid biosynthesis, a lipase, a polypeptide that participates in photosynthesis, a polypeptide associated with carbon fixation, a metabolic enzyme, a transporter protein, a dehydrogenase, a transcription factor, a transcriptional activator, a kinase, a phosphatase, a polypeptide involved in protein synthesis, or a cell signaling protein. In some embodiments, the heterologous gene is a reporter gene (e.g., a fluorescent protein or signal-generating enzyme such as a luciferase) or a selectable marker gene the encodes a polypeptide conferring resistance to an antibiotic, herbicide, or toxin, or a polypeptide that allows growth of an otherwise auxotrophic cell on restrictive media. In various embodiments, a gene encoding a polypeptide in an expression cassette as provided herein can be intronylated, i.e., can be engineered to include one or more introns that do not naturally occur in the gene that encodes the polypeptide. In various embodiments the engineered gene can include two, three, four, five, six, seven, eight, nine, or more than nine heterologous introns, such as but not limited to any disclosed herein. In some embodiments, the engineered gene is operably linked to a heterologous promoter that is derived from a species of interest and includes two or more, three or more, four or more, five or more heterologous introns derived from the same species of interest. In some embodiments, the two, three, four, or five or more heterologous introns engineered into a gene are derived from the same gene that is the source of the heterologous promoter that is operably linked to the gene. The expression cassette that includes an engineered gene that includes two, three, four, five, or more heterologous introns and that is operably linked to a heterologous promoter can further be operably linked to a heterologous terminator, such as but not limited to any disclosed herein. In some embodiments, the engineered gene is operably linked to a heterologous promoter and a heterologous terminator that are derived from a species of interest and includes two or more, three or more, four or more, five or more heterologous introns derived from the same species of interest. In some embodiments, the two, three, four, or five or more heterologous introns engineered into a gene are derived from the same gene that is the source of the heterologous promoter and heterologous terminator that are operably linked to the engineered gene. In any of the embodiments of an expression cassette or engineered gene, the gene can optionally be codon-optimized for expression in the species of interest.

In some embodiments an expression cassette as provided herein includes an engineered gene that includes a heterologous intron having at least 80%, or at least 85%, 90%, 95%, 96%, 97%, 98%, or 99% identity to SEQ ID NO:25, a heterologous intron having at least 80%, or at least 85%, 90%, 95%, 96%, 97%, 98%, or 99% identity to SEQ ID NO:26, a heterologous intron having at least 80%, or at least 85%, 90%, 95%, 96%, 97%, 98%, or 99% identity to SEQ ID NO:27, a heterologous intron having at least 80%, or at least 85%, 90%, 95%, 96%, 97%, 98%, or 99% identity to SEQ ID NO:28, and a heterologous intron having at least 80%, or at least 85%, 90%, 95%, 96%, 97%, 98%, or 99% identity to SEQ ID NO:29. In some embodiments the engineered gene can be operably a promoter from a *Parachlorella* species, and can optionally be operably linked to a promoter having at least 80%, or at least 85%, 90%, 95%, 96%, 97%, 98%, or 99% identity to at least 100, at least 200, at least 300, at least 400, at least 500, or between 500 and 530 contiguous nucleotides from the 3' end of SEQ ID NO:1. The engineered gene can optionally further be operable linked to a terminator from a *Parachlorella* species, such as but not limited to any disclosed herein and can optionally be operably linked to a terminator comprising at least 100 contiguous nucleotides of SEQ ID NO:7.

In some embodiments an expression cassette as provided herein can include an engineered gene that includes at least five heterologous introns selected from the group consisting of: a heterologous intron having at least 80%, or at least 85%, 90%, 95%, 96%, 97%, 98%, or 99% identity to SEQ ID NO:35; a heterologous intron having at least 80%, or at least 85%, 90%, 95%, 96%, 97%, 98%, or 99% identity to SEQ ID NO:36; a heterologous intron having at least 80%, or at least 85%, 90%, 95%, 96%, 97%, 98%, or 99% identity to SEQ ID NO:37; a heterologous intron having at least 80%, or at least 85%, 90%, 95%, 96%, 97%, 98%, or 99% identity to SEQ ID NO:38; a heterologous intron having at least 80%, or at least 85%, 90%, 95%, 96%, 97%, 98%, or 99% identity to SEQ ID NO:39; a heterologous intron having at least 80%, or at least 85%, 90%, 95%, 96%, 97%, 98%, or 99% identity to SEQ ID NO:40; a heterologous intron having at least 80%, or at least 85%, 90%, 95%, 96%, 97%, 98%, or 99% identity to SEQ ID NO:41; a heterologous intron having at least 80%, or at least 85%, 90%, 95%, 96%, 97%, 98%, or 99% identity to SEQ ID NO:42; and a heterologous intron having at least 80%, or at least 85%, 90%, 95%, 96%, 97%, 98%, or 99% identity to SEQ ID NO:43. In some embodiments the engineered gene can be operably linked to a promoter from a *Parachlorella* species, and can optionally be operably linked to a promoter having at least 80%, or at least 85%, 90%, 95%, 96%, 97%, 98%, or 99% identity to at least 100, at least 200, at least 300, at least 400, at least 500, or between 500 and 530 contiguous nucleotides from the 3' end of SEQ ID NO:13. The engineered gene can optionally further be operably linked to a terminator from a *Parachlorella* species, such as but not limited to any disclosed herein, and can optionally be operably linked to a terminator comprising at least 100 contiguous nucleotides of SEQ ID NO:14.

In some alternative embodiments, an expression cassette as provided herein can include a promoter such as any disclosed herein operably linked to a heterologous gene that encodes a functional RNA, such as for example a functional RNA selected from the group consisting of an antisense sequence, an RNAi molecule, a micro RNA, a shRNA, an siRNA, a gRNA, and a ribozyme. The expression cassette can optionally further include a terminator, such as but not limited to any disclosed herein.

In some aspects, the disclosure provides a vector comprising an expression cassette as disclosed herein and one or both of an autonomous replication sequence and a selectable marker gene. In some embodiments, the vector includes at least one origin of replication. In some embodiments, the vector further comprises an additional promoter, such as but not limited to a promoter as disclosed herein, operably linked to the selectable marker or reporter gene. In some embodiments, a selectable marker gene is selected from the group consisting of a gene conferring resistance to an antibiotic (e.g., tetracycline, doxycyclin, or analogs thereof, puromycin, hygromycin, blasticidin, bleomycin or phleomycin (Zeocin™), nourseothricin), a gene conferring resistance to an herbicide, a gene encoding acetyl CoA carboxylase (ACCase), a gene encoding acetohydroxy acid synthase (ahas), a gene encoding acetolactate synthase, a gene encoding aminoglycoside phosphotransferase, a gene encoding anthranilate synthase, a gene encoding bromoxynil nitrilase, a gene encoding cytochrome P450-NADH-cytochrome P450 oxidoreductase, a gene encoding dalapon dehalogenase, a gene encoding dihydropteroate synthase, a gene encoding a class I 5-enolpyruvylshikimate-3-phosphate synthase (EPSPS), a gene encoding a class II EPSPS (aroA), a gene encoding a non-class I/II EPSPS, a gene encoding glutathione reductase, a gene encoding glyphosate acetyltransferase, a gene encoding glyphosate oxidoreductase, a gene encoding hydroxyphenylpyruvate dehydrogenase, a gene encoding hydroxy-phenylpyruvate dioxygenase, a gene encoding isoprenyl pyrophosphate isomerase, a gene encoding lycopene cyclase, a gene encoding phosphinothricin acetyl transferase, a gene encoding phytoene desaturase, a gene encoding prenyl transferase, a gene encoding protoporphyrin oxidase, a gene encoding superoxide dismutase, arg7, his3, hisD, hisG, manA, nitl, trpB, uidA, xylA, a dihydrofolate reductase gene, a mannose-6-phosphate isomerase gene, a nitrate reductase gene, an ornithine decarboxylase gene, a thymidine kinase gene, a 2-deoxyglucose resistance gene, or an R-locus gene. A detectable marker gene can be, for example, a tyrosinase gene, lacZ, an alkaline phosphatase gene, an α-amylase gene, a horseradish peroxidase gene, an α-galactosidase gene, a luciferin/luciferase gene, a beta-glucuronidase gene (GUS), or a gene encoding a fluorescent protein.

In further aspects, the disclosure provides a method for transforming a eukaryotic cell comprising: introducing a vector such as a vector as disclosed herein into the eukaryotic cell; and selecting for a transformed eukaryotic cell. In some embodiments, the vector is introduced by electroporation. In some embodiments, the field strength is between about 250 kV/m and about 800 kV/m. For example, the field strength can be between about 500 kV/m and about 750 kV/m. In some embodiments, the field strength is between about 500 kV/m and about 600 kV/m. Alternatively, the resistance can be between about 100 Ohms and about 400 Ohms, for example, between about 200 Ohms and about 400 Ohms. In some embodiments, the resistance is between about 200 Ohms and about 300 Ohms. In some embodiments, the capacitance is between about 10 μF and about 50 μF for example between about 25 μF and about 50 μF. The eukaryotic cell can be an algal cell, for example, a Chlorophyte algal cell, and can be a cell of an alga belonging to the Trebouxiophyceae class, for example, an algal call of a species of a genus such as *Botryococcus, Chlorella, Auxenochlorella, Heveochlorella, Marinichlorella, Parachlorella, Pseudochlorella, Tetrachlorella, Eremosphaera, Franceia, Micractinium, Nannochloris, Oocystis, Picochlorum,* or *Prototheca*. In some embodiments, the methods are used to transform an algal species belonging to a genus such as *Auxenochlorella, Chlorella, Heveochlorella, Marinichlorella, Parachlorella, Pseudochlorella* or *Tetrachlorella*. In further embodiments, the vector is introduced by a biolistic procedure. In some embodiments, about 300 psi or more of pressure is used to impel biolistic microcarriers coated with vector DNA into the eukaryotic cell.

Yet another aspect of the invention is a eukaryotic host cell comprising a nucleic acid molecule that includes an engineered gene that includes at least five heterologous introns. The engineered gene can be a gene not derived from the same genus as the eukaryotic host cell, or can be a gene not derived from the same species as the eukaryotic host cell. In various embodiments the at least five heterologous introns are derived from introns of the genus or species of the eukaryotic host cell. In some embodiments, the nucleic acid molecule comprises a promoter operably linked to the engineered gene. The promoter can be a promoter derived from an organism of the same genus or species as the eukaryotic host cell. Further, the nucleic acid molecule can include a terminator sequence, where the terminator sequence can optionally be derived from an organism of the same genus or same species as the eukaryotic host cell. A eukaryotic host cell as provided herein that includes a recombinant nucleic acid molecule that includes a gene that includes at least five heterologous introns can exhibit a higher level of expression of the engineered gene than is demonstrated by a control eukaryotic host cell that comprises a nucleic acid molecule comprising an otherwise identical gene that is does not include at least five heterologous introns. The at least five heterologous introns can be derived from a gene of an organism of the same genus or species as the eukaryotic host cell, and in various embodiments, the engineered gene is operably linked to a heterologous promoter which is derived from a gene of the same genus or species as the eukaryotic host cell. Further, the engineered gene can be operably linked to a heterologous terminator sequence which can be derived from a gene of the same genus or species as the eukaryotic host cell. In particular embodiments, the engineered gene of the eukaryotic host cell includes at least five heterologous introns that are all derived from the same gene, where the gene from with the introns are sourced is native to the host cell (i.e., of the same species), and the engineered gene is operably linked to a promoter and a terminator that are also both sourced form the same gene as the heterologous introns. The eukaryotic host cell can be a eukaryotic microorganism, and can be, for example, a heterokont or microalga. For example, the algal cell can be a Chlorophyte, Charyophyte, Eustigmatophyte, or Bacillariophyte alga. For example, the algal cell can be from a species selected from the group consisting of *Achnanthes, Amphiprora, Amphora, Ankistrodesmus, Asteromonas, Boekelovia, Bolidomonas, Borodinella, Botrydium, Botryococcus, Bracteococcus, Chaetoceros, Carteria, Chlamydomonas, Chlorococcum, Chlorogonium, Chlorella, Chroomonas, Chrysosphaera, Cricosphaera, Crypthecodinium, Cryptomonas, Cyclotella, Dunaliella, Ellipsoidon, Emiliania, Eremosphaera, Ernodesmius, Euglena, Eustigmatos, Franceia, Fragilaria, Gloeothamnion, Haematococcus, Halocafeteria, Heterosigma, Hymenomonas, Isochrysis, Lepocinclis, Micractinium, Monoraphidium, Nannochloris, Nannochloropsis, Navicula, Neochloris, Nephrochloris, Nephroselmis, Nitzschia, Ochromonas, Oedogonium, Oocystis, Ostreococcus, Pavlova, Parachlorella, Pascheria, Pelagomonas, Phaeodactylum, Phagus, Picochlorum, Platymonas, Pleurochrysis, Pleurococcus, Prototheca, Pseudochlorella, Pseudoneochloris, Pseudostaurastrum, Pyramimonas, Pyrobotrys, Scenedesmus, Schizochlamydella, Skeletonema, Spyrogyra, Stichococcus, Tetrachlorella, Tetraselmis, Thalassiosira, Tribonema, Vaucheria, Viridiella, Vischeria,* and *Volvox*. In some embodiments the eukaryotic host cell can be a Chlorophyte or Charyophyte microalga, and can be, for example, a Chlorophyte alga of the Chlorophyceae, the Trebouxiophyceae, the Chlorodendrophyceae, the Ulvophyceae, the Pedinophyceae, or the Prasinophyceae class. In some examples, the eukaryotic host cell is a Chlorophyte alga selected from the group consisting of *Asteromonas, Ankistrodesmus, Carteria, Chlamydomonas, Chlorococcum, Chlorogonium, Chrysosphaera, Desmodesmus, Dunaliella, Haematococcus, Monoraphidium, Neochloris, Oedogonium, Pelagomonas, Pleurococcus, Pyrobotrys, Scenedesmus, Volvox, Botryococcus, Chlorella, Eremosphaera, Franceia, Micractinium, Nannochloris, Oocystis, Parachlorella, Picochlorum, Prototheca, Pseudochlorella, Stichococcus, Viridiella, Prasinocladus, Scherffelia,* and *Tetraselmis*. In some embodiments, the algal cell is a chlorophyte algal cell of the Trebouxiophyceae class, such as, for example, a species of a genus such as *Actinastrum, Amphikorikos, Asterochloris,*

*Auxenochlorella, Botryococcus, Chlorella, Choricystis, Coccomyxa, Coenocystis, Closteriopsis, Diacanthos, Dicloster, Dictyosphaerium, Dictyochloropsis, Didymogenes, Diplosphaera, Eremosphaera, Franceia, Fusochloruis, Gloeotila, Helicosporidium, Heveochlorella, Koliella, Koriellopsis, Lagerheimia, Leptosira, Loboshpaera, Makinoella, Marvania, Muriella, Meyrella, Marinichlorella, Microthamnion, Micractinium, Myrmecia, Nannochloris, Oocystis, Pabia, Parachlorella, Paradoxia, Parietochloris, Picochlorum, Prasiola, Prasiococcus, Prasiolopsis, Prototheca, Pseudochlorella, Pseudotrebouxia, Raphidonema, Rosssenvingiella, Stichococcus, Tetrachlorella, Trebouxia, Trichophilus, Viridiella,* or *Watanabea.* In some embodiments, a eukaryotic host cell can be a species belonging to the genus of *Botryococcus, Chlorella, Eremosphaera, Franceia, Micractinium, Nannochloris, Oocystis, Parachlorella, Picochlorum, Prototheca,* or *Pseudochlorella.* In some aspects, the eukaryotic host cell can be a species belonging to the genus of *Auxenochlorella, Chlorella, Heveochlorella, Marinichlorella, Parachlorella, Pseudochlorella* or *Tetrachlorella.* For example, a cell used in the methods provided herein or that comprises a nucleic acid molecule, engineered gene, expression cassette, or vector as disclosed herein can optionally be a species of *Parachlorella,* such as non-limiting examples: *Parachlorella kessieri, P. hussii, P. beijerinckii, P.* sp. CCAP 206/1, or *P.* sp. pgu003.

In some embodiments the engineered host includes an engineered gene that includes a heterologous intron having at least 80%, or at least 85%, 90%, 95%, 96%, 97%, 98%, or 99% identity to SEQ ID NO:25, a heterologous intron having at least 80%, or at least 85%, 90%, 95%, 96%, 97%, 98%, or 99% identity to SEQ ID NO:26, a heterologous intron having at least 80%, or at least 85%, 90%, 95%, 96%, 97%, 98%, or 99% identity to SEQ ID NO:27, a heterologous intron having at least 80%, or at least 85%, 90%, 95%, 96%, 97%, 98%, or 99% identity to SEQ ID NO:28, and a heterologous intron having at least 80%, or at least 85%, 90%, 95%, 96%, 97%, 98%, or 99% identity to SEQ ID NO:29. In some embodiments the engineered gene can be operably linked to a promoter having at least 80%, or at least 85%, 90%, 95%, 96%, 97%, 98%, or 99% identity to at least 100, at least 200, at least 300, at least 400, at least 500, or between 500 and 530 contiguous nucleotides from the 3' end of SEQ ID NO:1. The engineered gene can optionally further be operable linked to a terminator comprising at least 100 contiguous nucleotides of SEQ ID NO:7.

In alternative embodiments the engineered host can include an engineered gene that includes at least five heterologous introns selected from the group consisting of: a heterologous intron having at least 80%, or at least 85%, 90%, 95%, 96%, 97%, 98%, or 99% identity to SEQ ID NO:35; a heterologous intron having at least 80%, or at least 85%, 90%, 95%, 96%, 97%, 98%, or 99% identity to SEQ ID NO:36; a heterologous intron having at least 80%, or at least 85%, 90%, 95%, 96%, 97%, 98%, or 99% identity to SEQ ID NO:37; a heterologous intron having at least 80%, or at least 85%, 90%, 95%, 96%, 97%, 98%, or 99% identity to SEQ ID NO:38; a heterologous intron having at least 80%, or at least 85%, 90%, 95%, 96%, 97%, 98%, or 99% identity to SEQ ID NO:39; a heterologous intron having at least 80%, or at least 85%, 90%, 95%, 96%, 97%, 98%, or 99% identity to SEQ ID NO:40; a heterologous intron having at least 80%, or at least 85%, 90%, 95%, 96%, 97%, 98%, or 99% identity to SEQ ID NO:41; a heterologous intron having at least 80%, or at least 85%, 90%, 95%, 96%, 97%, 98%, or 99% identity to SEQ ID NO:42; and a heterologous intron having at least 80%, or at least 85%, 90%, 95%, 96%, 97%, 98%, or 99% identity to SEQ ID NO:43. In some exemplary embodiments the engineered gene can be operably linked to a promoter having at least 80%, or at least 85%, 90%, 95%, 96%, 97%, 98%, or 99% identity to at least 100, at least 200, at least 300, at least 400, at least 500, or between 500 and 530 contiguous nucleotides from the 3' end of SEQ ID NO:13. The engineered gene can optionally further be operably linked to a terminator comprising at least 100 contiguous nucleotides of SEQ ID NO:14.

Yet another aspect of the invention is a method of expressing an exogenous gene in a recombinant eukaryotic microorganism comprising introducing a nucleic acid molecule that includes an engineered gene into the recombinant eukaryotic microorganism, where the engineered gene comprises at least three heterologous introns, and culturing the eukaryotic microorganism under conditions in which the eukaryotic microorganism expresses the engineered gene. For example, the engineered gene can include at least three heterologous introns that are derived from a gene of the same species as the eukaryotic microorganism. In various embodiments the eukaryotic microorganism exhibits higher expression of the engineered gene than is exhibited by a control eukaryotic microorganism that includes an otherwise identical gene that does not include the at least three heterologous introns. The engineered gene can be operably linked to a promoter derived from a gene of the host microorganism. The engineered gene can additionally be operably linked to a terminator derived from a gene of the host microorganism. In some examples the engineered gene includes at least four heterologous introns or at least five heterologous introns. The at least three, at least four, or at least five introns can all be derived from the same gene. The microorganism can be a heterokont or alga, and in some embodiments is a chlorophyte alga, or example, a chlorophyte alga of the Chlorophyceae, the Trebouxiophyceae, the Chlorodendrophyceae, the Ulvophyceae, the Pedinophyceae, or the Prasinophyceae class, such as any disclosed herein. In some examples, the eukaryotic host cell is a chlorophyte alga selected from the group consisting of *Chlorella, Parachlorella, Pseudochlorella, Auxenochlorella, Heveochlorella, Marinichlorella,* or *Tetrachlorella.*

BRIEF DESCRIPTION OF THE DRAWINGS

The drawings described herein are for illustrative purposes only of selected embodiments and not all possible implementations, and are not intended to limit the scope of the present disclosure.

DETAILED DESCRIPTION

Figure 1:
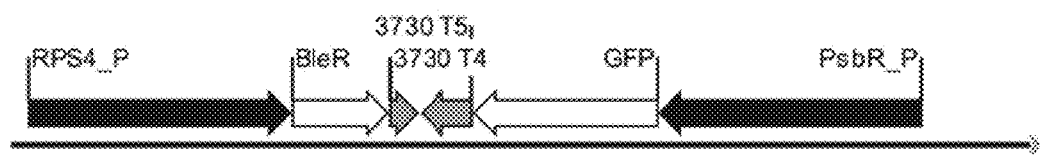
FIG. 1 is a diagram of plasmid pSGE6450 harboring a bleomycin R expression cassette that includes a blecomycin resistance gene (BleR, SEQ ID NO:2) operably linked to the RPS4 promoter (SEQ ID NO:1) and the *Nannochloropsis gaditana* T4 terminator (SEQ ID NO:3) which generated one transformant when transformed into WT-1185 (*Parachlorella* sp.). Promoters are shown in black, open reading frames for genes in white, and terminators in gray.

All headings are for the convenience of the reader and do not limit the invention in any way. As used herein, the terms "aspect" and "embodiment" do not necessarily imply mutually exclusive features and/or combinations of the invention and do not limit this disclosure in any way.

The present disclosure generally relates to compositions, methods and related materials for use in genetic engineering of organisms. In particular, the disclosure provides methods and materials useful for affecting gene expression in vivo and/or in vitro. Some embodiments disclosed herein relate to isolated, recombinant, or synthetic nucleic acid molecules having transcriptional regulatory activity such as, for example, regulatory elements. Some embodiments disclosed herein relate to methods for modifying, making, and using such regulatory elements. Some embodiments disclosed herein relate to recombinant cells, methods for making and using the same, and biomaterials derived therefrom.

In the following detailed description, reference is made to the accompanying drawings, which form a part hereof. In the drawings, similar symbols typically identify similar components, unless context dictates otherwise. The illustrative embodiments described in the detailed description, drawings, and claims are not meant to be limiting. Other embodiments may be used, and other changes may be made, without departing from the spirit or scope of the subject matter presented here. It will be readily understood that the aspects of the present disclosure, as generally described herein, and illustrated in the Figures, can be arranged, substituted, combined, and designed in a wide variety of Some Definitions Unless otherwise defined, all terms of art, notations and other scientific terms or terminology used herein are intended to have the meanings commonly understood by those of skill in the art to which this disclosure pertains. In some cases, terms with commonly understood meanings are defined herein for clarity and/or for ready reference, and the inclusion of such definitions herein should not necessarily be construed to represent a substantial difference over what is generally understood in the art. Many of the techniques and procedures described or referenced herein are well understood and commonly employed using conventional methodology by those skilled in the art.

The singular form "a", "an", and "the" include plural references unless the context clearly dictates otherwise. For example, the term "a molecule" includes one or more molecules, including mixtures thereof. "A and/or B" is used herein to include all of the following alternatives: "A", "B", and "A and B".

As used herein, the terms "about" or "approximately" when referring to any numerical value are intended to mean a value of plus or minus 10% of the stated value. For example, "about 50 degrees C." (or "approximately 50 degrees C.") encompasses a range of temperatures from 45 degrees C. to 55 degrees C., inclusive. Similarly, "about 100 mM" (or "approximately 100 mM") encompasses a range of concentrations from 90 mM to 110 mM, inclusive. Alternatively, "about" or "approximately" can mean within 5% of the stated value, or in some cases within 2.5% of the stated value, or, "about" can mean rounded to the nearest significant digit. All ranges provided within the application are inclusive of the values of the upper and lower ends of the range.

The terms, "cells", "cell cultures", "cell line", "recombinant host cells", "recipient cells" and "host cells" as used herein, include the primary subject cells and any progeny thereof, without regard to the number of transfers. It should be understood that not all progeny are exactly identical to the parental cell (due to deliberate or inadvertent mutations or differences in environment); however, such altered progeny are included in these terms, so long as the progeny retain the same functionality as that of the originally transformed cell.

As used herein, the term "construct" is intended to mean any recombinant nucleic acid molecule such as an expression cassette, plasmid, cosmid, virus, autonomously replicating polynucleotide molecule, phage, or linear or circular, single-stranded or double-stranded, DNA or RNA polynucleotide molecule, derived from any source, capable of genomic integration or autonomous replication, comprising a nucleic acid molecule where one or more nucleic acid sequences has been linked in a functionally operative manner, i.e. operably linked.

A "control organism", "control microorganism", or "control cell" as used herein, refers to an organism, microorganism, or cell that is substantially identical to the subject organism, microorganism, or cell, except for the engineered genetic manipulation or introduced mutation disclosed for the subject organism, microorganism, or cell, and can provide a reference point for measuring changes in phenotype of the subject organism or cell. "Substantially identical" thus includes, for example, small random variations in genome sequence ("SNPs") that are not relevant to the genotype, phenotype, parameter, or gene expression level that is of interest in the subject microorganism. Depending on specific purposes of their use, a control organism or cell may comprise, for example, (a) a progenitor strain or species, cell or microorganism population, or organism, with respect to the subject organism, microorganism, or cell, where the progenitor lacks the genetically engineered constructs or alterations that were introduced into the progenitor strain, species, organism, or cell or microorganism population to generate the subject organism, microorganism, or cell; b) a wild-type organism or cell, i.e., of the same genotype as the starting material for the genetic alteration which resulted in the subject organism or cell; (c) an organism or cell of the same genotype as the starting material but which has been transformed with a null construct (i.e. a construct which has no known effect on the trait of interest, such as a construct comprising a reporter gene); (d) an organism or cell which is a non-transformed segregant among progeny of a subject organism, microorganism, or cell; or (e) the subject organism or cell itself, under conditions in which the gene of interest is not expressed. In some instances, "control organism" may refer to an organism that does not contain the exogenous nucleic acid present in the transgenic organism of interest, but otherwise has the same or very similar genetic background as such a transgenic organism.

As used herein, "mutant" refers to an organism that has a mutation in a gene that is the result of classical mutagenesis, for example, using gamma irradiation, UV, or chemical mutagens. "Mutant" as used herein also refers to a recombinant cell that has altered structure or expression of a gene as a result of genetic engineering that many include, as non-limiting examples, overexpression, including expression of a gene under different temporal, biological, or environmental regulation and/or to a different degree than occurs naturally and/or expression of a gene that is not naturally expressed in the recombinant cell; homologous recombination, including knock-outs and knock-ins (for example, gene replacement with genes encoding polypeptides having greater or lesser activity than the wild type polypeptide, and/or dominant negative polypeptides); gene attenuation via RNAi, antisense RNA, or ribozymes, or the like; and genome engineering using meganucleases, TAL-ENs, and/or CRISPR technologies, and the like.

As used herein, "exogenous" with respect to a nucleic acid or gene indicates that the nucleic or gene has been introduced ("transformed") into an organism, microorganism, or cell by human intervention. Typically, such an exogenous nucleic acid is introduced into a cell or organism via a recombinant nucleic acid construct. An exogenous nucleic acid can be a sequence from one species introduced into another species, i.e., a heterologous nucleic acid. An exogenous nucleic acid can also be a sequence that is homologous to an organism (i.e., the nucleic acid sequence occurs naturally in that species or encodes a polypeptide that occurs naturally in the host species) that has been isolated, optionally modified, and subsequently reintroduced into cells of that organism. An exogenous nucleic acid that includes a homologous sequence can often be distinguished from the naturally-occurring sequence by detection of any introduced modifications and/or the presence of non-natural sequences linked to the exogenous nucleic acid, e.g., non-native regulatory sequences flanking the homologous gene sequence in a recombinant nucleic acid construct. Alternatively or in addition, a stably transformed exogenous nucleic acid can be detected and/or distinguished from a native gene by its juxtaposition to sequences in the genome where it has integrated. Further, a nucleic acid is considered exogenous if it has been introduced into a progenitor of the cell, organism, or strain under consideration.

The term "expression cassette" as used herein, refers to a nucleic acid construct that encodes a protein or functional RNA operably linked to expression control elements, such as a promoter, and optionally, any or a combination of other nucleic acid sequences that affect the transcription or translation of the gene, such as, but not limited to, a transcriptional terminator, a ribosome binding site, a splice site or splicing recognition sequence, an intron, an enhancer, a polyadenylation signal, an internal ribosome entry site, etc.

A "functional RNA molecule" is an RNA molecule that can interact with one or more proteins or nucleic acid molecules to perform or participate in a structural, catalytic, or regulatory function that affects the expression or activity of a gene or gene product other than the gene that produced the functional RNA. A functional RNA can be, for example, a transfer RNA (tRNA), ribosomal RNA (rRNA), anti-sense RNA (asRNA), microRNA (miRNA), short-hairpin RNA (shRNA), small interfering RNA (siRNA), a guide RNA (gRNA), crispr RNA (crRNA), or transactivating RNA (tracrRNA) of a CRISPR system, small nucleolar RNAs (snoRNAs), piwi-interacting RNA (piRNA), or a ribozyme.

The term "gene" is used broadly to refer to any segment of a nucleic acid molecule (typically DNA, but optionally RNA) encoding a polypeptide or expressed RNA. Thus, genes include sequences encoding expressed RNA (which can include polypeptide coding sequences or, for example, functional RNAs, such as ribosomal RNAs, tRNAs, antisense RNAs, microRNAs, short hairpin RNAs, gRNAs, crRNAs, tracrRNAs, ribozymes, etc.). Genes may further comprise regulatory sequences required for or affecting their expression, as well as sequences associated with the protein or RNA-encoding sequence in its natural state, such as, for example, intron sequences, 5' or 3' untranslated sequences, etc. In some examples, a gene may only refer to a protein-encoding portion of a DNA or RNA molecule, which may or may not include introns. A gene is preferably greater than 50 nucleotides in length, more preferably greater than 100 nucleotide in length, and can be, for example, between 50 nucleotides and 500,000 nucleotides in length, such as between 100 nucleotides and 100,000 nucleotides in length or between about 200 nucleotides and about 50,000 nucleotides in length, or about 200 nucleotides and about 20,000 nucleotides in length. Genes can be obtained from a variety of sources, including cloning from a source of interest or synthesizing from known or predicted sequence information.

The term "nucleic acid" or "nucleic acid molecule" refers to, a segment of DNA or RNA (e.g., mRNA), and also includes nucleic acids having modified backbones (e.g., peptide nucleic acids, locked nucleic acids) or modified or non-naturally-occurring nucleobases. The nucleic acid molecules can be double-stranded or single-stranded; a single stranded nucleic acid that comprises a gene or a portion thereof can be a coding (sense) strand or a non-coding (antisense) strand.

The terms "coding sequence" or "coding region" or "amino acid-encoding sequences" as used herein, refer to regions of a nucleic acid sequence which can be transcribed to produce a functional RNA or an RNA transcript that can be translated into a polypeptide when placed under the control of appropriate expression control sequences and in the presence of appropriate cellular machinery or enzymes. The term "non-coding sequence" or "non-coding region" refers to regions of a nucleic acid sequence that are not transcribed and translated into amino acids (e.g., introns, untranslated regions, etc.) or are not transcribed or do not form at least a portion of a mature functional RNA sequence.

As used herein, the term "protein" or "polypeptide" is intended to encompass a singular "polypeptide" as well as plural "polypeptides," and refers to a molecule composed of monomers (amino acids) linearly linked by amide bonds (also known as peptide bonds). The term "polypeptide" refers to any chain or chains of two or more amino acids, and does not refer to a specific length of the product. Thus, peptides, dipeptides, tripeptides, oligopeptides, "protein," "amino acid chain," or any other term used to refer to a chain or chains of two or more amino acids, are included within the definition of "polypeptide," and the term "polypeptide" can be used instead of, or interchangeably with any of these terms.

A nucleic acid molecule may be "derived from" an indicated source, which includes the isolation (in whole or in part) of a nucleic acid segment from an indicated source. A nucleic acid molecule may also be derived from an indicated source by, for example, direct cloning, PCR amplification, or artificial synthesis from the indicated polynucleotide source or based on a sequence associated with the indicated polynucleotide source. Genes or nucleic acid molecules derived from a particular source or species also include genes or nucleic acid molecules having sequence modifications with respect to the source nucleic acid molecules. For example, a gene or nucleic acid molecule derived from a source (e.g., a particular referenced gene) can include one or more mutations with respect to the source gene or nucleic acid molecule that are unintended or that are deliberately introduced, and if one or more mutations, including substitutions, deletions, or insertions, are deliberately introduced the sequence alterations can be introduced by random or targeted mutation of cells or nucleic acids, by amplification or other molecular biology techniques, or by chemical synthesis, or any combination thereof. A gene or nucleic acid molecule that is derived from a referenced gene or nucleic acid molecule that encodes a functional RNA or polypeptide can encode a functional RNA or polypeptide having at least 75%, at least 80%, at least 85%, at least 90%, or at least 95%, sequence identity with the referenced or source functional RNA or polypeptide, or to a functional fragment thereof. For example, a gene or nucleic acid molecule that is derived from a referenced gene or nucleic acid molecule that encodes a functional RNA or polypeptide can encode a functional RNA or polypeptide having at least 85%, at least 90%, at least 95%, at least 96%, at least 97%, at least 98%, or at least 99% sequence identity with the referenced or source functional RNA or polypeptide, or to a functional fragment thereof. A gene may also be disclosed as encoding a polypeptide derived from an indicated source. For example, the amino acid sequence of a polypeptide encoded by a gene as disclosed herein may be an amino acid sequence of a polypeptide from a first organism other than a host organism, and the gene or polypeptide may be referred to as being derived from that organism, even if the gene has been codon-optimized for expression in the second (host) organism.

As used herein, an "isolated" nucleic acid or protein is removed from its natural milieu or the context in which the nucleic acid or protein exists in nature. For example, an isolated protein or nucleic acid molecule is removed from the cell or organism with which it is associated in its native or natural environment. An isolated nucleic acid or protein can be, in some instances, partially or substantially purified, but no particular level of purification is required for isolation. Thus, for example, an isolated nucleic acid molecule can be a nucleic acid sequence that has been excised from the chromosome, genome, or episome that it is integrated into in nature.

A "purified" nucleic acid molecule or nucleotide sequence, or protein or polypeptide sequence, is substantially free of cellular material and cellular components. The purified nucleic acid molecule or protein may be free of chemicals beyond buffer or solvent, for example "Substantially free" is not intended to mean that other components beyond the novel nucleic acid molecules are undetectable.

The terms "naturally-occurring" and "wild type" refer to a form found in nature. For example, a naturally occurring or wild type nucleic acid molecule, nucleotide sequence or protein may be present in and isolated from a natural source, and is not intentionally modified by human manipulation.

As used herein, "expression" includes the expression of a gene at least at the level of RNA production, and an "expression product" includes the resultant product, e.g., a polypeptide or functional RNA (e.g., a ribosomal RNA, a tRNA, an antisense RNA, a micro RNA, an shRNA, a ribozyme, etc.), of an expressed gene. The term "increased expression" includes an alteration in gene expression to facilitate increased mRNA production and/or increased polypeptide expression. "Increased production", when referring to protein abundance or the abundance of active protein resulting from gene expression, protein turnover rates, protein activation states, and the like, includes an increase in the amount of polypeptide expression, in the level of the enzymatic activity of a polypeptide, or a combination of both, as compared to the native production or enzymatic activity of the polypeptide.

As used herein "attenuated" means reduced in amount, degree, intensity, or strength. Attenuated gene expression may refer to a significantly reduced amount and/or rate of transcription of the gene in question, or of translation, folding, or assembly of the encoded protein. As nonlimiting examples, an attenuated gene may be due to a mutation or a disruption in the gene (e.g., a gene disrupted by partial or total deletion, truncation, frameshifting, or insertional mutation) or may have decreased expression due to alteration, replacement, and/or elimination of one or more gene regulatory sequences. A mutant alga having attenuated expression of a gene can be a recombinant alga in which the attenuation is the result of genetic engineering, i.e., by human intervention that includes, typically, introduction of one or more non-native nucleic acid molecules or polypeptides into the alga. Alternatively, gene attenuation can be by classical mutagenesis according to protocols known in the art or adapted therefrom. An attenuated gene may also be a gene that is targeted by a "gene knockdown" construct, such as, for example, a construct encoding an antisense RNA, a microRNA, a short hairpin RNA, a guide RNA or transactivating RNA of a CRISPR system, or a ribozyme. In the case of both expression of transgenes and suppression of endogenous genes (e.g., by antisense or sense suppression) one of ordinary skill will recognize that the inserted polynucleotide sequence need not be identical, but may be only substantially identical to a sequence of the gene from which it was derived. As explained herein, these substantially identical variants are specifically covered by reference to a specific nucleic acid sequence.

"Exogenous nucleic acid molecule" or "exogenous gene" refers to a nucleic acid molecule or gene that has been introduced ("transformed") into a cell. A transformed cell may be referred to as a recombinant cell, into which additional exogenous gene(s) may be introduced. A descendent of a cell transformed with a nucleic acid molecule is also referred to as "transformed" if it has inherited the exogenous nucleic acid molecule. The exogenous gene may be from a different species (and so "heterologous"), or from the same species (and so "homologous"), relative to the cell being transformed. An "endogenous" nucleic acid molecule, gene or protein is a native nucleic acid molecule, gene or protein as it occurs in, or is naturally produced by, the host.

Further, the term "exogenous" as used herein in the context of a gene or protein, refers to a gene or protein that is not derived from the host organism species.

The term "transgene" as used herein, refers to an exogenous gene, that is, a gene introduced into a microorganism or a progenitor by human intervention.

The term "ortholog" of a gene or protein as used herein refers to its functional equivalent in another species.

Gene and protein Accession numbers, commonly provided herein in parenthesis after a gene or species name, are unique identifiers for a sequence record publicly available at the National Center for Biotechnology Information (NCBI) website (ncbi.nlm.nih.gov) maintained by the United States National Institutes of Health. The "GenInfo Identifier" (GI) sequence identification number is specific to a nucleotide or amino acid sequence. If a sequence changes in any way, a new GI number is assigned. A Sequence Revision History tool is available to track the various GI numbers, version numbers, and update dates for sequences that appear in a specific GenBank record. Searching and obtaining nucleic acid or gene sequences or protein sequences based on Accession numbers and GI numbers is well known in the arts of, e.g., cell biology, biochemistry, molecular biology, and molecular genetics.

As used herein, the terms "percent identity" or "homology" with respect to nucleic acid or polypeptide sequences are defined as the percentage of nucleotide or amino acid residues in the candidate sequence that are identical with the known polypeptides, after aligning the sequences for maximum percent identity and introducing gaps, if necessary, to achieve the maximum percent homology. N-terminal or C-terminal insertion or deletions shall not be construed as affecting homology, and internal deletions and/or insertions into the polypeptide sequence of less than about 30, less than about 20, or less than about 10 amino acid residues shall not be construed as affecting homology. Homology or identity at the nucleotide or amino acid sequence level can be determined by BLAST (Basic Local Alignment Search Tool) analysis using the algorithm employed by the programs blastp, blastn, blastx, tblastn, and tblastx (Altschul (1997), Nucleic Acids Res. 25, 3389-3402, and Karlin (1990), Proc. Natl. Acad. Sci. USA 87, 2264-2268), which are tailored for sequence similarity searching. The approach used by the BLAST program is to first consider similar segments, with and without gaps, between a query sequence and a database sequence, then to evaluate the statistical significance of all matches that are identified, and finally to summarize only those matches which satisfy a preselected threshold of significance. For a discussion of basic issues in similarity searching of sequence databases, see Altschul (1994), Nature Genetics 6, 119-129. The search parameters for histogram, descriptions, alignments, expect (i.e., the statistical significance threshold for reporting matches against database sequences), cutoff, matrix, and filter (low complexity) can be at the default settings. The default scoring matrix used by blastp, blastx, tblastn, and tblastx is the BLOSUM62 matrix (Henikoff (1992), Proc. Natl. Acad. Sci. USA 89, 10915-10919), recommended for query sequences over 85 in length (nucleotide bases or amino acids).

For blastn, designed for comparing nucleotide sequences, the scoring matrix is set by the ratios of M (i.e., the reward score for a pair of matching residues) to N (i.e., the penalty score for mismatching residues), wherein the default values for M and N can be +5 and −4, respectively. Four blastn parameters can be adjusted as follows: Q=10 (gap creation penalty); R=10 (gap extension penalty); wink=1 (generates word hits at every winkth position along the query); and gapw=16 (sets the window width within which gapped alignments are generated). The equivalent Blastp parameter settings for comparison of amino acid sequences can be: Q=9; R=2; wink=1; and gapw=32. A Bestfit comparison between sequences, available in the GCG package version 10.0, can use DNA parameters GAP=50 (gap creation penalty) and LEN=3 (gap extension penalty), and the equivalent settings in protein comparisons can be GAP=8 and LEN=2.

Thus, when referring to the polypeptide or nucleic acid sequences of the present disclosure, included are sequence identities of at least 40%, at least 45%, at least 50%, at least 55%, of at least 70%, at least 65%, at least 70%, at least 75%, at least 80%, or at least 85%, for example at least 86%, at least 87%, at least 88%, at least 89%, at least 90%, at least 91%, at least 92%, at least 93%, at least 94%, at least 95%, at least 96%, at least 97%, at least 98%, at least 99%, or about 100% sequence identity with the full-length polypeptide or nucleic acid sequence, or to fragments thereof comprising a consecutive sequence of at least 100, at least 125, at least 150 or more amino acid residues of the entire protein; variants of such sequences, e.g., wherein at least one amino acid residue has been inserted N- and/or C-terminal to, and/or within, the disclosed sequence(s) which contain(s) the insertion and substitution. Contemplated variants can additionally or alternately include those containing predetermined mutations by, e.g., homologous recombination or site-directed or PCR mutagenesis, and the corresponding polypeptides or nucleic acids of other species, including, but not limited to, those described herein, the alleles or other naturally occurring variants of the family of polypeptides or nucleic acids which contain an insertion and substitution; and/or derivatives wherein the polypeptide has been covalently modified by substitution, chemical, enzymatic, or other appropriate means with a moiety other than a naturally occurring amino acid which contains the insertion and substitution (for example, a detectable moiety such as an enzyme).

The term "native" is used herein to refer to nucleic acid sequences or amino acid sequences as they naturally occur in the host. The term "non-native" is used herein to refer to nucleic acid sequences or amino acid sequences that do not occur naturally in the host. A nucleic acid sequence or amino acid sequence that has been removed from a cell, subjected to laboratory manipulation, and introduced or reintroduced into a host cell is considered "non-native." Synthetic or partially synthetic genes introduced into a host cell are "non-native." Non-native genes further include genes endogenous to the host alga operably linked to one or more heterologous regulatory sequences that have been recombined into the host genome.

A "recombinant" or "engineered" nucleic acid molecule is a nucleic acid molecule that has been altered through human manipulation. As non-limiting examples, a recombinant nucleic acid molecule includes any nucleic acid molecule that: 1) has been partially or fully synthesized or modified in vitro, for example, using chemical or enzymatic techniques (e.g., by use of chemical nucleic acid synthesis, or by use of enzymes for the replication, polymerization, digestion (exonucleolytic or endonucleolytic), ligation, reverse transcription, transcription, base modification (including, e.g., methylation), integration or recombination (including homologous and site-specific recombination) of nucleic acid molecules); 2) includes conjoined nucleotide sequences that are not conjoined in nature, 3) has been engineered using molecular cloning techniques such that it lacks one or more nucleotides with respect to the naturally occurring nucleic acid molecule sequence, and/or 4) has been manipulated using molecular cloning techniques such that it has one or more sequence changes or rearrangements with respect to the naturally occurring nucleic acid sequence. As non-limiting examples, a cDNA is a recombinant DNA molecule, as is any nucleic acid molecule that has been generated by in vitro polymerase reaction(s), or to which linkers have been attached, or that has been integrated into a vector, such as a cloning vector or expression vector.

The term "recombinant protein" as used herein refers to a protein produced by genetic engineering.

When applied to organisms, the term recombinant, engineered, or genetically engineered refers to organisms that have been manipulated by introduction of a heterologous or exogenous (e.g., non-native) recombinant nucleic acid sequence into the organism, and includes, without limitation, gene knockouts, targeted mutations, and gene replacement, promoter replacement, deletion, or insertion, or transfer of a nucleic acid molecule, e.g., a transgene, synthetic gene, promoter, or other sequence into the organism. Recombinant or genetically engineered organisms can also be organisms into which constructs for gene "knock down" have been introduced. Such constructs include, but are not limited to, one or more guide RNAs, RNAi, microRNA, shRNA, siRNA, antisense, and ribozyme constructs. Also included are organisms whose genomes have been altered by the activity of cas nucleases, meganucleases, or zinc finger nucleases. An exogenous or recombinant nucleic acid molecule can be integrated into the recombinant/genetically engineered organism's genome or in other instances are not integrated into the recombinant/genetically engineered organism's genome. As used herein, "recombinant alga" or "recombinant host cell" includes progeny or derivatives of the recombinant algae of the disclosure. Because certain modifications may occur in succeeding generations due to either mutation or environmental influences, such progeny or derivatives may not, in fact, be identical to the parent cell, but are still included within the scope of the term as used herein.

The term "heterologous" when used in reference to a polynucleotide, a gene, a nucleic acid, a polypeptide, or an enzyme, refers to a polynucleotide, gene, a nucleic acid, polypeptide, or an enzyme that is not derived from the host species. For example, "heterologous gene" or "heterologous nucleic acid sequence" as used herein, refers to a gene or nucleic acid sequence from a different species than the species of the host organism it is introduced into. When referring to a gene regulatory sequence or to an auxiliary nucleic acid sequence used for manipulating expression of a gene sequence (e.g. a 5' untranslated region, 3' untranslated region, poly A addition sequence, intron sequence, splice site, ribosome binding site, internal ribosome entry sequence, genome homology region, recombination site, etc.) or to a nucleic acid sequence encoding a protein domain or protein localization sequence, "heterologous" means that the regulatory or auxiliary sequence or sequence encoding a protein domain or localization sequence is from a different source than the gene with which the regulatory or auxiliary nucleic acid sequence or nucleic acid sequence encoding a protein domain or localization sequence is juxtaposed in a genome, chromosome or episome. Thus, a promoter operably linked to a gene to which it is not operably linked to in its natural state (for example, in the genome of a non-genetically engineered organism) is referred to herein as a "heterologous promoter," even though the promoter may be derived from the same species (or, in some cases, the same organism) as the gene to which it is linked. An intron inserted into a gene that it is not associated with in nature (for example, an intron derived from a different gene) is referred to herein as a "heterologous intron," even though the promoter may be derived from the same species (or, in some cases, the same organism) as the gene into which it is engineered. Similarly, when referring to a protein localization sequence or protein domain of an engineered protein, "heterologous" means that the localization sequence or protein domain is derived from a protein different from that into which it is incorporated by genetic engineering.

The term "hybridization", as used herein, refers generally to the ability of nucleic acid molecules to join via complementary base strand pairing. Such hybridization may occur when nucleic acid molecules are contacted under appropriate conditions and/or circumstances. As used herein, two nucleic acid molecules are said to be capable of specifically hybridizing to one another if the two molecules are capable of forming an anti-parallel, double-stranded nucleic acid structure. A nucleic acid molecule is said to be the "complement" of another nucleic acid molecule if they exhibit complete complementarity. As used herein, nucleic acid molecules are said to exhibit "complete complementarity" when every nucleotide of one of the molecules is complementary to its base pairing partner nucleotide of the other. Two molecules are said to be "minimally complementary" if they can hybridize to one another with sufficient stability to permit them to remain annealed to one another under at least conventional "low-stringency" conditions. In some instances, the molecules are said to be "complementary" if they can hybridize to one another with sufficient stability to permit them to remain annealed to one another under conventional "high-stringency" conditions. Nucleic acid molecules that hybridize to other nucleic acid molecules, e.g., at least under low stringency conditions are said to be "hybridizable cognates" of the other nucleic acid molecules. Conventional stringency conditions are described by Sambrook et al., Molecular Cloning, A Laboratory Handbook, Cold Spring Harbor Laboratory Press, 1989), and by Haymes et al. In: Nucleic Acid Hybridization, A Practical Approach, IRL Press, Washington, D.C. (1985). Departures from complete complementarity are therefore permissible, as long as such departures do not completely preclude the capacity of the molecules to form a double-stranded structure. Thus, in order for a nucleic acid molecule or fragment thereof of the present disclosure to serve as a primer or probe it needs only be sufficiently complementary in sequence to be able to form a stable double-stranded structure under the particular solvent and salt concentrations employed.

Appropriate stringency conditions which promote DNA hybridization include, for example, 6.0× sodium chloride/sodium citrate (SSC) at about 45° C., followed by a wash of 2.0×SSC at about 50° C. In addition, the temperature in the wash step can be increased from low stringency conditions at room temperature, about 22° C., to high stringency conditions at about 65° C. Both temperature and salt may be varied, or either the temperature or the salt concentration may be held constant while the other variable is changed. These conditions are known to those skilled in the art, or can be found in Current Protocols in Molecular Biology, John Wiley & Sons, N.Y. (1989), 6.3.1-6.3.6. For example, low stringency conditions may be used to select nucleic acid sequences with lower sequence identities to a target nucleic acid sequence. One may wish to employ conditions such as about 0.15 M to about 0.9 M sodium chloride, at temperatures ranging from about 20° C. to about 55° C. High stringency conditions may be used to select for nucleic acid sequences with higher degrees of identity to the disclosed nucleic acid sequences (Sambrook et al., 1989, supra). In one embodiment of the present disclosure, high stringency conditions involve nucleic acid hybridization in about 2×SSC to about 10×SSC (diluted from a 20×SSC stock solution containing 3 M sodium chloride and 0.3 M sodium citrate, pH 7.0 in distilled water), about 2.5× to about 5×Denhardt's solution (diluted from a 50× stock solution containing 1% (w/v) bovine serum albumin, 1% (w/v) ficoll, and 1% (w/v) polyvinylpyrrolidone in distilled water), about 10 mg/mL to about 100 mg/mL fish sperm DNA, and about 0.02% (w/v) to about 0.1% (w/v) SDS, with an incubation at about 50° C. to about 70° C. for several hours to overnight. High stringency conditions are preferably provided by 6×SSC, 5×Denhardt's solution, 100 mg/mL sheared and denatured salmon sperm DNA, and 0.1% (w/v) SDS, with incubation at 55×C for several hours. Hybridization is generally followed by several wash steps. The wash compositions generally comprise 0.5×SSC to about 10×SSC, and 0.01% (w/v) to about 0.5% (w/v) SDS with a 15-min incubation at about 20° C. to about 70° C. Preferably, the nucleic acid segments remain hybridized after washing at least one time in 0.1×SSC at 65° C. In some instances, very high stringency conditions may be used to select for nucleic acid sequences with much higher degrees of identity to the disclosed nucleic acid sequences. Very high stringency conditions are defined as prehybridization and hybridization at 42° C. in 5×SSPE, 0.3% SDS, 200 µg/mL sheared and denatured salmon sperm DNA, and 50% formamide and washing three times each for 15 minutes using 2×SSC, 0.2% SDS at 70° C.

The term "expression cassette" as used herein, refers to a nucleic acid construct that encodes a protein or functional RNA (e.g. a tRNA, a short hairpin RNA, one or more microRNAs, a ribosomal RNA, etc.) operably linked to expression control elements, such as a promoter, and optionally, any or a combination of other nucleic acid sequences that affect the transcription or translation of the gene, such as, but not limited to, a transcriptional terminator, a ribosome binding site, a splice site or splicing recognition sequence, an intron, an enhancer, a polyadenylation signal, an internal ribosome entry site, etc.

"Regulatory sequence", "regulatory element", or "regulatory element sequence" refers to a nucleotide sequence located upstream (5'), within, or downstream (3') of a coding sequence. Transcription of the coding sequence and/or translation of an RNA molecule resulting from transcription of the coding sequence are typically affected by the presence or absence of the regulatory sequence. These regulatory element sequences may comprise promoters, cis-elements, enhancers, terminators, or introns. Regulatory elements may be isolated or identified from UnTranslated Regions (UTRs) from a particular polynucleotide sequence. Any of the regulatory elements described herein may be present in a chimeric or hybrid regulatory expression element. Any of the regulatory elements described herein may be present in a recombinant construct of the present invention.

The terms "promoter", "promoter region", or "promoter sequence" refer to a nucleic acid sequence capable of binding RNA polymerase to initiate transcription of a gene in a 5' to 3' ("downstream") direction. A gene is "under the control of" or "regulated by" a promoter when the binding of RNA polymerase to the promoter is the proximate cause of said gene's transcription. The promoter or promoter region typically provides a recognition site for RNA polymerase and other factors necessary for proper initiation of transcription. A promoter may be isolated from the 5' untranslated region (5' UTR) of a genomic copy of a gene. Alternatively, a promoter may be synthetically produced or designed by altering known DNA elements. Also considered are chimeric promoters that combine sequences of one promoter with sequences of another promoter. Promoters may be defined by their expression pattern based on, for example, metabolic, environmental, or developmental conditions. A promoter can be used as a regulatory element for modulating expression of an operably linked transcribable polynucleotide molecule, e.g., a coding sequence. Promoters may contain, in addition to sequences recognized by RNA polymerase and, preferably, other transcription factors, regulatory sequence elements such as cis-elements or enhancer domains that affect the transcription of operably linked genes. An "algal promoter" is a native or non-native promoter that is functional in algal cells.

The term "constitutive" promoter as used herein, refers to a promoter that is active under most environmental and developmental conditions. A constitutive promoter is active regardless of external environment, such as light and culture medium composition. In some examples, a constitutive promoter is active in the presence and in the absence of a nutrient. For example, a constitutive promoter may be a promoter that is active (mediates transcription of a gene to which it is operably-linked) under conditions of nitrogen depletion as well as under conditions in which nitrogen is not limiting (nitrogen replete conditions). In contrast, an "inducible" promoter is a promoter that is active in response to particular environmental conditions, such as the presence or absence of a nutrient or regulator, the presence of light, etc.

The term "operably linked," as used herein, denotes a configuration in which a control sequence is placed at an appropriate position relative to the coding sequence of a polynucleotide sequence such that the control sequence directs or regulates the expression of the coding sequence of a polypeptide and/or functional RNA). Thus, a promoter is in operable linkage with a nucleic acid sequence if it can mediate transcription of the nucleic acid sequence. When introduced into a host cell, an expression cassette can result in transcription and/or translation of an encoded RNA or polypeptide under appropriate conditions. Antisense or sense constructs that are not or cannot be translated are not excluded by this definition. In the case of both expression of transgenes and suppression of endogenous genes (e.g., by antisense or RNAi) one of ordinary skill will recognize that the inserted polynucleotide sequence need not be identical, but may be only substantially identical to a sequence of the gene from which it was derived. As explained herein, these substantially identical variants are specifically covered by reference to a specific nucleic acid sequence.

The term "selectable marker" or "selectable marker gene" as used herein includes any gene that confers a phenotype on a cell in which it is expressed to facilitate the selection of cells that are transfected or transformed with a nucleic acid construct of the invention. The term may also be used to refer to gene products that effectuate said phenotypes. Non-limiting examples of selectable markers include: 1) genes conferring resistance to antibiotics such as amikacin (aphA6), ampicillin (ampR), blasticidin (bls, bsr, bsd), bleomicin or phleomycin (ZEOCIN™) (ble), chloramphenicol (cat), emetine (RBS14p or cry1-1), erythromycin (ermE), G418 (GENETICIN™) (neo), gentamycin (aac3 or aacC4), hygromycin B (aphIV, hph, hpt), kanamycin (nptII), methotrexate (DHFR mtxR), penicillin and other β-lactams (β-lactamases), streptomycin or spectinomycin (aadA, spec/strep), and tetracycline (tetA, tetM, tetQ); 2) genes conferring tolerance to herbicides such as aminotriazole, amitrole, andrimid, aryloxyphenoxy propionates, atrazines, bipyridyliums, bromoxynil, cyclohexandione oximes dalapon, dicamba, diclfop, dichlorophenyl dimethyl urea (DCMU), difunone, diketonitriles, diuron, fluridone, glufosinate, glyphosate, halogenated hydrobenzonitriles, haloxyfop, 4-hydroxypyridines, imidazolinones, isoxasflutole, isoxazoles, isoxazolidinones, miroamide B, p-nitrodiphenylethers, norflurazon, oxadiazoles, m-phenoxybenzamides, N-phenyl imides, pinoxadin, protoporphyrionogen oxidase inhibitors, pyridazinones, pyrazolinates, sulfonylureas, 1,2,4-triazol pyrimidine, triketones, or urea; acetyl CoA carboxylase (ACCase); acetohydroxy acid synthase (ahas); acetolactate synthase (als, csr1-1, csr1-2, imr1, imr2), aminoglycoside phosphotransferase (apt), anthranilate synthase, bromoxynil nitrilase (bxn), cytochrome P450-NADH-cytochrome P450 oxidoreductase, dalapon dehalogenase (dehal), dihydropteroate synthase (sul), class I 5-enolpyruvylshikimate-3-phosphate synthase (EPSPS), class II EPSPS (aroA), non-class I/II EPSPS, glutathione reductase, glyphosate acetyltransferase (gat), glyphosate oxidoreductase (gox), hydroxyphenylpyruvate dehydrogenase, hydroxy-phenylpyruvate dioxygenase (hppd), isoprenyl pyrophosphate isomerase, lycopene cyclase, phosphinothricin acetyl transferase (pat, bar), phytoene desaturase (crtl), prenyl transferase, protoporphyrin oxidase, the psbA photosystem II polypeptide (psbA), and SMM esterase (SulE) superoxide dismutase (sod); 3) genes that may be used in auxotrophic strains or to confer other metabolic effects, such as arg7, his3, hisD, hisG, lysA, manA, metE, nitl, trpB, ura3, xylA, a dihydrofolate reductase gene, a mannose-6-phosphate isomerase gene, a nitrate reductase gene, or an ornithine decarboxylase gene; a negative selection factor such as thymidine kinase; or toxin resistance factors such as a 2-deoxyglucose resistance gene.

A "reporter gene" is a gene encoding a protein that is detectable or has an activity that produces a detectable product. A reporter gene can encode a visual marker or enzyme that produces a detectable signal, such as cat, lacZ, uidA, xylE, an alkaline phosphatase gene, an α-amylase gene, an α-galactosidase gene, a β-glucuronidase gene, a β-lactamase gene, a horseradish peroxidase gene, a luciferin/luciferase gene, an R-locus gene, a tyrosinase gene, or a gene encoding a fluorescent protein, including but not limited to a blue, cyan, green, red, or yellow fluorescent protein, a photoconvertible, photoswitchable, or optical highlighter fluorescent protein, or any of variant thereof, including, without limitation, codon-optimized, rapidly folding, monomeric, increased stability, and enhanced fluorescence variants.

The term "terminator" or "terminator sequence" or "transcription terminator" as used herein refers to a regulatory section of genetic sequence that causes RNA polymerase to cease transcription.

The term "transformation" as used herein refers to the introduction of one or more exogenous nucleic acid sequences or polynucleotides into a host cell or organism by using one or more physical, chemical, or biological methods. Physical and chemical methods of transformation (i.e., "transfection") include, by way of non-limiting example, electroporation, particle bombardment, and liposome delivery. Biological methods of transformation (i.e., "transduction") include transfer of DNA using engineered viruses or microbes (e.g., *Agrobacterium*).

The term "photosynthetic organism" as used herein is any prokaryotic or eukaryotic organism that can perform photosynthesis. Photosynthetic organisms include higher plants (i.e., vascular plants), bryophytes, algae, and photosynthetic bacteria. The term "algae" includes, but is not limited to, a species of Bacillariophyceae (diatoms), Bolidomonas, Chlorophyceae (green algae), Chrysophyceae (golden algae), Carophyceae, Cyanophyceae (cyanobacteria), Eustigmatophyceae (pico-plankton), Glaucocystophytes, Pelagophytes, Phaeophyceae (brown algae), Prasinophyceae (pico-plankton), Raphidophytes, Rhodophyceae (red algae), Synurophyceae and Xanthophyceae (yellow-green algae). The term "algae" includes microalgae. The term "microalgae" as used herein refers to microscopic, single-celled algae species including, but not limited to, eukaryotic single-celled algae of the Bacillariophyceae, Chlorophyceae, Prasinophyceae, Trebouxiophyceae, and Eustigmatophyceae classes. The term "photosynthetic bacteria" includes, but is not limited to, cyanobacteria, green sulfur bacteria, purple sulfur bacteria, purple non-sulfur bacteria, and green non-sulfur bacteria.

Nucleotide Sequences

Genes were identified and isolated from a *Parachlorella* environmental isolate (designated WT-1185) as sources for promoter and terminator sequences that can find use in the expression of genes, such as but not limited to transgenes, in eukaryotic microorganisms. SEQ ID NO:1, SEQ ID NO:4, SEQ ID NO:8, SEQ ID NO:11, SEQ ID NO:13, SEQ ID NO:15, SEQ ID NO:17, SEQ ID NO:19, SEQ ID NO:21, and SEQ ID NO:23 were identified to comprise promoters that were demonstrated to mediate expression of transgenes in WT-1185, and SEQ ID NO:7, SEQ ID NO:9, SEQ ID NO:12, SEQ ID NO:14, SEQ ID NO:16, SEQ ID NO:18, SEQ ID NO:20, SEQ ID NO:22, and SEQ ID NO:24 were identified as comprising terminators functional in WT-1185.

sequence to which it is operably linked, for example, the nucleotide sequence can direct expression of a nucleic acid sequence of a protein-encoding sequence or a sequence encoding a functional RNA. In some examples, molecule nucleotide sequence as provided herein can mediate transcriptional termination of a gene to which it is operably linked. For example, an isolated DNA molecule as provided herein can comprise a nucleotide sequence having at least 85% or at least 90% identity to at least 100, at least 200, at least 300, at least 400, or at least 500 contiguous nucleotides of SEQ ID NO:1, SEQ ID NO:4, SEQ ID NO:8, SEQ ID NO:11, SEQ ID NO:13, SEQ ID NO:15, SEQ ID NO:17, SEQ ID NO:19, SEQ ID NO:21, SEQ ID NO:23, SEQ ID NO:7, SEQ ID NO:9, SEQ ID NO:12, SEQ ID NO:14, SEQ ID NO:16, SEQ ID NO:18, SEQ ID NO:20, SEQ ID NO:22, or SEQ ID NO:24. In some examples, an isolated or recombinant DNA molecule as provided herein can include a nucleotide sequence that can have at least 95%, 96%, 97%, 98%, or 99% percent identity to at least 100 contiguous nucleotides to any one of SEQ ID NO:1, SEQ ID NO:4, SEQ ID NO:8, SEQ ID NO:11, SEQ ID NO:13, SEQ ID NO:15, SEQ ID NO:17, SEQ ID NO:19, SEQ ID NO:21, SEQ ID NO:23, SEQ ID NO:7, SEQ ID NO:9, SEQ ID NO:12, SEQ ID NO:14, SEQ ID NO:16, SEQ ID NO:18, SEQ ID NO:20, SEQ ID NO:22, or SEQ ID NO:24. In further examples, an isolated DNA molecule can comprise any of SEQ ID NO:1, SEQ ID NO:4, SEQ ID NO:8, SEQ ID NO:11, SEQ ID NO:13, SEQ ID NO:15, SEQ ID NO:17, SEQ ID NO:19, SEQ ID NO:21, SEQ ID NO:23, SEQ ID NO:7, SEQ ID NO:9, SEQ ID NO:12, SEQ ID NO:14, SEQ ID NO:16, SEQ ID NO:18, SEQ ID NO:20, SEQ ID NO:22, or SEQ ID NO:24. A nucleotide sequence as provided herein can mediate or enhance expression of a heterologous nucleic acid sequence to which it is operably linked. Additionally or alternatively, the isolated DNA molecule can have terminator activity, for example, the nucleotide sequence can mediate transcriptional termination of a gene to which it is operably linked.

TABLE 1

Regulatory Sequence ID Numbers

| Gene name | Plasmid | Promoter 5'-UTR | Terminator 3'-UTR |
|---|---|---|---|
| Ribosomal Protein S4 (RPS4) | p06567 | SEQ ID NO: 1 | SEQ ID NO: 7 |
| Photosystem II subunit R (PsbR) | p06450 | SEQ ID NO: 4 | |
| Acyl-Carrier Protein (ACP) | p06640 | SEQ ID NO: 8 | SEQ ID NO: 9 |
| Organellar oligopeptidase A | p06633 | SEQ ID NO: 11 | SEQ ID NO: 12 |
| Fructose 1,6-Bisphosphatase (FBPase) | p06634 | SEQ ID NO: 13 | SEQ ID NO: 14 |
| Elongation factor 2 | p06635 | SEQ ID NO: 15 | SEQ ID NO: 16 |
| 30S Ribosomal protein S17 (RPS17) | p06636 | SEQ ID NO: 17 | SEQ ID NO: 18 |
| Mitochondrial ATP synthase | p06637 | SEQ ID NO: 19 | SEQ ID NO: 20 |
| Rubisco small subunit isoform 1 | p06638 | SEQ ID NO: 21 | SEQ ID NO: 22 |
| Rubisco small subunit isoform 2 | p06639 | SEQ ID NO: 23 | SEQ ID NO: 24 |

Thus, isolated and recombinant DNA (nucleic acid) molecules are provided herein that comprise nucleotide sequences having about 80% identity to at least 100 contiguous nucleotides to any one of SEQ ID NO:1, SEQ ID NO:4, SEQ ID NO:8, SEQ ID NO:11, SEQ ID NO:13, SEQ ID NO:15, SEQ ID NO:17, SEQ ID NO:19, SEQ ID NO:21, SEQ ID NO:23, SEQ ID NO:7, SEQ ID NO:9, SEQ ID NO:12, SEQ ID NO:14, SEQ ID NO:16, SEQ ID NO:18, SEQ ID NO:20, SEQ ID NO:22, or SEQ ID NO:24. In some examples, a nucleotide sequence as provided herein can direct expression in a eukaryotic cell, such as but not limited to an algal, fungal, or chlorophyte cell, of a nucleic acid For example, isolated and recombinant DNA (nucleic acid) molecules are provided herein that comprise nucleotide sequences having about 80% identity to at least 100 contiguous nucleotides from the 3'-most end of any one of SEQ ID NO:1, SEQ ID NO:4, SEQ ID NO:8, SEQ ID NO:11, SEQ ID NO:13, SEQ ID NO:15, SEQ ID NO:17, SEQ ID NO:19, SEQ ID NO:21, and SEQ ID NO:23. For example, an isolated DNA molecule as provided herein can have at least 85% or at least 90% identity to at least 100, at least 200, at least 300, at least 400, or at least 500 contiguous nucleotides, extending from the 3' end and extending 5', of SEQ ID NO:1, SEQ ID NO:4, SEQ ID NO:8, SEQ ID NO:11, SEQ ID NO:13, SEQ ID NO:15, SEQ ID NO:17, SEQ ID NO:19, SEQ ID NO:21, and SEQ ID NO:23. In some examples, a DNA molecule as provided herein can include a nucleotide sequence that can have at least 95%, 96%, 97%, 98%, or 99% percent identity to at least 100 contiguous nucleotides extending from the 3' end of any one of SEQ ID NO:1, SEQ ID NO:4, SEQ ID NO:8, SEQ ID NO:11, SEQ ID NO:13, SEQ ID NO:15, SEQ ID NO:17, SEQ ID NO:19, SEQ ID NO:21, and SEQ ID NO:23. In further examples, an isolated DNA molecule can comprise any of SEQ ID NO:1, SEQ ID NO:4, SEQ ID NO:8, SEQ ID NO:11, SEQ ID NO:13, SEQ ID NO:15, SEQ ID NO:17, SEQ ID NO:19, SEQ ID NO:21, and SEQ ID NO:23. In some examples, a nucleic acid molecule as provided herein can mediate or enhance expression of a heterologous nucleic acid sequence to which it is operably linked.

The isolated DNA molecule can find use, for example, as a sequence that when operably linked to a nucleic acid sequence can affect expression of the nucleic acid sequence, which can comprise, for example, a sequence encoding a polypeptide or functional RNA. For example, the isolated DNA molecule can increase or decrease expression of a nucleic acid sequence to which it is operably linked, or may mediate transcription of the operably-linked nucleic acid sequence as a promoter. Methods for assessing the functionality of nucleotide sequences for promoter activity as well as for enhancing or decreasing the activity of proximal promoters are well-known in the art. For example, promoter function can be validated by confirming the ability of the putative promoter or promoter variant or fragment to drive expression of a selectable marker gene to which the putative promoter or promoter fragment or variant is operably linked by detecting and, optionally, analyzing, resistant colonies (and/or their progeny) after plating of cells transformed with the promoter construct on selective media. Alternatively or in addition, promoter activity may be assessed by measuring the levels of RNA transcripts produced from a promoter construct, for example, using reverse transcription-polymerase chain reaction (RT-PCR, e.g., Watt et al. (2008) *PLoS ONE* 1: e1428), by detection of the expressed protein, or by in vivo assays that rely on an activity of the protein encoded by the transcribed sequence. For example, promoter activity can be assessed using chloramphenicol acetyltransferase (CAT) assays (where the heterologous sequence operably linked to the isolated nucleic acid molecule that comprises a putative promoter encodes chloramphenicol acetyltransferase, see, for example, Gerrish et al. (2000) *J. Biol. Chem.* 275: 3485-3492), luciferase assays, where the heterologous nucleic acid is a lux or luc gene, for example (see, for example, Ferrante et al. (2008) *PLoS ONE* 3: e3200), or in vivo assays using a fluorescent protein gene to determine the functionality of any of the sequences disclosed herein, including sequences of reduced size or having one or more nucleotide changes with respect to any of SEQ ID NOs 1-8. (see, for example, Akamura et al. (2011) *Anal. Biochem.* 412: 159-164). Testing of sequence modifications, including deletions and base substitutions of the promoter-containing sequences using reporter constructs such as but not limited to those provided herein are well-known in the art (see, for example, Quinn et al. (2003) *Eukaryotic Cell* 2: 995-1002; Ranjan et al. (2011) *J. Biotechnol.* 152: 58-62; Gerrish et al. (2000) *J. Biol. Chem.* 275: 3485-3492; all incorporated herein by reference). See also US patent application publication No. 2014-0363892 published Dec. 11, 2014; 2013-0323780 published Dec. 5, 2013, and U.S. Pat. No. 8,883,993 issued Nov. 11, 2014, all of which are incorporated by reference in their entireties.

Promoters

Also provided herein are promoters comprising a nucleic acid sequence such as any described herein, for example, a nucleic acid sequence having at least 80% identity to at least 100 contiguous nucleotides of SEQ ID NO:1, SEQ ID NO:4, SEQ ID NO:8, SEQ ID NO:11, SEQ ID NO:13, SEQ ID NO:15, SEQ ID NO:17, SEQ ID NO:19, SEQ ID NO:21, or SEQ ID NO:23. For example, a promoter as provided herein may include a nucleotide sequence that has at least 85% or at least 90% sequence identity to at least 100, 200, 300, 400, or 500 contiguous nucleotides of SEQ ID NO:1, SEQ ID NO:4, SEQ ID NO:8, SEQ ID NO:11, SEQ ID NO:13, SEQ ID NO:15, SEQ ID NO:17, SEQ ID NO:19, SEQ ID NO:21, or SEQ ID NO:23. Additionally or alternatively, a promoter can include a sequence that has at least 95% sequence identity to at least 100, 200, 300, 400, or 500 contiguous nucleotides of SEQ ID NO:1, SEQ ID NO:4, SEQ ID NO:8, SEQ ID NO:11, SEQ ID NO:13, SEQ ID NO:15, SEQ ID NO:17, SEQ ID NO:19, SEQ ID NO:21, or SEQ ID NO:23. Additionally or alternatively, a promoter as provided herein can be selected from the group consisting of an isolated DNA molecule comprising at least 100 contiguous nucleotides of SEQ ID NO:1, SEQ ID NO:4, SEQ ID NO:8, SEQ ID NO:11, SEQ ID NO:13, SEQ ID NO:15, SEQ ID NO:17, SEQ ID NO:19, SEQ ID NO:21, or SEQ ID NO:23.

In various examples a promoter as provided herein includes a nucleotide sequence that has at least 85%, at least 90%, or at least 95% sequence identity to at least 100, 200, 300, 400, or 500 contiguous nucleotides extending from the 3' end toward the 5' end of any of SEQ ID NO:1, SEQ ID NO:4, SEQ ID NO:8, SEQ ID NO:11, SEQ ID NO:13, SEQ ID NO:15, SEQ ID NO:17, SEQ ID NO:19, SEQ ID NO:21, or SEQ ID NO:23. In particular examples, a promoter as provided herein comprises a nucleic acid sequence having at least 85%, at least 90%, at least 95%, at least 96%, at least 97%, at least 98%, at least 99% to at least 100, 200, 300, 400, 500, or 530 contiguous nucleotides extending from the 3' end of SEQ ID NO:1. In other examples, a promoter as provided herein comprises a nucleic acid sequence having at least 85%, at least 90%, at least 95%, at least 96%, at least 97%, at least 98%, at least 99% to at least 100, 200, 300, 400, 500, 600, 700, 800, 900, or 1000 contiguous nucleotides extending from the 3' end of SEQ ID NO:4. In particular examples, a promoter as provided herein comprises a nucleic acid sequence having at least 85%, at least 90%, at least 95%, at least 96%, at least 97%, at least 98%, at least 99% to at least 100, 200, 300, 400, 500, or 572 contiguous nucleotides extending from the 3' end of SEQ ID NO:8. In other examples, a promoter as provided herein comprises a nucleic acid sequence having at least 85%, at least 90%, at least 95%, at least 96%, at least 97%, at least 98%, at least 99% to at least 100, 200, 300, 400, 500, 600, 700, 800, 900, 1000, or 1044 contiguous nucleotides extending from the 3' end of SEQ ID NO:11. In further examples, a promoter as provided herein comprises a nucleic acid sequence having at least 85%, at least 90%, at least 95%, at least 96%, at least 97%, at least 98%, at least 99% to at least 100, 200, 300, 400, 500, 600, 700, 800, or 832 contiguous nucleotides extending from the 3' end of SEQ ID NO:13. In particular examples, a promoter as provided herein comprises a nucleic acid sequence having at least 85%, at least 90%, at least 95%, at least 96%, at least 97%, at least 98%, at least 99% to at least 100, 200, 300, 400, 500, 600, or 642 contiguous nucleotides extending from the 3' end of SEQ ID NO:15. In other examples, a promoter as provided herein comprises a nucleic acid sequence having at least 85%, at least 90%, at least 95%, at least 96%, at least 97%, at least 98%, at least 99% to at least 100, 200, 300, 400, 500, or 588 contiguous nucleotides extending from the 3' end of SEQ ID NO:17. In particular examples, a promoter as provided herein comprises a nucleic acid sequence having at least 85%, at least 90%, at least 95%, at least 96%, at least 97%, at least 98%, at least 99% to at least 100, 200, 300, 400, 500, 600, 700, or 707 contiguous nucleotides extending from the 3' end of SEQ ID NO:19. In other examples, a promoter as provided herein comprises a nucleic acid sequence having at least 85%, at least 90%, at least 95%, at least 96%, at least 97%, at least 98%, at least 99% to at least 100, 200, 300, 400, 500, 600, 700, 800, or 874 contiguous nucleotides extending from the 3' end of SEQ ID NO:21. In yet further examples, a promoter as provided herein comprises a nucleic acid sequence having at least 85%, at least 90%, at least 95%, at least 96%, at least 97%, at least 98%, at least 99% to at least 100, 200, 300, 400, 500, 600, 700, 800, or 874 contiguous nucleotides extending from the 3' end of SEQ ID NO:23.

In various examples of promoters of the present invention a promoter is selected from the group consisting of: SEQ ID NO:1, SEQ ID NO:4, SEQ ID NO:8, SEQ ID NO:11, SEQ ID NO:13, SEQ ID NO:15, SEQ ID NO:17, SEQ ID NO:19, SEQ ID NO:21, and SEQ ID NO:23.

A promoter as provided herein can be a constitutive promoter, for example the promoter may be active in culture conditions in which one or more nutrients are deficient as well as in culture conditions in which nutrients are sufficient for proliferation and/or growth of the culture. For example, a promoter as provided herein may direct expression of an operably linked nucleic acid sequence under conditions in which a host cell that includes the promoter construct is limited in nitrogen availability (nitrogen depletion/deficiency) as well as under conditions in which a host cell that includes the promoter construct is not limited in nitrogen availability (nitrogen replete conditions). Additionally or alternatively, a promoter as provided herein may direct expression of an operably linked nucleic acid sequence under conditions in which a host cell that includes the promoter construct is exposed to varying or continuous light intensities throughout the day.

Without being bound by theory, promoters allow RNA polymerase to attach to the DNA near a gene in order for transcription to take place. Promoters contain specific DNA sequences that provide transcription factors an initial binding site from which they can recruit RNA polymerase binding. These transcription factors have specific protein motifs that enable them to interact with specific corresponding nucleotide sequences to regulate gene expressions. The proximal promoter sequence may be between approximately 50, and 500 bp upstream of the translational start site of the open reading frame of the gene, although these are general guidelines only, and may contain, in addition to sequences for binding RNA polymerase, specific transcription factor binding sites. Some promoters also include distal sequence upstream of the gene that may contain additional regulatory elements, often with a weaker influence than the proximal promoter. Eukaryotic transcriptional complexes can bend the DNA back on itself, thus allowing for potential placement of additional regulatory sequences as far as several kilobases from the TSS. Many eukaryotic promoters contain a TATA box, although this is not a universal feature of eukaryotic promoters. The TATA box binds the TATA binding protein, which assists in the formation of the RNA polymerase transcriptional complex. TATA boxes usually lie within approximately 50 bp of the TSS. A promoter may be constitutive or expressed conditionally. Some promoters are inducible, and may activate or increase transcription in response to an inducing agent. In contrast, the rate of transcription of a gene under control of a constitutive promoter is not dependent on an inducing agent. A constitutive promoter can be made a conditional or inducible promoter by the addition of sequences that confer responsiveness to particular conditions or to an inducing agent. Thus, promoters provided herein may be constitutive or may be inducible or conditional. Further, promoters or portions of promoters may be combined in series to achieve a stronger level of expression or a more complex pattern of regulation.

In various examples, a promoter as provided herein, such as but not limited to a promoter that comprises a nucleotide sequence having at least 80%, at least 85%, at least 90%, at least 95%, at least 96%, at least 97%, at least 98%, at least 99%, or about 100% identity to at least 100, at least 200, at least 300, at least 400, or at least 500 contiguous nucleotides of SEQ ID NO:1, SEQ ID NO:4, SEQ ID NO:8, SEQ ID NO:11, SEQ ID NO:13, SEQ ID NO:15, SEQ ID NO:17, SEQ ID NO:19, SEQ ID NO:21, or SEQ ID NO:23, can mediate transcription of an operably linked nucleic acid sequence in a eukaryotic algal cell, such as, but not limited to any species of any of the genera *Achnanthes, Amphiprora, Amphora, Ankistrodesmus, Asteromonas, Boekelovia, Bolidomonas, Borodinella, Botrydium, Botryococcus, Bracteococcus, Chaetoceros, Carteria, Chlamydomonas, Chlorococcum, Chlorogonium, Chlorella, Chroomonas, Chrysosphaera, Cricosphaera, Crypthecodinium, Cryptomonas, Cyclotella, Dunaliella, Ellipsoidon, Emiliania, Eremosphaera, Ernodesmius, Euglena, Eustigmatos, Franceia, Fragilaria, Fragilariopsis, Gloeothamnion, Haematococcus, Halocafeteria, Heterosigma, Hymenomonas, Isochrysis, Lepocinclis, Micractinium, Monoraphidium, Nannochloris, Nannochloropsis, Navicula, Neochloris, Nephrochloris, Nephroselmis, Nitzschia, Ochromonas, Oedogonium, Oocystis, Ostreococcus, Pavlova, Parachlorella, Pascheria, Pelagomonas, Phaeodactylum, Phagus, Picochlorum, Platymonas, Pleurochrysis, Pleurococcus, Prototheca, Pseudochlorella, Pseudoneochloris, Pseudostaurastrum, Pyramimonas, Pyrobotrys, Scenedesmus, Skeletonema, Spyrogyra, Stichococcus, Tetraselmis, Thalassiosira, Tribonema, Vaucheria, Viridiella, Vischeria,* and *Volvox.*

For example, a promoter as disclosed herein can be functional in a green alga, i.e., an algal member of the Chlorophyte division of the Viridiplantae kingdom, including without limitation, a microalga of any of the classes Chlorophyceae, Chlorodendrophyceae, Pedinophyceae, Pleurastrophyceae, Prasinophyceae, and Trebouxiophyceae. In some examples, a promoter as provided herein can be operable in a species that is a member of any of the Chlorophyceae, Prasinophyceae, Trebouxiophyceae, or Chlorodendrophyceae classes, such as a species of any of the *Asteromonas, Ankistrodesmus, Carteria, Chlamydomonas, Chlorococcum, Chlorogonium, Chrysosphaera, Desmodesmus, Dunaliella, Haematococcus, Monoraphidium, Neochloris, Oedogonium, Pelagomonas, Pleurococcus, Pyrobotrys, Scenedesmus, Volvox, Micromonas, Ostreococcus Prasinocladus Scherffelia, Tetraselmis, Botryococcus, Chlorella, Eremosphaera, Franceia, Micractinium, Nannochloris, Oocystis, Parachlorella, Picochlorum, Prototheca,* or *Pseudochlorella* genera. In various examples, a promoter as provided can direct expression of a gene to which it is operably linked in a species of Trebouxiophyceae, such as but not limited to *Botryococcus, Chlorella, Eremosphaera, Franceia, Micractinium, Nannochloris, Oocystis, Parachlorella, Picochlorum, Prototheca,* or *Pseudochlorella*.

In some instances, a promoter as provided herein can mediate transcription of an operably linked nucleic acid sequence in a eukaryotic cell, such as but not limited to a eukaryotic algal cell, during culturing of the cell under conditions of nitrogen depletion as well as during culturing of the cell under nitrogen replete conditions. For example, a promoter as described herein can preferably mediate transcription of an operably linked nucleic acid sequence in *Parachlorella* cells cultured under conditions of nitrogen depletion or cultured under nitrogen replete conditions.

Additionally, as contemplated herein, a promoter or promoter region can include variants of the promoters disclosed herein derived by deleting sequences, duplicating sequences, or adding sequences from other promoters or as designed, for example, by bioinformatics, or by subjecting the promoter to random or site-directed mutagenesis, etc. In some examples, promoters can obtained by truncation of any of SEQ ID NO:1, SEQ ID NO:4, SEQ ID NO:8, SEQ ID NO:11, SEQ ID NO:13, SEQ ID NO:15, SEQ ID NO:17, SEQ ID NO:19, SEQ ID NO:21, and SEQ ID NO:23, or truncated versions of variants thereof having at least 80%, at least 85%, at least 90%, or at least 95% identity thereto. Promoters of the present invention can include nucleic acid sequences having at least 80%, at least 85%, at least 90%, at least 95%, or between 95% and 100% identity to the sequences between about 0 bp, 20 bp, 50 bp, 100 bp, 200 bp or 300 bp to about 500 bp, 600 bp, 700 bp, 800 bp, 900 bp, or 1 kb upstream of the trinucleotide ATG sequence at the start site of a protein coding region of a native *Parachlorella* gene, such as, for example, an RSP4 gene, a photosystem II subunit R (PsbR) gene, an organellar oligopeptidase A gene, a FPBase gene, an Elongation Factor 2 gene, a 30S ribosomal protein S17 gene, a mitochondrial ATP synthase gene, a rubisco small subunit isoform 1 gene, a rubisco small subunit isoform 2 gene, or an acyl-carrier protein gene.

The activity or strength of a promoter may be measured in terms of the amounts of RNA it produces, or the amount of protein accumulation in a cell or tissue, which can optionally be measured by an activity of the expressed protein, e.g., fluorescence, luminescence, acyltransferase activity, etc., relative to a control promoter, for example, a promoter whose transcriptional activity has been previously assessed or a promoter from which a truncated and/or sequence modified variant has been derived, relative to a promoterless construct, or relative to non-transformed cells. For example, the activity or strength of a promoter may be measured in terms of the amount of mRNA accumulated that corresponds to a nucleic acid sequence to which it is operably linked in a cell, relative to the total amount of mRNA or protein produced by the cell. The promoter preferably expresses an operably linked nucleic acid sequence at a level greater than 0.01%; preferably in a range of about 0.5% to about 20% (w/w) of the total cellular RNA. The activity can also be measured by quantifying fluorescence, luminescence, or absorbance of the cells or a product made by the cells or an extract thereof, depending on the activity of a reporter protein that may be expressed from the promoter. The activity or strength of a promoter may be expressed relative to a well-characterized promoter (e.g., for which transcriptional activity was previously assessed). For example, a less-characterized promoter may be operably linked to a reporter sequence (e.g., a fluorescent protein) and introduced into a specific cell type. A well-characterized promoter is similarly prepared and introduced into the same cellular context. Transcriptional activity of the unknown promoter is determined by comparing the amount of reporter expression, relative to the well characterized promoter.

A promoter described herein can have promoter activity in a eukaryotic cell, preferably in an algal cell or chlorophyte cell. In a particular examples, a promoter as provided herein is active in an algal or chlorophyte cell in nutrient replete and nutrient-depleted culture conditions. An algal promoter as provided herein can be used as a 5' regulatory element for modulating expression of an operably linked gene or genes in algal species as well as other organisms, including fungi, chlorophyte algae, and plants.

Terminators

In another embodiment of the present invention terminators are provided in which the terminators comprise a nucleotide sequence having at least 80%, at least 85%, at least 90%, at least 95%, at least 96%, at least 97%, at least 98%, at least 99%, or about 100% identity to at least 100 or at least 150 contiguous nucleotides of SEQ ID NO:7, SEQ ID NO:9, SEQ ID NO:12, SEQ ID NO:14, SEQ ID NO:16, SEQ ID NO:18, SEQ ID NO:20, SEQ ID NO:22, or SEQ ID NO:24, for example, having at least 80%, at least 85%, at least 90%, at least 95%, at least 96%, at least 97%, at least 98%, at least 99%, or about 100% identity to at least 100 or at least 150 contiguous nucleotides from the 5' end extending toward the 3' end of SEQ ID NO:7, SEQ ID NO:9, SEQ ID NO:12, SEQ ID NO:14, SEQ ID NO:16, SEQ ID NO:18, SEQ ID NO:20, SEQ ID NO:22, or SEQ ID NO:24.

For example, a terminator can have at least 80%, at least 85%, at least 90%, at least 95%, at least 96%, at least 97%, at least 98%, at least 99%, or about 100% identity to at least 200, at least 300, at least 400, at least 500, at least 600, at least 700, at least 800, at least 900, or at least 950 contiguous nucleotides of SEQ ID NO:7, SEQ ID NO:9, SEQ ID NO:12, SEQ ID NO:14, SEQ ID NO:16, SEQ ID NO:18, SEQ ID NO:20, SEQ ID NO:22, or SEQ ID NO:24. A terminator as provided herein can have at least 80%, at least 85%, at least 90%, at least 95%, at least 96%, at least 97%, at least 98%, at least 99%, or about 100% identity to SEQ ID NO:7, SEQ ID NO:9, SEQ ID NO:12, SEQ ID NO:14, SEQ ID NO:16, SEQ ID NO:18, SEQ ID NO:20, SEQ ID NO:22, or SEQ ID NO:24.

Terminators are genetic sequences that mark the end of a gene for transcription. Without being bound by theory, the terminators of the present invention may improve expression of the nucleic acid sequence (amount of encoded RNA or protein produced), and may mediate polyadenylation or enhance RNA transcript stability. Most terminator sequences in eukaryotes consist of at least two DNA sequences: (1) a binding site for terminator proteins and (2) an upstream element located among the last twelve nucleotides of the transcript. The protein binding sites are usually orientation-sensitive and essential to termination. Termination usually occurs between twelve and twenty nucleotides upstream of the binding site. The upstream element's functionality usually depends more on its overall base composition (T-rich) than on the specific sequence (Reeder & Lang (1997) *Trends Biochem. Sci.* 22:473-477, herein incorporated by reference in its entirety).

Introns

The term "intron" is used herein to refer to a nucleotide sequence within a gene that is removed from the RNA transcribed from the gene by RNA splicing. (The term intron is used to refer to the RNA sequence as it occurs in RNA molecules prior to splicing as well as to the DNA sequence as it occurs in the gene.) The introns disclosed herein are "spliceosomal introns" that occur naturally in the nuclear genes of eukaryotes and are spliced out by the splicing machinery (spliceosome) of eukaryotic cells. Also considered are introns derived from naturally-occurring introns, e.g., introns at least 65%, 70%, 75%, 80%, 85%, 90%, 95%, 96%, 97%, 98%, or 99% identical to the sequence of a naturally-occurring intron or an internally deleted variant thereof, for example, a variant having from 1 to 1000 bp deleted from within the borders of the intron. Also considered are chimeric introns that comprise intron sequences of two or more naturally-occurring introns. Introns include a GT (GU in the primary RNA transcript) at the 5' end, a branch site sequence near the 3' end of the intron, and an AG acceptor site at the 3' end of the intron. The surrounding exon sequence includes a GG at the 5' border with the intron, and a G after the AG at the 3' end of the intron. Such sequences can optionally be engineered into the coding sequences of a gene as provided herein at the site of intron insertion.

An intronylated gene as provided herein is engineered to include at least one heterologous intron, that is, at least one intron that does not naturally occur in the gene that encodes the polypeptide encoded by the engineered gene, and an intronylated gene in some embodiments is preferably engineered to include at least three, at least four, or at least five heterologous introns, that is, at least three, at least four, or at least five introns that do not naturally occur in the gene. For example, amino acid-encoding sequences of the engineered gene can encode a polypeptide that is not encoded by the gene from which the heterologous introns are derived. The heterologous introns are inserted into a gene that they do not occur in naturally, for example, using genetic engineering or gene synthesis techniques. The amino acid-encoding sequences of the engineered gene may optionally be altered for example to generate sequences immediately proximal to a heterologous intron to allow for correct splicing of the introduced intron and/or to alter the codon usage (for example, to reflect a codon preference of the host) and/or to introduce a mutation. In some embodiments, the at least three heterologous introns are derived from one or more genes other than the gene from which the amino acid-encoding sequences of the engineered gene are derived, for example, the at least three exogenous introns can be derived from naturally-occurring introns. In various embodiments, the at least three, at least four, or at least five exogenous introns can be naturally-occurring introns from another gene of the same or different organism from which the amino acid encoding sequences of the engineered gene are derived, or can be derived from naturally-occurring introns from another gene of the same or different organism from which the amino acid encoding sequences of the engineered gene, for example, by one or more sequence modifications or internal deletion of sequences from the naturally-occurring intron(s). In some embodiments, the at least three, at least four, or at least five exogenous introns inserted into an engineered gene are all naturally-occurring introns of the same gene, and in some embodiments multiple introns of the same naturally-occurring gene may be introduced into the engineered gene in the same order in which they occur in the naturally-occurring gene from which they are derived. In some embodiments, the engineered gene is operably linked to a promoter, and the promoter and exogenous introns can optionally be derived from the same organism. In some embodiments, the engineered gene is operably linked to a promoter and a terminator, and the promoter, terminator, and exogenous introns can all be derived from the same organism, and can all be derived from the same gene. Further, in various embodiments the amino acid-encoding sequences of the engineered gene can be codon-optimized, and in some examples can be codon optimized for expression in an organism from which the exogenous introns are derived.

An engineered gene as provided herein can include at least three, at least four, at least five, at least six, at least seven, at least eight, or at least nine exogenous introns. In some examples, an engineered gene includes at least five introns. In exemplary embodiments, the introns can range in size from about 15 nucleotides to 2000 nucleotides or more, for example, from 30 nucleotides to 1000 nucleotides or from about 60 nucleotides to about 500 nucleotides in length. In some examples, the three or more introns are selected from the group consisting of introns having at least 80%, 85%, 90%, 95%, 96%, 97%, 98%, or 99% identity to SEQ ID NO:25, SEQ ID NO:26, SEQ ID NO:27, SEQ ID NO:28, SEQ ID NO:29, SEQ ID NO:35, SEQ ID NO:36, SEQ ID NO:37, SEQ ID NO:38, SEQ ID NO:39, SEQ ID NO:40, SEQ ID NO:41, SEQ ID NO:42, and SEQ ID NO:43. For example, an engineered gene can include three or more introns selected from the group of introns having at least 65%, 70%, 75%, 80%, 85%, 90%, 95%, 96%, 97%, 98%, or 99% identity to SEQ ID NO:25, SEQ ID NO:26, SEQ ID NO:27, SEQ ID NO:28, and SEQ ID NO:29. In further examples, an engineered gene can include three or more introns selected from the group of introns having at least 80%, 85%, 90%, 95%, 96%, 97%, 98%, or 99% identity to SEQ ID NO:35, SEQ ID NO:36, SEQ ID NO:37, SEQ ID NO:38, SEQ ID NO:39, SEQ ID NO:40, SEQ ID NO:41, SEQ ID NO:42, and SEQ ID NO:43.

The engineered gene that includes at least three or at least four heterologous introns can further include a promoter operably linked to the engineered gene. The promoter can optionally be heterologous with respect to the polypeptide encoded by the gene, and can optionally be derived from a different species that the species from which the encoded polypeptide is derived. In some embodiments the promoter may be derived from the same species as at least one, at least two, at least three, at least four or all of the heterologous introns. The nucleic acid molecule can optionally further include a terminator operably linked to the engineered gene that includes at least three or at least four heterologous introns. The terminator can optionally be heterologous with respect to the polypeptide encoded by the gene, and can optionally be derived from a different species that the species from which the encoded polypeptide is derived. In some embodiments the terminator may be derived from the same species as at least one or all of the at least three or at least four heterologous introns. In some embodiments the terminator may be derived from the same species as a promoter operably linked to the engineered gene.

Expression Cassettes

Expression cassettes are also provided in the present invention, in which the expression cassettes comprise one or more regulatory elements as described herein to drive the expression of transgenes. These cassettes comprise isolated nucleic acid molecules that include any one of the promoter sequences described herein or any combination thereof, operably linked to a gene of interest, with the gene of interest positioned downstream of the promoter sequence, and optionally with any one of the terminator sequences described herein or any combination thereof operably linked downstream of the transgene. For example, any of the promoters listed in Table 1, or promoters comprising sequences having at least 80% identity to subsequences of any of the promoter of Table 1 as described herein, can be used in combination with any terminator listed in Table 1, or terminators comprising sequences having at least 80% identity to subsequences thereof as described herein, in an expression cassette.

The basic techniques for operably linking two or more sequences of DNA together are familiar to the skilled worker, and such methods have been described in a number of texts for standard molecular biological manipulation (see, e.g., "Molecular Cloning: A Laboratory Manual," 2nd ed. Cold Spring Harbor Laboratory Press, Cold Spring Harbor, N.Y.; Gibson et al. (2009) Nature Methods 6:343-345).

The promoters of the invention can be used with any heterologous or homologous gene(s). A heterologous or homologous gene according to the invention may encode a protein or polypeptide. Alternatively, the heterologous or homologous gene can encode a functional RNA, such as a tRNA, rRNA, small nucleolar RNA (snoRNA), ribozyme, antisense RNA (asRNA), micro RNA (miRNA), short hairpin RNA (shRNA), small interfering RNA (siRNA), piwi-interacting RNA (piRNA), transactivator RNA (tracrRNA), or a guide RNA of a CRISPR system (gRNA). A guide RNA can optionally be a chimeric guide RNA that includes a tracr sequences. Any known or later-discovered heterologous or homologous gene which encodes a desired product can be operably linked to a promoter sequence of the invention using known methods. Non-limiting examples of known genes suitable for use with the promoters of the invention include genes encoding proteins associated with lipid biosynthesis; lipases; proteins associated with carbohydrate metabolism; transporter polypeptides; proteins conferring resistance to an antibiotic, herbicide, or toxin; reporter proteins (e.g., fluorescent proteins or enzymes that produce detectable products) polypeptides of the Calvin-Benson cycle; polypeptides that participate in photosynthesis (such as but not limited to, photosynthetic reaction center polypeptides, light-harvesting chlorophyll-binding proteins, oxygen-evolving complex polypeptides, cytochromes, ferredoxins, etc.); dehydrogenases, such as NADPH-forming dehydrogenases; transcription factors; proteins involved in cell signaling (e.g., G proteins or kinases); or functional RNAs.

For example, an expression cassette can comprise a promoter as described herein (for example, a promoter comprising a nucleotide sequence having at least 80% identity to at least 100 contiguous nucleotides of SEQ ID NO:1, SEQ ID NO:4, SEQ ID NO:8, SEQ ID NO:11, SEQ ID NO:13, SEQ ID NO:15, SEQ ID NO:17, SEQ ID NO:19, SEQ ID NO:21, or SEQ ID NO:23) operably linked to a gene encoding a polypeptide, where the polypeptide can be any polypeptide of interest, and in illustrative and nonlimiting examples, can be a protein associated with lipid biosynthesis, an acetyl-CoA carboxylase, a malonyl type 1 fatty acid synthase, a type 2 fatty acid synthase subunit, a beta ketoacyl-ACP synthase, a malonyl-CoA-malonyl-ACP acyltransferase, an acyl-ACP thioesterase, an acyl-CoA thioesterase, a 4-hydroxybenzoyl thioesterase, an alcohol forming acyl reductase, a wax synthase, an aldehyde decarbonylase, a fatty acid decarboxylase, a lipase, a glyceraldehyde 3 phosphate dehydrogenase, an acyl-CoA synthetase, a phospholipid diacylglycerol acyltransferase, a glycerol 3 phosphate acyltransferase, a lysophosphatidic acid acyltransferase, a phosphatidic acid phosphatase, a diacyl glycerol acyltransferase, a polypeptide that participates in photosynthesis, a chlorophyll-binding light harvesting polypeptide, a photosynthetic reaction center polypeptide, an oxygen-evolving complex polypeptide, a cytochrome, a ferredoxin, a protein associated with carbon fixation, a ribulose bisphoshate carboxylase subunit, a carbonic anhydrase, a transporter protein, an ABC transporter, a FatB transporter, a dehydrogenase, an aldehyde dehydrogenase, a 2-hydroxyacid dehydrogenase, an isocitrate dehydrogenase, 6 phosphogluconate dehydrogenase, glucose 6 phosphate dehydrogenase, a transcription factor, a kinase, or a G protein.

In further examples, an expression cassette can comprise a promoter as described herein (for example, a promoter comprising a nucleotide sequence having at least 80% identity to at least 100 contiguous nucleotides SEQ ID NO:1, SEQ ID NO:4, SEQ ID NO:8, SEQ ID NO:11, SEQ ID NO:13, SEQ ID NO:15, SEQ ID NO:17, SEQ ID NO:19, SEQ ID NO:21, or SEQ ID NO:23) operably linked to a gene encoding a functional RNA, optionally wherein the functional RNA is an antisense RNA, a small hairpin RNA, a microRNA, an siRNA, an snoRNA, a piRNA, or a ribozyme.

An expression cassette as provided herein can further include a terminator, such as but not limited to a terminator as disclosed herein. In some embodiments an expression cassette can include a promoter and terminator that are both heterologous with respect to the polypeptide or functional RNA-encoding sequence of the expression cassette. The promoter and terminator of an expression cassette can optionally be derived from the same genus or species, and can further optionally be derived from the same gene. In certain embodiments a promoter and terminator of an expression cassette can be derived from *Parachlorella* genes and may be derived from the same *Parachlorella* gene An expression cassette as provided herein can optionally include an intronylated gene that includes one or more heterologous introns, as described above, i.e., introns that are not native to the gene from which the protein or functional RNA-encoding sequences are derived. One or more heterologous introns of an engineered gene of an expression cassette can be derived from the same species as the promoter operably linked to the engineered gene. One or more heterologous introns of an engineered gene of an expression cassette can be derived from the same gene as the promoter operably linked to the engineered gene. The expression cassette can further include a terminator operably linked to the engineered gene that is derived from the same species as the one or more heterologous introns and the promoter operably linked to the engineered gene. The terminator can optionally be derived from the same gene as the one or more heterologous introns and the promoter operably linked to the engineered gene. In particular embodiments, the operably linked promoter and terminator and all of the introns of an engineered gene are derived from the same gene. In some embodiments the promoter, terminator, and introns of an engineered gene are derived from the same gene of an algal species, which is exemplary embodiments can be the RPS4 gene or FBPase gene of an algal species.

Vectors

The present invention also provides vectors that can comprise the regulatory elements and/or expression cassettes described herein. The vectors can further optionally comprise at least one origin of replication ("ORI") sequence for replication in a cell. The vectors may further optionally comprise one or more selectable markers under the control of one or more eukaryotic promoters, one or more selectable markers under the control of one or more prokaryotic promoters, and/or one or more sequences that mediate recombination of an exogenous nucleic acid sequence into the target cell's genome.

An ORI is the sequence in a DNA molecule at which replication begins. The ORI serves as a base of assembly for the pre-replication complex. Depending on the ORI, such replication can proceed unidirectionally or bidirectionally. An expression vector as provided herein can include an ORI for replication of the expression vector in a cloning host, such as *E. coli* or *Saccharomyces*, and/or can include an ORI for replication of the expression vector in a target cell, which can be, for example, an algal or chlorophyte cell. The structural biology of ORIs is widely conserved among prokaryotes, eukaryotes, and viruses. Most ORIs possess simple tri-, tetra-, or higher nucleotide repetition patterns. Most are AT-rich and contain inverted repeats. Those skilled in the art will be familiar with the more common ORIs, such as p15A and the pUC ORI.

Additionally, a vector described herein may also carry a selectable marker. By way of example, a vector that includes an expression cassette may include, as a selectable marker, a gene conferring resistance to a poison, such as an antibiotic, an herbicide, or some other toxin, so that transformants can be selected by exposing the cells to the poison and selecting those cells which survive the encounter. Non-limiting examples of selectable markers include: 1) genes conferring resistance to antibiotics such as amikacin (aphA6), ampicillin (ampR), blasticidin (bls, bsr, bsd), bleomicin or phleomycin (ZEOCIN™) (ble), nourseothricin (nail), chloramphenicol (cat), emetine (RBS14p or cry1-1), erythromycin (ermE), G418 (GENETICIN™) (neo), gentamycin (aac3 or aacC4), hygromycin B (aphIV, hph, hpt), kanamycin (nptII), methotrexate (DHFR mtxR), penicillin and other β-lactams (β-lactamases), streptomycin or spectinomycin (aadA, spec/strep), and tetracycline (tetA, tetM, tetQ); 2) genes conferring resistance or tolerance to herbicides such as aminotriazole, amitrole, andrimid, aryloxyphenoxy propionates, atrazines (psbA), bipyridyliums, bromoxynil, cyclohexandione oximes dalapon, dicamba, diclfop, dichlorophenyl dimethyl urea (DCMU), difunone, diketonitriles, diuron, fluridone, glufosinate, glyphosate, halogenated hydrobenzonitriles, haloxyfop, 4-hydroxypyridines, imidazolinones, isoxasflutole, isoxazoles, isoxazolidinones, mioamide B, p-nitrodiphenylethers, norflurazon, oxadiazoles, m-phenoxybenzamides, N-phenyl imides, pinoxadin, protoporphyrionogen oxidase inhibitors, pyridazinones, pyrazolinates, sulfonylureas, 1,2,4-triazol pyrimidine, triketones, urea compounds; acetyl CoA carboxylase (ACCase), acetohydroxy acid synthase (ahas), acetolactate synthase (als, csr1-1, csr1-2, imr1, imr2), aminoglycoside phosphotransferase (apt), anthranilate synthase, bromoxynil nitrilase (bxn), cytochrome P450-NADH-cytochrome P450 oxidoreductase, dalapon dehalogenase (dehal), dihydropteroate synthase (sul), class I 5-enolpyruvylshikimate-3-phosphate synthase (EPSPS), class II EPSPS (aroA), non-class I/II EPSPS, glutathione reductase, glyphosate acetyltransferase (gat), glyphosate oxidoreductase (gox), hydroxyphenylpyruvate dehydrogenase, hydroxy-phenylpyruvate dioxygenase (hppd), isoprenyl pyrophosphate isomerase, lycopene cyclase, phosphinothricin acetyl transferase (pat, bar), phytoene desaturase (crtI), prenyl transferase, protoporphyrin oxidase, psbA of photosystem II (psbA), and SMM esterase (SulE) superoxide dismutase (sod); and/or 3) genes that may be used in auxotrophic strains or to confer autotrophic growth or other metabolic effects, such as arg7, his3, hisD, hisG, lysA, manA, metE, nitl, trpB, ura3, xylA, a dihydrofolate reductase gene, a mannose-6-phosphate isomerase gene, a nitrate reductase gene, or an ornithine decarboxylase gene; a negative selection factor such as thymidine kinase; or toxin resistance factors such as a 2-deoxyglucose resistance gene.

The selectable marker gene can be operably linked to and/or under the control of a promoter as provided herein. The promoter regulating expression of the selectable marker may be conditional or inducible but is preferably constitutive, and can be, for example, any promoter disclosed herein or another promoter. Alternatively, the selectable marker may be placed under the control of the expression cassette promoter. If a selectable marker is placed under the control of the expression cassette promoter, the selectable marker and the expression cassette may be operably linked with an internal ribosome entry site ("IRES") element between the expression cassette and the selectable marker (Komar & Hatzoglou (2011) Cell Cycle 10:229-240 and Hellen & Sarnow (2001) Genes & Dev. 15:1593-1612, incorporated by reference in their entireties) or a "2A" sequence (Kim et al. (2011) PLoS One 6(4):e18556, incorporated by reference in its entirety).

Further provided herein is a vector for transformation of a eukaryotic cell, such as but not limited to a eukaryotic microalgal cell or phytoplankter cell, in which the vector includes a selectable marker gene operably linked to a promoter as provided herein, for example, a promoter that includes a nucleotide sequence having at least 80%, at least 85%, at least 90%, at least 95%, at least 96%, at least 97%, at least 98%, at least 99%, or about 100% identity to at least 100, at least 200, at least 300, at least 400, at least 500, at least 600, at least 700, or at least 800 contiguous nucleotides of SEQ ID NO:1, SEQ ID NO:4, SEQ ID NO:8, SEQ ID NO:11, SEQ ID NO:13, SEQ ID NO:15, SEQ ID NO:17, SEQ ID NO:19, SEQ ID NO:21, or SEQ ID NO:23, or a promoter that comprises SEQ ID NO:1, SEQ ID NO:4, SEQ ID NO:8, SEQ ID NO:11, SEQ ID NO:13, SEQ ID NO:15, SEQ ID NO:17, SEQ ID NO:19, SEQ ID NO:21, or SEQ ID NO:23. The transformation vector can further include one or more additional genes or constructs for transfer into the host cell, such as a gene encoding a polypeptide such as but not limited to any disclosed hereinabove or a construct encoding a functional RNA, where the gene encoding a polypeptide or functional RNA can optionally be operably linked to a promoter as described herein, or can optionally be operably linked to another promoter.

Additionally or alternatively, the vectors as provided herein may comprise a terminator as provided herein. For example, a vector of the present invention may comprise a nucleotide sequence having at least 80%, at least 85%, at least 90%, at least 95%, at least 96%, at least 97%, at least 98%, at least 99%, or about 100% identity to at least 100, at least 200, at least 300, at least 400, at least 500, at least 600, at least 700, or at least 800 contiguous nucleotides of SEQ ID NO:7, SEQ ID NO:9, SEQ ID NO:12, SEQ ID NO:14, SEQ ID NO:16, SEQ ID NO:18, SEQ ID NO:20, SEQ ID NO:22, or SEQ ID NO:24. A gene of interest or a selectable marker gene on a vector of the present invention may be operably linked to a terminator sequence as provided herein. For example, a gene of interest or a selectable marker may be operably linked to SEQ ID NO:7, SEQ ID NO:9, SEQ ID NO:12, SEQ ID NO:14, SEQ ID NO:16, SEQ ID NO:18, SEQ ID NO:20, SEQ ID NO:22, or SEQ ID NO:24.

In an alternative transformation strategy, a selectable marker operably linked to a promoter such as a promoter described herein can be provided on a separate construct, where both the gene-of-interest construct and the selectable marker construct are used together in transformation protocols. Selected transformants are then analyzed for co-transformation of the construct that includes the gene-of-interest (see, e.g., Kindle (1990) *Proc. Nat'l. Acad. Sci.* USA 87:1228-1232).

If a vector as provided herein that includes an expression cassette lacks a selectable marker gene, transformants may be selected by routine methods familiar to those skilled in the art, such as, by way of a non-limiting example, extracting nucleic acid from the putative transformants and screening by PCR. Alternatively or in addition, transformants may be screened by detecting expression of a reporter gene, such as but not limited to a chloramphenicol acyltransferase gene (cat) lacZ, uidA, xylE, an alkaline phosphatase gene, an α-amylase gene, an α-galactosidase gene, a β-lactamase gene, a β-glucuronidase gene, a horseradish peroxidase gene, a luciferin/luciferase gene, an R-locus gene, a tyrosinase gene, or a gene encoding a fluorescent protein, such as any of the blue, cyan, green, red, yellow, photoconvertible, or photoswitchable fluorescent proteins or any of their variants, including codon-optimized, rapidly folding, monomeric, increased stability, and enhanced fluorescence variants. A reporter gene used in a vector may optionally be regulated by a promoter as provided herein. A transformation vector may include a gene encoding a reporter, such as, for example, a fluorescent protein, operably linked to a promoter as provided herein.

In some examples, the vector is designed for integration of one or more genes (such as the expression cassette) into the host genome. For example, the expression vectors may include *Agrobacterium* flanking sequences designed for integrating transgenes into the genome of a target plant cell. In other embodiments, vectors can be targeted for integration into a plant or algal chromosome by including flanking sequences that enable homologous recombination into the chromosome or targeted for integration into endogenous host plasmids by including flanking sequences that enable homologous recombination into the endogenous plasmids. In some cases in which it may be advantageous to transform the chloroplast of a higher plant or alga, the expression vectors can be designed to have regions of sequences flanking the transgene that are homologous to chloroplast sequences to promote homologous recombination and integration of the sequence of interest. Further, a transformation vector can include sequences for site-specific recombination such as but not limited to lox sites on which the cre recombinase acts.

In addition to the promoters provided herein, one skilled in the art would know various promoters, introns, enhancers, transit peptides, targeting signal sequences, 5' and 3' untranslated regions (UTRs), IRES, 2A sequences, and terminator sequences, as well as other molecules involved in the regulation of gene expression that are useful in the design of effective expression vectors. In some embodiments, the expression vector will contain one or more enhancer elements Enhancers are short regions of DNA that can bind trans-acting factors to enhance transcription levels. Although enhancers usually act in cis, an enhancer need not be particularly close to its target gene, and may sometimes not be located on the same chromosome Enhancers can sometimes be located in introns.

In some examples, a gene or genes encoding enzymes that participate in the synthesis of a fatty acid product (e.g., a fatty acid, a fatty acid derivative, or a glycerolipid) is cloned into the vector as an expression cassette that includes a promoter as disclosed herein. The expression cassette may optionally include a transit peptide-encoding sequence for directing the expressed enzyme to the chloroplast or endoplasmic reticulum of transformed eukaryotic cells, an intron sequence, a sequence having a poly-adenylation signal, etc. Additionally or alternatively, a vector is provided comprising an expression cassette as described herein, wherein the vector further comprises one or more of: a selectable marker gene, an origin of replication, and one or more sequences for promoting integration of the expression cassette into the host genome. Additionally or alternatively, a vector is provided comprising an isolated or recombinant nucleic acid molecule as described herein, wherein the isolated nucleic acid molecule is operably linked to a nucleic acid sequence encoding a selectable marker or a reporter protein, such as, for example, any described herein. In a particular embodiment, the vector further comprises one or more of: an origin of replication, one or more sequences for promoting integration of the expression cassette into the host genome, a sequence as reported herein that comprises a terminator, or an additional gene, wherein the additional gene encodes an antisense RNA, a microRNA, an shRNA, a ribozyme, structural protein, an enzyme, a transcription factor, or a transporter.

Transformation Methods

The present invention also provides transformation methods in which a eukaryotic cell is transformed with an expression vector as described herein. The methods comprise introducing an expression vector as provided herein that includes at least one promoter as provided herein and then selecting for a transformant. The expression vector may be introduced by many methods familiar to those skilled in the art including, as non-limiting examples: natural DNA uptake (Chung et al. (1998) *FEMS Microbiol. Lett.* 164:353-61); conjugation (Wolk et al. (1984) *Proc. Nat'l. Acad. Sci. USA* 81, 1561-65); transduction; glass bead transformation (Kindle et al. (1989) *J. Cell Biol.* 109:2589-601); silicon carbide whisker transformation (Dunahay et al. (1997) *Methods Mol. Biol.* (1997) 62:503-09); biolistics (Dawson et al. (1997) *Curr. Microbiol.* 35:356-62); electroporation (Kjaerulff et al. (1994) *Photosynth. Res.* 41:277-83); laser-mediated transformation; or incubation with DNA in the presence of or after pre-treatment with any of poly(amidoamine) dendrimers (Pasupathy et al. (2008) *Biotechnol. J.* 3:1078-82), polyethylene glycol (Ohnuma et al. (2008) *Plant Cell Physiol.* 49:117-20), cationic lipids (Muradawa et al. (2008) *J. Biosci. Bioeng.* 105:77-80), dextran, calcium phosphate, or calcium chloride (Mendez-Alvarez et al. (1994) *J. Bacteriol.* 176:7395-97), optionally after treatment of the cells with cell wall-degrading enzymes (Perrone et al. (1998) *Mol. Biol. Cell* 9:3351-65). *Agrobacterium*-mediated transformation can also be performed on algal cells, for example after removing or wounding the algal cell wall (e.g., WO 2000/62601). Biolistic methods have been shown to be successful for transformation of the chloroplasts of plant and eukaryotic algal species (see, e.g., WO 2007/133558, incorporated by reference in its entirety). When transforming chloroplasts, it can be useful to codon-optimize the gene of interest for expression in chloroplasts (see, e.g., WO 2011/034863, incorporated by reference in its entirety).

The eukaryotic cell transformed can be, for example, a fungal, heterokont, chlorophyte, algal, or plant cell. For example, the eukaryotic cell transformed using an expression vector as provided herein can be an algal cell, such as a species of *Achnanthes, Amphiprora, Amphora, Ankistrodesmus, Asteromonas, Boekelovia, Bolidomonas, Borodinella, Botrydium, Botryococcus, Bracteococcus, Chaetoceros, Carteria, Chlamydomonas, Chlorococcum, Chlorogonium, Chlorella, Chroomonas, Chrysosphaera, Cricosphaera, Crypthecodinium, Cryptomonas, Cyclotella, Dunaliella, Ellipsoidon, Emiliania, Eremosphaera, Ernodesmius, Euglena, Eustigmatos, Franceia, Fragilaria, Gloeothamnion, Haematococcus, Halocafeteria, Heterosigma, Hymenomonas, Isochrysis, Lepocinclis, Micractinium, Monoraphidium, Nannochloris, Nannochloropsis, Navicula, Neochloris, Nephrochloris, Nephroselmis, Nitzschia, Ochromonas, Oedogonium, Oocystis, Ostreococcus, Pavlova, Parachlorella, Pascheria, Pelagomonas, Phae-* odactylum, Phagus, Picochlorum, Platymonas, Pleurochrysis, Pleurococcus, Prototheca, Pseudochlorella, Pseudoneochloris, Pseudostaurastrum, Pyramimonas, Pyrobotrys, Scenedesmus, Skeletonema, Spyrogyra, Stichococcus, Tetraselmis, Thalassiosira, Tribonema, Vaucheria, Viridiella, Vischeria, and Volvox. For example, the eukaryotic cell transformed using the methods provided herein can optionally be a species of Parachlorella, such as non-limiting examples: Parachlorella kessieri, P. hussii, P. beijerinckii, P. sp. CCAP 206/1, or P. sp. pgu003.

In further examples, the eukaryotic cell can be an alga of the Chlorophyceae, Trebouxiophyceae, or Prasinphyceae class. In some embodiments, the herein disclosed electroporation method is a method of transforming a species of the Trebouxiophyceae class, such as, for example, a species of a genus such as Actinastrum, Amphikorikos, Asterochloris, Auxenochlorella, Botryococcus, Chlorella, Choricystis, Coccomyxa, Coenocystis, Closteriopsis, Diacanthos, Dicloster, Dictyosphaerium, Dictoyochloropsis, Didymogenes, Diplosphaera, Eremosphaera, Franceia, Fusochloruis, Gloeotila, Helicosporidium, Heveochlorella, Koliella, Koriellopsis, Lagerheimia, Leptosira, Loboshpaera, Makinoella, Marvania, Muriella, Meyrella, Marinichlorella, Microthamnion, Micractinium, Myrmecia, Nannochloris, Oocystis, Pabia, Parachlorella, Paradoxia, Parietochloris, Picochlorum, Prasiola, Prasiococcus, Prasiolopsis, Prototheca, Pseudochlorella, Pseudotrebouxia, Raphidonema, Rosssenvingiella, Stichococcus, Tetrachlorella, Trebouxia, Trichophilus, Viridiella, or Watanabea. In some aspects, the herein disclosed method can be used to transform a species belonging to the genus of Botryococcus, Chlorella, Eremosphaera, Franceia, Micractinium, Nannochloris, Oocystis, Parachlorella, Picochlorum, Prototheca, or Pseudochlorella. In some aspects, the transformed cell can be a species belonging to the genus of Auxenochlorella, Chlorella, Heveochlorella, Marinichlorella, Parachlorella, Pseudochlorella or Tetrachlorella. For example, the cell transformed using the methods provided herein can optionally be a species of Parachlorella, such as non-limiting examples: Parachlorella kessieri, P. hussii, P. beijerinckii, P. sp. CCAP 206/1, or P. sp. pgu003.

In some examples, a Parachlorella cell is transformed by electroporation or particle bombardment. The expression vector used to transform the host cell may encode, for a selectable marker, a ble gene conferring bleomycin resistance, a bsd gene conferring blasticidin resistance, a green fluorescent protein gene, a polypeptide, or a functional RNA.

Additionally or alternatively, a Parachlorella cell is transformed by a biolistic method. For example, the transformation may be achieved by use of a gene gun. By way of example, the gene gun may employ a rupture disc of 1100 rps, of 1350 rps, of 1550 rps, of 1800 rps, or of 2000 rps. A biolistic transformation of the present invention may involve any amount of DNA coated particles per bombardment; for example, a biolistic transformation method of the present invention may employ 1 µg, 2 µg, 3 µg, 4 µg, 5 µg, 6 µg, 7 µg, 8 µg, 9 µg, 10 µg, 20 µg, 30 µg, 40 µg, 50 µg, 100 µg, 150 µg, 200 µg, 300 µg, 400 µg, 500 µg, 1 mg, 2 mg, or 3 mg of DNA coated particles per bombardment. Additionally or alternatively, the DNA coated particles may be deployed using at least about 300 psi. For example, the gene gun can be fired using at least 300 psi, at least 350 psi, at least 400 psi, at least 450 psi, at least 500 psi, at least 550 psi, at least 600 psi, at least 650 psi, or at least 700 psi.

The distance between a microcarrier and a plate in a biolistic transformation method of the present invention may vary according to the construct being transformed into a cell and the cells; for example the distance may be approximately 3 cm, approximately 4 cm, approximately 5 cm, approximately 6 cm, approximately 7 cm, approximately 8 cm, or even approximately 9 cm. A microcarrier used in a biolistic method of the present invention may be in either the top position or bottom position, depending on the construct being transformed into a cell and the cells. DNA used in a biolistic method of the present invention may be linearized by restriction enzyme digest or may be circular supercoiled plasmid DNA, depending on the construct being transformed into a cell and the cells. Cells grown for use in a biolistic method of the present invention may be grown in a variety of culture conditions; for example, cells destined for bombardment in a biolistic method of the present invention may be grown in PM024 liquid media or on PM024 agar plates for 2 days prior to bombardment. Cells used in a biolistic method of the present invention may be in different phases of a 14:10 diel cycle; for example, cells may be in either a light phase or dark phase, depending on the construct being transformed into a cell and the cells. A variety of antibiotic concentrations may be used to select transformants after transformation by a biolistic method of the present invention. One skilled in the art will recognize that these parameters are all subject to routine optimization involving only limited experimentation.

Transformation of WT-1185 was also achieved by electroporation using a procedure as describe herein. To prepare culture for transformation, a 100 mL seed culture inoculated to $1 \times 10^{6}$ cells/mL six days before transformation was used to inoculate a 1 L culture to $1 \times 10^{6}$ cells/mL two days before transformation. On the day of transformation, cells were pelleted by centrifugation at 5000×g for 20 minutes, washed three times with 0.1 um filtered 385 mM sorbitol, and resuspended to $5 \times 10^{9}$ cells/mL in 385 mM sorbitol. Electroporation of 100 uL concentrated cells was performed in 0.2 cm cuvettes in a BioRad Gene Pulser Xcell™ under varied conditions Immediately after electroporating pre-chilled cells and cuvettes, 1 mL cold sorbitol was added and used to transfer cells into 10 mL PM074. After overnight recovery, cells were concentrated and spread onto 13 cm-diameter PM074 media containing zeocin at 250 mg/L and grown under the conditions listed in the biolistics section.

Additionally or alternatively, a Parachlorella cell is transformed by an electroporation method. For example, the transformation may be achieved by use of an electroporator. By way of example, using a 0.2 cm cuvette, the electroporator can be set to output approximately 0.5 kilovolts (kV), 0.6 kV, 0.7 kV, 0.8 kV, 0.9 kV, 1.0 kV, 1.1 kV, 1.2 kV, 1.3 kV, 1.4 kV, 1.5 kV, or 1.6 kV. Additionally or alternatively, successful electroporation can be achieved with at least 0.5 kilovolts (kV), at least 0.6 kV, at least 0.7 kV, at least 0.8 kV, at least 0.9 kV, at least 1.0 kV, at least 1.1 kV, at least 1.2 kV, at least 1.3 kV, at least 1.4 kV, at least 1.5 kV, at least 1.6 kV, or with between 0.5 kV and 1.7 kV, or between 0.6 kV and 1.6 kV, or between 0.7 kV and 1.5 kV, or between 0.9 kV and 1.5 kV, or between 1.0 kV and 1.2 kV. By way of example, the electroporator can be set to output a field strength of approximately 250 kilovolts per meter (kV/m), 300 kV/m, 350 kV/m, 400 kV/m, 450 kV/m, 500 kV/m, 550 kV/m, 600 kV/m, 650 kV/m, 700 kV/m, 750 kV/m, or 800 kV/m, or for example, with at least 250 kV/m, at least 300 kV/m, at least 350 kV/m, at least 400 kV/m, at least 450 kV/m, at least 500 kV/m, at least 550 kV/m, at least 600 kV/m, at least 650 kV/m, at least 700 kV/m, at least 750 kV/m, or at least 800 kV/m. In some examples, successful electroporation can be achieved with between 250 kV/m and 850 kV/m, or between 300 kV/m and 800 kV/m, or between 700 kV/m and 750 kV/m, or between 450 kV/m and 750 kV/m, or between 500 kV/m and 600 kV/m. Additionally or alternatively, successful electroporation can be achieved with resistances of approximately 100 Ohms, 200 Ohms, 300 Ohms, or 400 Ohms. Additionally or alternatively, successful electroporation can be achieved with a resistance setting of at least 100 Ohms, at least 200 Ohms, or at least 300 Ohm, for example, with a resistance setting between 100 Ohms and 400 Ohms, between 200 Ohms and 400 Ohms, between 200 Ohms and 300 Ohms, or between 300 Ohms and 400 Ohms. Additionally or alternatively, successful electroporation can be achieved with a capacitance of approximately 10 µF, 25 µF, 50 µF, at least 10 µF, at least 25 µF, or at least 50 µF. For example, the capacitance can be between 10 µF and 50 µF, or between 25 µF and 50 µF. Successful electroporation can be achieved using approximately 0.5 µg, 1 µg, 2 µg, 3 µg, 4 µg, 5 µg, 6 µg, 7 µg, or 8 µg of DNA. In various examples, successful electroporation can be achieved with between 0.5 µg and 8 µg of DNA, between 1 µg and 8 µg of DNA, or between 2 µg and 8 µg of DNA. In an exemplary embodiment the optimal electroporation conditions are a field strength between 500 kV/m and 600 kV/m, and a resistance between 200 Ohms and 300 Ohms, and a capacitance between 25 µF and 50 µF.

In some embodiments, the herein disclosed electroporation method is a method of transforming a species of the Trebouxiophyceae class. In some aspects, the herein disclosed method can be used to transform a species belonging to the genus of *Botryococcus, Chlorella, Eremosphaera, Franceia, Micractinium, Nannochloris, Oocystis, Parachlorella, Picochlorum, Prototheca,* or *Pseudochlorella*. In some aspects, the transformed cell can be a species belonging to the genus of *Chlorella, Parachlorella,* or *Pseudochlorella*. For example, the cell transformed using the methods provided herein can optionally be a species of *Parachlorella,* such as non-limiting examples: *Parachlorella kessieri, P. hussii, P. beijerinckii, P.* sp. CCAP 206/1, or *P.* sp. pgu003.

Culture

Eukaryotic host cells, such as any of the cells disclosed hereinabove transformed with the expression vectors are also provided herein. Transformed algal cell cultures can be diluted, plated on agar, and allowed to grow until isolated colonies can be selected for further propagation as clonal strains.

Therefore, in one embodiment a eukaryotic cell is provided comprising an isolated or recombinant nucleic acid molecule as described herein or an expression cassette as described herein, or a vector as described herein.

Algae can be cultured phototrophically, in the absence of a fixed carbon source, or mixotrophically, where the cultures are supplied with light for at least part of the day, and also supplied with a reduced carbon source, such as a sugar (e.g., glucose, fructose, galactose, mannose, rhamnose, arabinose, xylose, lactose, sucrose, maltose), an organic acid (e.g., acetate, citrate, succinate), or glycerol.

Additionally, a photosynthetic organism can be cultured mixotrophically, in which the organism is grown in the presence of light for at least a part of the day, and also provided with one or more sources of reduced carbon. The photosynthetic organism can be grown mixotrophically for a period of time, followed by a period of phototrophic growth, or vice versa.

Media for phototrophic or mixotrophic growth of algae are known in the art, and media can be optimized to enhance growth or production of fatty acid products for a particular species. Artificial light sources can be used as the sole light source or to enhance or extend natural light.

Growth of algae can be in open areas, such as, for example, ponds, canals, channels, raceways, or tanks, or can be in bioreactors. Bioreactors are preferred for mixotrophic growth, and can also be used for phototrophic growth. The bioreactors can be of any sizes and form, and can include inlets for providing nutrients, additives, or gases, such as but not limited to air or $CO_2$. A bioreactor preferably also has an outlet for sampling of the culture. A bioreactor can be configured such that the algal culture is mixed during the growth period, for example, by stirring, rocking, shaking, inverting, bubbling of gases through the culture, etc. Outdoor ponds, raceways, tanks, canals, etc. can also be designed for mixing of cultures through, for example, paddles, pumps, hoses or jets for circulation of the culture media, or tubes, hoses or inlets for supplying air or $CO_2$ to the culture.

Methods of Producing Algal Products

Also provided herein are methods of producing algal products by culturing recombinant algae disclosed herein. The methods include culturing a recombinant algal mutant in a suitable medium to provide an algal culture and recovering biomass or at least one product from the culture. The algal culture is preferably a photoautotrophic culture, and the culture medium preferably does not include a substantial amount of reduced carbon, that is, the culture does not include reduced carbon in a form or at a level that can be used by the algae for growth.

The algae may be cultured in any suitable vessel, including flasks or bioreactors, where the algae may be exposed to artificial or natural light. The culture comprising recombinant mutant algae may be cultured on a light/dark cycle that may be, for example, a natural or programmed light/dark cycle, and as illustrative examples, may provide twelve hours of light to twelve hours of darkness, fourteen hours of light to ten hours of darkness, sixteen hours of light to eight hours of darkness, etc.

Culturing refers to the intentional fostering of growth (e.g., increases in cell size, cellular contents, and/or cellular activity) and/or propagation (e.g., increases in cell numbers via mitosis) of one or more cells by use of selected and/or controlled conditions. The combination of both growth and propagation may be termed proliferation. As demonstrated in the examples herein, the recombinant mutants provided herein can achieve higher cell density of the culture over time, for example, over a period of a week or more, with respect to a culture wild type algal cells of the same strain. For example, a recombinant mutant may be cultured for at least five, at least six, at least seven at least eight, at least nine, at least ten, at least eleven at least twelve, at least thirteen, at least fourteen, or at least fifteen days, or at least one, two three, four, five, six, seven, eight, nine, or ten weeks, or longer.

Non-limiting examples of selected and/or controlled conditions that can be used for culturing the recombinant alga can include the use of a defined medium (with known characteristics such as pH, ionic strength, and/or carbon source), specified temperature, oxygen tension, carbon dioxide levels, growth in a bioreactor (e.g. a photobioreactor), or the like, or combinations thereof. In some embodiments, the alga or host cell can be grown mixotrophically, using both light and a reduced carbon source. Alternatively, the alga or host cell can be cultured phototrophically. When growing phototrophically, the algal strain can advantageously use light as an energy source. An inorganic carbon source, such as CO2 or bicarbonate can be used for synthesis of biomolecules by the alga. "Inorganic carbon", as used herein, includes carbon-containing compounds or molecules that cannot be used as a sustainable energy source by an organism. Typically "inorganic carbon" can be in the form of CO2 (carbon dioxide), carbonic acid, bicarbonate salts, carbonate salts, hydrogen carbonate salts, or the like, or combinations thereof, which cannot be further oxidized for sustainable energy nor used as a source of reducing power by organisms. Algae grown photoautotrophically can be grown on a culture medium in which inorganic carbon is substantially the sole source of carbon. For example, in a culture in which inorganic carbon is substantially the sole source of carbon, any organic (reduced) carbon molecule or organic carbon compound that may be provided in the culture medium either cannot be taken up and/or metabolized by the cell for energy and/or is not present in an amount sufficient to provide sustainable energy for the growth and proliferation of the cell culture. Cells grown photoautrophically can be grown under constant light or a diel cycle, for example a diel cycle in which the light period can be, for example, at least four hours, about five hours, about six hours, about seven hours, about eight hours, at least eight hours, about nine hours, about ten hours, about eleven hours, about twelve hours, about thirteen and a half hours, or up to about sixteen hours per day, for example, between about twelve hours and about fourteen hours, or between about fourteen hours and about sixteen hours.

Algae and host cells that can be useful in accordance with the methods of the present disclosure can be found in various locations and environments throughout the world. The particular growth medium for optimal propagation and generation of lipid and/or other products can vary and may be optimized to promote growth, propagation, or production of a product such as a lipid, protein, pigment, antioxidant, etc. In some cases, certain strains of algae may be unable to grow in a particular growth medium because of the presence of some inhibitory component or the absence of some essential nutritional requirement of the particular strain of alga or host cell.

Solid and liquid growth media are generally available from a wide variety of sources, as are instructions for the preparation of particular media suitable for a wide variety of strains of algas. For example, various fresh water and salt water media can include those described in Barsanti (2005) Algae: Anatomy, Biochemistry & Biotechnology, CRC Press for media and methods for culturing algae. Algal media recipes can also be found at the websites of various algal culture collections, including, as nonlimiting examples, the UTEX Culture Collection of Algae (www.sbs.utexas.edu/utex/media.aspx); Culture Collection of Algae and Protozoa (www.ccap.ac.uk); and Katedra Botaniky (botany.natur.cuni.cz/algo/caup-media.html).

The culture methods can optionally include inducing expression of one or more genes for the production of a product, such a but not limited to a protein that participates in the production of a lipid, one or more proteins, antioxidants, or pigments, and/or regulating a metabolic pathway in the alga. Inducing expression can include adding a nutrient or compound to the culture, removing one or more components from the culture medium, increasing or decreasing light and/or temperature, and/or other manipulations that promote expression of the gene of interest. Such manipulations can largely depend on the nature of the (heterologous) promoter operably linked to the gene of interest.

In some embodiments of the present disclosure, the recombinant algae can be cultured in a photobioreactor equipped with an artificial light source, and/or having one or more walls that is transparent enough to light, including sunlight, to enable, facilitate, and/or maintain acceptable alga growth and proliferation. For production of fatty acid products or triglycerides, photosynthetic algae or host cells can additionally or alternately be cultured in shake flasks, test tubes, vials, microtiter dishes, petri dishes, or the like, or combinations thereof.

Additionally or alternately, recombinant photosynthetic alga or host cells may be grown in ponds, canals, sea-based growth containers, trenches, raceways, channels, or the like, or combinations thereof. In such systems, the temperature may be unregulated, or various heating or cooling method or devices may be employed. As with standard bioreactors, a source of inorganic carbon (such as, but not limited to, CO2, bicarbonate, carbonate salts, and the like), including, but not limited to, air, CO2-enriched air, flue gas, or the like, or combinations thereof, can be supplied to the culture. When supplying flue gas and/or other sources of inorganic that may contain CO in addition to CO2, it may be necessary to pre-treat such sources such that the CO level introduced into the (photo) bioreactor does not constitute a dangerous and/or lethal dose with respect to the growth, proliferation, and/or survival of the algae.

The recombinant algal can include one or more non-native genes encoding a polypeptide for the production of a product, such as, but limited to, a lipid, a colorant or pigment, an antioxidant, a vitamin, a nucleotide, an nucleic acid, an amino acid, a hormone, a cytokine, a peptide, a protein, a polymer, or combinations thereof. For example, the encoded polypeptide can be an enzyme, metabolic regulator, cofactor, carrier protein, transporter, or combinations thereof.

The methods include culturing a recombinant mutant alga that includes at least one non-native gene encoding a polypeptide that participates in the production of a product, to produce biomass or at least one algal product. Products such as lipids and proteins can be recovered from culture by recovery means known to those of ordinary skill in the art, such as by whole culture extraction, for example, using organic solvents. In some cases, recovery of fatty acid products can be enhanced by homogenization of the cells. For example, lipids such as fatty acids, fatty acid derivatives, and/or triglycerides can be isolated from algae by extraction of the algae with a solvent at elevated temperature and/or pressure, as described in the co-pending, commonly-assigned U.S. patent application publication 2013-0225846A1 entitled "Solvent Extraction of Products from Algae", filed on Feb. 29, 2012, which is incorporated herein by reference in its entirety.

Biomass can be harvested, for example, by centrifugation or filtering. The biomass may be dried and/or frozen. Further products may be isolated from biomass, such as, for example, lipids or one or more proteins.

Also included in the disclosure is an algal biomass comprising biomass of a recombinant algal mutant, such as any disclosed herein, for example, an algal mutant that includes a heterologous gene operably linked to a promoter having at least 80% identity to any of SEQ ID NO:1, SEQ ID NO:4, SEQ ID NO:8, SEQ ID NO:11, SEQ ID NO:13, SEQ ID NO:15, SEQ ID NO:17, SEQ ID NO:19, SEQ ID NO:21, or SEQ ID NO:23; and additionally or alternatively wherein the heterologous gene is followed by a terminator having at least 80% identity to SEQ ID NO:7, SEQ ID NO:9, SEQ ID NO:12, SEQ ID NO:14, SEQ ID NO:16, SEQ ID NO:18, SEQ ID NO:20, SEQ ID NO:22, or SEQ ID NO:24.

Further Embodiments

Alternatively or in addition to any of the forgoing embodiments, the disclosure provides the following embodiments:

Embodiment 1 is an isolated DNA molecule comprising a nucleotide sequence having at least 80%, at least 85%, at least 90%, at least 95%, at least 96%, at least 97%, at least 98%, at least 99%, or 100% identity to at least 100, at least 200, at least 300, at least 400, or at least 500 contiguous nucleotides of SEQ ID NO:1, SEQ ID NO:4, SEQ ID NO:8, SEQ ID NO:11, SEQ ID NO:13, SEQ ID NO:15, SEQ ID NO:17, SEQ ID NO:19, SEQ ID NO:21 or SEQ ID NO:23; for example wherein the nucleotide sequence has at least 80%, at least 85%, at least 90%, at least 95%, at least 96%, at least 97%, at least 98%, or at least 99% identity to a sequence selected from the group consisting of:

- a sequence having at least 100, at least 200, at least 300, at least 400, at least 500, or between 500 and 530 contiguous nucleotides from the 3' end of SEQ ID NO:1;
- a sequence having at least 100, at least 200, at least 300, at least 400, at least 500, at least 600, at least 700, at least 800, at least 900, or between 900 and 1000 contiguous nucleotides from the 3' end of SEQ ID NO:4;
- a sequence having at least 100, at least 200, at least 300, at least 400, at least 500, or between 500 and 572 contiguous nucleotides from the 3' end of SEQ ID NO:8;
- a sequence having at least 100, at least 200, at least 300, at least 400, at least 500, at least 600, at least 700, at least 800, at least 900, at least 1000, or between 1000 and 1044 contiguous nucleotides from the 3' end of SEQ ID NO:11;
- a sequence having at least 100, at least 200, at least 300, at least 400, at least 500, at least 600, at least 700, at least 800, or between 800 and 832 contiguous nucleotides from the 3' end of SEQ ID NO:13;
- a sequence having at least 100, at least 200, at least 300, at least 400, at least 500, or between 600 and 642 contiguous nucleotides from the 3' end of SEQ ID NO:15;
- a sequence having at least 100, at least 200, at least 300, at least 400, at least 500, or between 500 and 588 contiguous nucleotides from the 3' end of SEQ ID NO:17;
- a sequence having at least 100, at least 200, at least 300, at least 400, at least 500, at least 600, at least 700, or between 700 and 707 contiguous nucleotides from the 3' end of SEQ ID NO:19;
- a sequence having at least 100, at least 200, at least 300, at least 400, at least 500, at least 600, at least 700, at least 800, or between 800 and 874 contiguous nucleotides from the 3' end of SEQ ID NO:21; or
- a sequence having at least 100, at least 200, at least 300, at least 400, at least 500, at least 600, at least 700, at least 800, or between 800 and 874 contiguous nucleotides from the 3' end of SEQ ID NO:23.

Embodiment 2 is an isolated or recombinant nucleic acid molecule according to Embodiment 1, wherein at least one of the following are satisfied:

a) the nucleic acid molecule comprises a promoter operable in a eukaryotic cell, preferably an algal cell or chlorophyte cell;
b) the nucleotide sequence having at least 80% identity to at least 100 contiguous nucleotides of SEQ ID NO:1, SEQ ID NO:4, SEQ ID NO:8, SEQ ID NO:11, SEQ ID NO:13, SEQ ID NO:15, SEQ ID NO:17, SEQ ID NO:19, SEQ ID NO:21 or SEQ ID NO:23 is operably linked to a heterologous sequence;
c) the nucleic acid molecule is an expression cassette; or
d) the nucleic acid molecule is a vector.

Embodiment 3

A promoter comprising a nucleic acid sequence having at least 80%, at least 85%, at least 90%, at least 95%, at least 96%, at least 97%, at least 98%, or at least 99% identity to a sequence selected from the group consisting of a sequence having at least 100, at least 200, at least 300, at least 400, at least 500, or between 500 and 530 contiguous nucleotides from the 3' end of SEQ ID NO:1; a nucleotide sequence having at least 80%, at least 85%, at least 90%, at least 95%, at least 96%, at least 97%, at least 98%, or at least 99% identity to at least 100, at least 200, at least 300, at least 400, at least 500, at least 600, at least 700, at least 800, at least 900, or between 900 and 1000 contiguous nucleotides from the 3' end of SEQ ID NO:4; a nucleotide sequence having at least 80%, at least 85%, at least 90%, at least 95%, at least 96%, at least 97%, at least 98%, or at least 99% identity to at least 100, at least 200, at least 300, at least 400, at least 500, or between 500 and 572 contiguous nucleotides from the 3' end of SEQ ID NO:8; a nucleotide sequence having at least 80%, at least 85%, at least 90%, at least 95%, at least 96%, at least 97%, at least 98%, or at least 99% identity to at least 100, at least 200, at least 300, at least 400, at least 500, at least 600, at least 700, at least 800, at least 900, at least 1000, or between 1000 and 1044 contiguous nucleotides from the 3' end of SEQ ID NO:11; a nucleotide sequence having at least 80%, at least 85%, at least 90%, at least 95%, at least 96%, at least 97%, at least 98%, or at least 99% identity to at least 100, at least 200, at least 300, at least 400, at least 500, at least 600, at least 700, at least 800, or between 800 and 832 contiguous nucleotides from the 3' end of SEQ ID NO:13; a nucleotide sequence having at least 80%, at least 85%, at least 90%, at least 95%, at least 96%, at least 97%, at least 98%, or at least 99% identity to at least 100, at least 200, at least 300, at least 400, at least 500, at least 600, or between 600 and 642 contiguous nucleotides from the 3' end of SEQ ID NO:15; a nucleotide sequence having at least 80%, at least 85%, at least 90%, at least 95%, at least 96%, at least 97%, at least 98%, or at least 99% identity to at least 100, at least 200, at least 300, at least 400, at least 500, or between 500 and 588 contiguous nucleotides from the 3' end of SEQ ID NO:17; a nucleotide sequence having at least 80%, at least 85%, at least 90%, at least 95%, at least 96%, at least 97%, at least 98%, or at least 99% identity to at least 100, at least 200, at least 300, at least 400, at least 500, at least 600, at least 700, or between 700 and 707 contiguous nucleotides from the 3' end of SEQ ID NO:19; a nucleotide sequence having at least 80%, at least 85%, at least 90%, at least 95%, at least 96%, at least 97%, at least 98%, or at least 99% identity to at least 100, at least 200, at least 300, at least 400, at least 500, at least 600, at least 700, at least 800, or between 800 and 874 contiguous nucleotides from the 3' end of SEQ ID NO:21; or a nucleotide sequence having at least 80%, at least 85%, at least 90%, at least 95%, at least 96%, at least 97%, at least 98%, or at least 99% identity to at least 100, at least 200, at least 300, at least 400, at least 500, at least 600, at least 700, at least 800, or between 800 and 874 contiguous nucleotides from the 3' end of SEQ ID NO:23.

Embodiment 4

A nucleic acid molecule comprising a promoter according to Embodiment 3 operably linked to a heterologous nucleotide sequence, wherein any of the following are satisfied:

a) the heterologous nucleotide sequence encodes a polypeptide, wherein the polypeptide is optionally any of: a protein associated with lipid biosynthesis, a polypeptide having lipolytic activity, a polypeptide that participates in photosynthesis, a protein associated with carbon fixation, a transporter protein, a dehydrogenase, a transcription factor, a transcriptional activator, a metabolic enzyme, a protein involved in protein synthesis, a protein involved in cell signaling, a kinase, or a G protein;
b) the heterologous nucleotide sequence encodes a functional RNA, wherein the functional RNA is optionally any of: an antisense RNA, a small hairpin RNA, a microRNA, an antisense RNA, a siRNA, a piRNA, a gRNA, or a ribozyme;
c) the heterologous nucleotide sequence is further operably linked to a terminator, optionally wherein the terminator comprises a nucleotide sequence having at least 80% at least 85%, at least 90%, at least 95%, at least 96%, at least 97%, at least 98%, at least 99%, or about 100% identity to at least 100 contiguous nucleotides of a sequence selected from the group consisting of SEQ ID NO:7, SEQ ID NO:9, SEQ ID NO:12, SEQ ID NO:14, SEQ ID NO:16, SEQ ID NO:18, SEQ ID NO:20, SEQ ID NO:22, and SEQ ID NO:24;
d) the heterologous nucleotide sequence encodes a polypeptide and includes at least one intron that is heterologous with respect to the polypeptide-encoding sequence, optionally wherein at least one intron comprises a nucleotide sequence having at least 80% at least 85%, at least 90%, at least 95%, at least 96%, at least 97%, at least 98%, at least 99%, or about 100% identity to at least 100 contiguous nucleotides of a sequence selected from the group consisting of SEQ ID NO:25, SEQ ID NO:26, SEQ ID NO:27, SEQ ID NO:28, SEQ ID NO:29, SEQ ID NO:35, SEQ ID NO:36, SEQ ID NO:37, SEQ ID NO:38, SEQ ID NO:39, SEQ ID NO:40, SEQ ID NO:41, SEQ ID NO:42, and SEQ ID NO:43.

Embodiment 5

An isolated DNA molecule comprising a nucleotide sequence having at least 80% at least 85%, at least 90%, at least 95%, at least 96%, at least 97%, at least 98%, at least 99%, or about 100% identity to at least 100 contiguous nucleotides of a nucleotide sequence selected from the group consisting of SEQ ID NO:7, SEQ ID NO:9, SEQ ID NO:12, SEQ ID NO:14, SEQ ID NO:16, SEQ ID NO:18, SEQ ID NO:20, SEQ ID NO:22, and SEQ ID NO:24, optionally wherein the nucleotide sequence is operably linked to a heterologous sequence.

Embodiment 6

An isolated or recombinant nucleic acid molecule comprising a gene encoding a polypeptide, wherein the gene comprises at least one, at least two, at least three, at least four, at least five, at least six, at least seven, at least eight, or at least nine introns having at least 80%, at least 85%, at least 90%, at least 95%, at least 96%, at least 97%, at least 98%, at least 99%, or about 100% identity to SEQ ID NO:25, SEQ ID NO:26, SEQ ID NO:27, SEQ ID NO:28, SEQ ID NO:29, SEQ ID NO:35, SEQ ID NO:36, SEQ ID NO:37, SEQ ID NO:38, SEQ ID NO:39, SEQ ID NO:40, SEQ ID NO:41, SEQ ID NO:42, or SEQ ID NO:43; optionally wherein:
the gene is operably linked to a promoter, optionally a promoter according to Embodiment 3; and/or the gene is operably linked to a terminator, optionally a terminator comprising a nucleotide sequence having at least 80% at least 85%, at least 90%, at least 95%, at least 96%, at least 97%, at least 98%, at least 99%, or about 100% identity to at least 100 contiguous nucleotides of a nucleotide sequence selected from the group consisting of SEQ ID NO:7, SEQ ID NO:9, SEQ ID NO:12, SEQ ID NO:14, SEQ ID NO:16, SEQ ID NO:18, SEQ ID NO:20, SEQ ID NO:22, and SEQ ID NO:24;
optionally wherein the at least one, at least two at least three, at least four, at least five, at least six, at least seven, at least eight, or at least nine introns are derived from same species as the promoter, optionally wherein the at least one, at least two at least three, at least four, at least five, at least six, at least seven, at least eight, or at least nine introns are derived from the same species as the promoter and terminator;
further optionally wherein the at least one, at least two, at least three, at least four, at least five, at least six, at least seven, at least eight, or at least nine introns are derived from the same gene as the promoter, optionally wherein the at least one, at least two at least three, at least four, at least five, at least six, at least seven, at least eight, or at least nine introns are derived from the same gene as the promoter and terminator.

Embodiment 7

An expression cassette comprising: a gene encoding a polypeptide operably linked to a heterologous promoter according to Embodiment 3;
optionally wherein the gene includes at least two, at least three, at least four, at least five, at least six, at least seven, at least eight, or at least nine introns are derived from the same species as the promoter, optionally wherein the at least two, at least three, at least four, at least five, at least six, at least seven, at least eight, or at least nine introns are derived from the same gene;
optionally further including:
a terminator comprising a nucleotide sequence having at least 80% at least 85%, at least 90%, at least 95%, at least 96%, at least 97%, at least 98%, at least 99%, or about 100% identity to at least 100 contiguous nucleotides of a nucleotide sequence selected from the group consisting of SEQ ID NO:7, SEQ ID NO:9, SEQ ID NO:12, SEQ ID NO:14, SEQ ID NO:16, SEQ ID NO:18, SEQ ID NO:20, SEQ ID NO:22, and SEQ ID NO:24 operably linked to the gene.

Embodiment 8

An expression cassette according to Embodiment 7, wherein: the gene encodes a selectable marker protein, a detectable marker protein, a protein associated with lipid biosynthesis, an acetyl-CoA carboxylase, a malonyl type 1 fatty acid synthase, a Type 2 fatty acid synthase subunit, a beta ketoacyl-ACP synthase, a malonyl-CoA-malonyl-ACP acyltransferase, an acyl-ACP thioesterase, an acyl-CoA thioesterase, a 4-hydroxybenzoyl thioesterase, an alcohol forming acyl reductase, a wax synthase, an aldehyde decarbonylase, a fatty acid decarboxylase, a lipase, a glyceraldehyde 3 phosphate dehydrogenase, an acyl-CoA synthetase, a phospholipid diacylglycerol acyltransferase, a glycerol 3 phosphate acyltransferase, a lysophosphatidic acid acyltransferase, a phosphatidic acid phosphatase, a diacyl glycerol acyltransferase, a polypeptide having lipolytic activity, a polypeptide that participates in photosynthesis, a chlorophyll binding light harvesting polypeptide, a photosynthetic reaction center polypeptide, an oxygen-evolving complex polypeptide, a cytochrome, a ferredoxin, a protein associated with carbon fixation, a ribulose bisphoshate carboxylase subunit, a carbonic anhydrase, a transporter protein, an ABC transporter, a FatB transporter, a dehydrogenase, an aldehyde dehydrogenase, a 2-hydroxyacid dehydrogenase, an isocitrate dehydrogenase, 6 phosphogluconate dehydrogenase, glucose 6 phosphate dehydrogenase; a transcription factor, a transcriptional activator, a protein involved in cell signaling, a kinase, or a G protein.

Embodiment 9

A vector comprising an expression cassette according to any of Embodiments 4, 7, or 8, wherein the expression vector further comprises one or more of: an origin of replication; one or more sequences for promoting integration of the expression cassette into the host genome, a selectable marker gene; and a reporter gene; optionally wherein the selectable marker gene is selected from the group consisting of a gene conferring resistance to an antibiotic, a gene conferring resistance to an herbicide, a gene encoding acetyl CoA carboxylase (ACCase), a gene encoding acetohydroxy acid synthase (ahas), a gene encoding acetolactate synthase, a gene encoding aminoglycoside phosphotransferase, a gene encoding anthranilate synthase, a gene encoding bromoxynil nitrilase, a gene encoding cytochrome P450-NADH-cytochrome P450 oxidoreductase, a gene encoding dalapon dehalogenase, a gene encoding dihydropteroate synthase, a gene encoding a class I 5-enolpyruvylshikimate-3-phosphate synthase (EPSPS), a gene encoding a class II EPSPS (aroA), a gene encoding a non-class I/II EPSPS, a gene encoding glutathione reductase, a gene encoding glyphosate acetyltransferase, a gene encoding glyphosate oxidoreductase, a gene encoding hydroxyphenylpyruvate dehydrogenase, a gene encoding hydroxy-phenylpyruvate dioxygenase, a gene encoding isoprenyl pyrophosphate isomerase, a gene encoding lycopene cyclase, a gene encoding phosphinothricin acetyl transferase, a gene encoding phytoene desaturase, a gene encoding prenyl transferase, a gene encoding protoporphyrin oxidase, a gene encoding superoxide dismutase, arg7, his3, hisD, hisG, manA, nitl, trpB, uidA, xylA, a dihydrofolate reductase gene, a mannose-6-phosphate isomerase gene, a nitrate reductase gene, an ornithine decarboxylase gene, a thymidine kinase gene, a 2-deoxyglucose resistance gene; an R-locus gene, a tyrosinase gene; and optionally wherein a detectable marker gene is lacZ, an alkaline phosphatase gene, an α-amylase gene, a horseradish peroxidase gene, an α-galactosidase gene, a luciferin and/or luciferase gene, a beta-glucuronidase gene (GUS), or a gene encoding a fluorescent protein.

Embodiment 10

A method for transforming a eukaryotic cell comprising: 1) introducing a vector or expression cassette according to any of Embodiments 7-9 into the eukaryotic cell; and 2) selecting for a transformed eukaryotic cell, preferably wherein the eukaryotic host cell is a fungal, algal, heterokont, chlorophyte, or plant host cell; optionally wherein the eukaryotic host cell is an algal cell such as a species of Bacillariophyceae (diatoms), Bolidomonas, Chlorophyceae (green algae), Chrysophyceae (golden algae), Cyanophyceae (cyanobacteria), Eustigmatophyceae (pico-plankton), Glaucocystophytes, Pelagophyceae, Bolidophyceae, Prasinophyceae (pico-plankton), Raphidophyceae, Rhodophyceae (red algae), Synurophyceae and Xanthophyceae (yellow-green algae), *Achnanthes, Amphiprora, Amphora, Ankistrodesmus, Asteromonas, Boekelovia, Bolidomonas, Borodinella, Botrydium, Botryococcus, Bracteococcus, Chaetoceros, Carteria, Chlamydomonas, Chlorococcum, Chlorogonium, Chlorella, Chroomonas, Chrysosphaera, Cricosphaera, Crypthecodinium, Cryptomonas, Cyclotella, Dunaliella, Ellipsoidon, Emiliania, Eremosphaera, Ernodesmius, Euglena, Eustigmatos, Franceia, Fragilaria, Gloeothamnion, Haematococcus, Halocafeteria, Heterosigma, Hymenomonas, Isochrysis, Lepocinclis, Micractinium, Monoraphidium, Nannochloris, Nannochloropsis, Navicula, Neochloris, Nephrochloris, Nephroselmis, Nitzschia, Ochromonas, Oedogonium, Oocystis, Ostreococcus, Pavlova, Parachlorella, Pascheria, Pelagomonas, Phaeodactylum, Phagus, Picochlorum, Platymonas, Pleurochrysis, Pleurococcus, Prototheca, Pseudochlorella, Pseudoneochloris, Pseudostaurastrum, Pyramimonas, Pyrobotrys, Scenedesmus, Skeletonema, Spyrogyra, Stichococcus, Tetraselmis, Thalassiosira, Tribonema, Vaucheria, Viridiella, Vischeria,* or *Volvox*; optionally wherein the eukaryotic host cell is an algal cell of a Chlorophyte species; further optionally wherein the eukaryotic host cell is an algal cell of the Trebouxiophyceae class, further optionally wherein the eukaryotic host cell is an algal cell of a genus selected from the group consisting of *Auxenochlorella, Chlorella, Heveochlorella, Marinichlorella, Pseudochlorella,* and *Tetrachlorella.*

Embodiment 11

A method according to Embodiment 10, wherein the vector is introduced by a biolistic procedure, optionally wherein at least about 300 psi of pressure is used to impel biolistic microcarriers coated with vector DNA into the eukaryotic cell.

Embodiment 12

A method according to Embodiment 10, wherein the vector is introduced by an electroporation procedure, optionally wherein the voltage is at least 0.5 kV, the capacitance is at least 10 µF, and the resistance is at least 100 Ohms, and further optionally wherein the voltage is between 1.0-1.2 kV (5000-6000V/cm), the resistance is between 200-300 ohms, and the capacitance is between 25-50 uF.

Embodiment 13

A method for co-transforming a eukaryotic cell comprising: 1) introducing an expression cassette according to Embodiment 7 or Embodiment 8 and a nucleic acid sequence encoding a selectable marker into the eukaryotic cell; and 2) selecting for the presence of the selectable marker in a transformed eukaryotic cell to provide a eukaryotic cell transformed with the expression cassette, optionally wherein the eukaryotic cell is an algal cell, optionally wherein the selectable marker gene is operably linked to a promoter according to Embodiment 3, optionally wherein the selectable marker gene is selected from the group consisting of a gene conferring resistance to an antibiotic, a gene conferring resistance to an herbicide, a gene encoding acetyl CoA carboxylase (ACCase), a gene encoding acetohydroxy acid synthase (ahas), a gene encoding acetolactate synthase, a gene encoding aminoglycoside phosphotransferase, a gene encoding anthranilate synthase, a gene encoding bromoxynil nitrilase, a gene encoding cytochrome P450-

NADH-cytochrome P450 oxidoreductase, a gene encoding dalapon dehalogenase, a gene encoding dihydropteroate synthase, a gene encoding a class I 5-enolpyruvylshikimate-3-phosphate synthase (EPSPS), a gene encoding a class II EPSPS (aroA), a gene encoding a non-class I/II EPSPS, a gene encoding glutathione reductase, a gene encoding glyphosate acetyltransferase, a gene encoding glyphosate oxidoreductase, a gene encoding hydroxyphenylpyruvate dehydrogenase, a gene encoding hydroxy-phenylpyruvate dioxygenase, a gene encoding isoprenyl pyrophosphate isomerase, a gene encoding lycopene cyclase, a gene encoding phosphinothricin acetyl transferase, a gene encoding phytoene desaturase, a gene encoding prenyl transferase, a gene encoding protoporphyrin oxidase, a gene encoding superoxide dismutase, arg7, his3, hisD, hisG, manA, nitl, trpB, uidA, xylA, a dihydrofolate reductase gene, a mannose-6-phosphate isomerase gene, a nitrate reductase gene, an ornithine decarboxylase gene, a thymidine kinase gene, a 2-deoxyglucose resistance gene; and an R-locus gene.

Embodiment 14

A method according to Embodiment 13, wherein the selectable marker gene is a gene conferring resistance to an antibiotic, optionally wherein the antibiotic is blasticidin, bleomycin (Zeocin™), or nourseothricin.

Embodiment 15

A eukaryotic host cell comprising an isolated or recombinant nucleic acid molecule, expression cassette, or vector of any of Embodiments 1-9, wherein the eukaryotic host cell is optionally a microalgal cell, optionally a species of Bacillariophyceae, Bolidomonas, Chlorophyceae, Chrysophyceae, Eustigmatophyceae, Glaucocystophytes, Pelagophyceae, Bolidophyceae, Prasinophyceae, Raphidophyceae, Rhodophyceae (red algae), Synurophyceae or Xanthophyceae (yellow-green algae), or of a genus selected from the group consisting of: *Achnanthes, Amphiprora, Amphora, Ankistrodesmus, Asteromonas, Boekelovia, Bolidomonas, Borodinella, Botrydium, Botryococcus, Bracteococcus, Chaetoceros, Carteria, Chlamydomonas, Chlorococcum, Chlorogonium, Chlorella, Chroomonas, Chrysosphaera, Cricosphaera, Crypthecodinium, Cryptomonas, Cyclotella, Dunaliella, Ellipsoidon, Emiliania, Eremosphaera, Ernodesmius, Euglena, Eustigmatos, Franceia, Fragilaria, Gloeothamnion, Haematococcus, Halocafeteria, Heterosigma, Hymenomonas, Isochrysis, Lepocinclis, Micractinium, Monoraphidium, Nannochloris, Nannochloropsis, Navicula, Neochloris, Nephrochloris, Nephroselmis, Nitzschia, Ochromonas, Oedogonium, Oocystis, Ostreococcus, Pavlova, Parachlorella, Pascheria, Pelagomonas, Phaeodactylum, Phagus, Picochlorum, Platymonas, Pleurochrysis, Pleurococcus, Prototheca, Pseudochlorella, Pseudoneochloris, Pseudostaurastrum, Pyramimonas, Pyrobotrys, Scenedesmus, Schizochlamydella, Skeletonema, Spyrogyra, Stichococcus, Tetrachlorella, Tetraselmis, Thalassiosira, Tribonema, Vaucheria, Viridiella, Vischeria,* and *Volvox*; optionally an algal cell of the Trebouxiophyceae class, further optionally wherein the eukaryotic host cell is an algal cell of a genus selected from the group consisting of *Auxenochlorella, Chlorella, Heveochlorella, Marinichlorella, Pseudochlorella,* and *Tetrachlorella*.

EXAMPLES

Strains and Media

*Parachlorella* is a genus of green alga in the Chlorophyte phylum. Along with genera such as but not limited to *Botryococcus, Eremosphaera, Franceia, Micractinium, Nannochloris, Oocystis, Picochlorum, Prototheca, Stichococcus,* and *Viridiella, Parachlorella* and related genera *Auxenochlorella, Chlorella, Heveochlorella, Marinichlorella, Pseudochlorella,* and *Tetrachlorella*, are members of the Trebouxiophyceae class of the Chlorophyta phylum. A strain of *Parachlorella* was isolated from the environment and given the designation WT-1185.

Media used for the growth of *Parachlorella* included the following:

PM074 is a nitrogen replete ("nitrate-only") medium that is 10×F/2 made by adding 1.3 ml PROLINE® F/2 Algae Feed Part A (Aquatic Eco-Systems) and 1.3 ml PROLINE® F/2 Algae Feed Part B (Aquatic Eco-Systems) to a final volume of 1 liter of a solution of Instant Ocean salts (35 g/L) (Aquatic Eco Systems, Apopka, Fla.). Proline A and Proline B together include 8.8 mM $NaNO_3$, 0.361 mM $NaH_2PO_4 \cdot H_2O$, 10×F/2 Trace metals, and 10×F/2 Vitamins (Guillard (1975) Culture of phytoplankton for feeding marine invertebrates. in "Culture of Marine Invertebrate Animals." (eds: Smith W. L. and Chanley M. H.) Plenum Press, New York, USA. pp 26-60).

PM126 is a nitrogen replete ("nitrate-only") medium that is 10×F/2 made by adding 1.3 ml PROLINE® F/2 Algae Feed Part A (Aquatic Eco-Systems) and 1.3 ml PROLINE® F/2 Algae Feed Part B (Aquatic Eco-Systems) to a final volume of 1 liter of a solution of Instant Ocean salts (7 g/L) (Aquatic Eco Systems, Apopka, Fla.). Proline A and Proline B together include 8.8 mM $NaNO_3$, 0.361 mM $NaH_2PO_4 \cdot H_2O$, 10×F/2 Trace metals, and 10×F/2 Vitamins (Guillard (1975) Culture of phytoplankton for feeding marine invertebrates. in "Culture of Marine Invertebrate Animals." (eds: Smith W. L. and Chanley M. H.) Plenum Press, New York, USA. pp 26-60).

Example 1. Identification of *Parachlorella* Regulatory Sequences

Multiple sequences were isolated and tested for their ability to function as promoters or terminators in gene expression cassettes. Upstream and downstream nucleic acid sequences flanking selected genes based on a genome assembly for the wild type *Parachlorella* strain WT-1185 were tested for promoter or terminator function respectively. Endogenous genes from WT-1185 were selected to cover a wide range of gene structures with respect to open reading frame size, intron number, and expression strength based on genome sequencing and transcriptomics data. Genes were only considered if the upstream and downstream regions of the genes were present on the same strand of DNA and if deduced 5' and 3' untranslated regions were available from RNA-seq cDNA assemblies. The genes that were selected are listed in Table 1, along with the SEQ ID numbers for the respective promoter and terminator.

Example 2. Generation of Expression Cassette

One construct which resulted in successful generation of a transgenic strain in WT-1185 was pSGE6450. In this construct, the RPS4_P promoter (SEQ ID NO:1) was used to drive the expression of the bleomycin resistance gene, BleR (SEQ ID NO:2), followed by a terminator sourced from *Nannochloropsis* wild type strain WT-3730 (3730 T4; SEQ ID NO:3). In addition, a second green fluorescent protein (GFP) reporter cassette comprised the TurboGFP (Evrogen, Moscow, Russia) coding sequence codon optimized for *Parachlorella* (SEQ ID NO:5) flanked by the PsbR_P promoter (SEQ ID NO:4) at the 5' end of the gene and the *Nannochloropsis gaditana* wild type (WT-3730) strain T5 terminator also sourced from WT-3730 (SEQ ID NO:6) at the 3' end of the gene; this expression construct was cloned into a minimal *E. coli* pUC backbone vector. The GFP cassette was oriented on the DNA strand opposite to the strand encoding the BleR (zeocin) selection cassette. A schematic of plasmid pSG6450 is shown in FIG. 1. For transformation into *Parachlorella* cells by particle bombardment, pSG6450 was linearized with NdeI.

Example 3. Transformation Via Particle Bombardment

Transformation of *Parachlorella* WT-1185 was accomplished using the Helios® Gene Gun System (Bio-Rad, Hercules, Calif., USA). The protocol was developed using the manufacturer's instruction manual (available online at bio-rad.com/en-us/product/helios-gene-gun-system). As detailed below, DNA for transformation was precipitated onto gold particles, the gold particles were adhered to the inside of lengths of tubing, and a burst of helium gas fired through the tubing by the Gene Gun projected the DNA-coated gold particles into WT-1185 cells adhered on solid non-selective media. The following day, cells were moved onto selective media for growth of transformed colonies.

Preparation of DNA-coated gold bullets was accomplished by either one of two methods: a 40-bullet method and a 10-bullet method. The 40-bullet method, which required approximately 40 μg of DNA, used the BioRad Tubing Prep Station and was performed according to the manufacturer's protocol in the Helios® Gene Gun System manual and as described in U.S. Pat. No. 8,883,993, incorporated herein by reference. The 10-bullet prep method was performed as described in co-pending and commonly owned patent U.S. patent application Ser. No. 15/343,064, filed Nov. 3, 2016. For the 10-bullet method, DNA (2-10 μg) was precipitated onto gold particles and resuspended in 100% ethanol/10 μg/ml PVP solution as detailed in the Helios® manual with the exception that the volumes were calculated to make ten bullets instead of forty bullets. While the DNA/gold suspension was being prepared, one 7" length of Tefzel™ (ethylene tetrafluoroethylene) tubing for each sample was pre-dried by insertion into the flexible tubing attached to the manifold drier and left for at least fifteen minutes with ~0.4 LPM nitrogen flowing through to eliminate environmental humidity accumulation from the inside of the Tefzel™ tubing.

After preparing the DNA/gold suspension and pre-drying the Tefzel™ tubing, the flexible tubing was disconnected from the manifold drier at the Leur lock and attached to a 10 mL syringe. The DNA/gold suspension was mixed well and drawn into the Tefzel™ tubing by application of suction by the syringe. While still connected to the syringe, the Tefzel™ tubing was laid on a flat surface for five minutes while the gold settles out of solution and adheres to the inside of the tubing. Since the percentage of the gold that adheres to the tubing is influenced by the settling time, the settling time was consistent for every sample.

After five minutes of settling time, pressure was applied with the syringe to gently push the ethanol out of the tubing. The tubing was immediately turned over to allow the remaining gold slurry to smear to the side of the Tefzel™ tubing opposite where it originally settled. After 2-5 minutes of air drying time, the Tefzel™ tubing was detached from the syringe and moved back onto the manifold drier with 0.1-0.2 LPM nitrogen flowing. Monitoring of the drying process entailed increasing or decreasing the nitrogen flow to allow the gold to dry without being blown out of the Tefzel™ tubing as well as occasionally turning over the Tefzel™ tubing to more evenly coat the interior of the tubing. When the gold was completely dried as evidenced from a visible color change from dark to light yellow, the Tefzel™ tubing was removed from the flexible tubing and cut into half-inch pieces for use in the Helios Gene Gun™

To prepare cells for transformation, a 100 mL seed culture inoculated to 1×106 cells/mL six days before transformation was used to inoculate a 1 L culture to 1×106 cells/mL two days before transformation. Cell counts were determined using a BD Accuri™ C6 Flow Cytometer. Cultures were grown in PM074 or PM126 media in a Conviron™ Incubator at 25 C 1% CO2 shaking at 130 rpm in a 16:8 light:dark cycle.

On the day of transformation, cell cultures were pelleted by centrifugation at 4500×g for twenty minutes. Cells were resuspended in 50 mL osmoticum (250 mM mannitol/250 mM sorbitol 0.1 um filter-sterilized) and incubated for 1-2 hours at room temperature.

After osmotic pre-treatment cells were concentrated to 4×109 cells/mL in osmoticum, and 50 uL of cell suspension was painted in each of five 4 cm-diameter circles on a 13 cm-diameter shooting plate containing 2% agar PM074 solid medium. When the cells were completely dried, the Helios® Gene Gun was used to fire two bullets per cell circle at 600 psi from a distance of 3-6 cm from the plate. In total for each individual DNA, 10 replicate bullets were fired at 1×109 cells divided among 5 cell circles. Cells were left on the shooting plates overnight in ambient benchtop conditions.

The day after transformation, cells from replicate cell circles were pooled together by washing the shooting plates with liquid PM074 or PM126 media. Recovered cells were plated onto selective media (PM074 containing zeocin 250 mg/L or PM126 containing 200 mg/L) at an intended density of $1×10^9$ cells per 22×22 cm agar plate.

Example 4. WT-1185 Promoter-GFP Reporter Assessment

Figure 2:
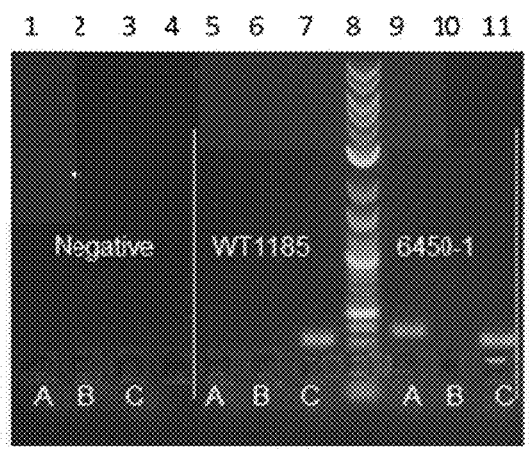
FIG. 2 shows a picture of a gel of colony PCR of strain 6450-1 confirming the presence of plasmid pSGE6450. Sequence specific primers were used to amplify BleR gene (lanes labeled A) GFP (lanes labeled B), and RibD sequence region endogenous to WT-1185 (lanes labeled C). Lane 8 was loaded with the Log 2 DNA ladder from New England Biolabs. Samples tested by PCR are indicated by the group labels Negative (no template control PCR), TWE1185 (PCR template from WT-1185) and 6450-1 (PCR template from strain 6450-1).

Transformation of the NdeI linearized pSG6450 construct by particle bombardment into WT-1185 resulted in a single transgenic colony generated (referred to as strain 6450-1) which was resistant to Zeocin (250 μg per ml) on agar plates. The colony was resuspended in 200 μL PM074 liquid media and aliquots of the cell suspension were spotted for secondary selection onto PM074/zeo250 media and grown in a Conviron incubator set at 25° C. with 1% $CO_2$ on a 16:8 light:dark diel cycle. After secondary selection in zeocin medium, cells were resuspended in 200 μL PM074 and 10,000 events from the cell suspensions were read on a BD Accuri™ C6 Flow Cytometer. (To ensure consistency in comparison similar cell populations, events were gated on cell size and chlorophyll fluorescence (FL3) before overlaying FL1 profiles for analysis of GFP overexpression.) Although the 6450-1 transformant was confirmed to harbor the BleR gene by colony PCR (FIG. 2, PCR product visible in lane A), it was not found to express GFP by flow cytometry analyses or PCR. Strain 6450-1 genomic DNA was sequenced and bioinformatics analysis revealed that the pSG6450 construct was present in multiple partial copies with complex rearrangements.

Example 5. Construction and Testing of Additional Expression Cassettes

Figure 3A:
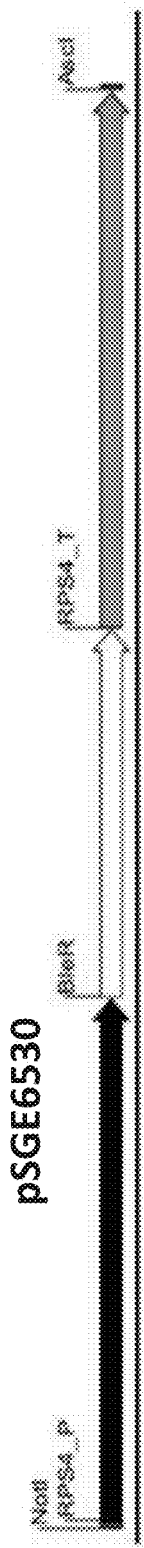
FIGS. 3A-3B provides diagrams of A) plasmid pSGE6530 and B) plasmid pSGE6531. Positions of AscI and NotI restriction enzyme sites are indicated.
Figure 3B:
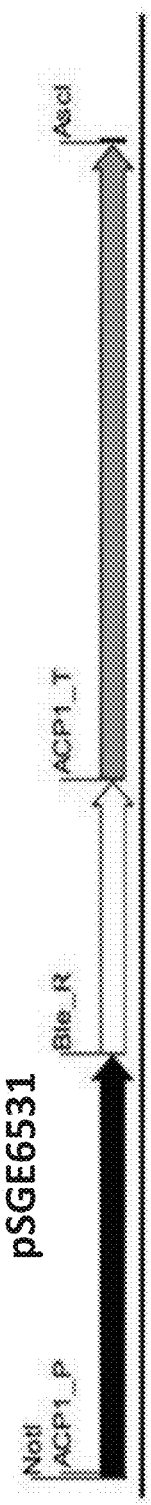

To test other nucleic acid sequences for potential promoter or terminator function, potential regulatory elements from the RPS4 gene and the ACP gene (Table 1) were cloned and tested. Plasmid pSG6530 was constructed to drive the expression of BleR (zeocin resistance marker) by flanking this coding region with paired promoter and terminator sequences from the RPS4 gene, SEQ ID NO:1 and SEQ ID NO:7, respectively (FIG. 3A). Plasmid pSG6531 was constructed to drive the expression of BleR (zeocin resistance marker) by flanking this coding region with paired promoter and terminator sequences from the ACP gene, SEQ ID NO:8 and SEQ ID NO:9, respectively (FIG. 3B). These plasmids were transformed into WT-1185 by particle bombardment as described in Example 3. The pSG6530 and pSG6531 constructs (unlike the pSG6450 construct of Examples 2-4) each had a transgene that was not a *Parachlorella* gene or derived from a *Parachlorella* gene) operably linked to a *Parachlorella* promoter and a *Parachlorella* terminator. In both the pSG6530 and pSG6531 constructs, the transgene was operably linked to a promoter and terminator from the same *Parachlorella* gene: the RPS4 gene promoter (SEQ ID NO:1) and terminator (SEQ ID NO:7) flanked the BleR gene in pSG6530 and the ACP1 promoter (SEQ ID NO:8) and terminator (SEQ ID NO:9) flanked the BleR gene in pSG6531.

Colonies generated by Helios transformation as described in Example 3 were visible eleven days after transformation and were resuspended in 200 μL PM074 liquid media in 96-well sterile plates. Aliquots of cell suspensions were spotted for secondary selection onto PM074/zeo250 media and grown in a Conviron incubator set at 25° C. with 1% CO2 on a 16:8 light:dark diel cycle. Biomass from lines surviving secondary selection was resuspended in 200 μL PM074. 10,000 events from the cell suspensions were read on a BD Accuri™ C6 Flow Cytometer. To ensure consistency in comparison similar cell populations, events were gated on cell size and chlorophyll fluorescence (FL3) before overlaying FL1 profiles for analysis of GFP overexpression.

Results for particle bombardment transformation of pSG6530 and pSG6531 are summarized in Table 2. In general, a marked increase in the number of transformants obtained was observed for these constructs relative to the pSG6450 construct described in Examples 2 and 4. Both the AscI-NotI restriction digested fragments or the constructs linearized in the vector backbone were (separately) transformed into WT-1185 cells, and transformants were obtained from transformations with both fragments and linearized vectors. Colony PCR was performed on a subset of these transgenic lines to detect the transgenic construct from the 5' end of the promoter to the 3' end of the terminator for both plasmids to determine whether the entire transformed construct was present. Between ~40% and 100% of transformants analyzed harbored the entire expression construct, tested as described in Example 4, indicating that a significant improvement in transformation rates and stability of the construct in transformed lines (Table 3).

TABLE 2

Number of transformants generated using pSGE06530 and pSGE06531 constructs.

| transformed | Zeocin resistant colonies | Zeocin resistant colonies |
| --- | --- | --- |
| DNA-free gold particles | 0 | 0 |
| No bombardment | 0 | 0 |
| pSG6530 fragment | 46 | 59 |
| pSG6531 fragment | 9 | 13 |
| pSG6530 linear | 13 | 27 |
| pSG6531 linear | 31 | 56 |

TABLE 3

Results of PCR for Integration of Entire Transformed Fragment or Linear Construct.

| Construct | Fraction with Entire AscI-NotI Fragment | Fraction with Entire Linearized Construct |
| --- | --- | --- |
| pSG6530 | 3/8 (38%) | 8/8 (100%) |
| pSG6531 | 4/8 (50%) | 2/5 (40%) |

Example 6. Intronylation of Heterologous Genes for Expression in *Parachlorella*

To investigate the effects of introns on expression of the bleomycin resistance gene (BleR) in *Parachlorella*, sequences of introns derived the *Parachlorella* Ribosomal Protein S4 (RPS4) gene were determined.

TABLE 4

Introns of the *Parachlorella* RPS4 Gene.

| Intron number | Size of Intron (bp) | SEQ ID NO |
| --- | --- | --- |
| 1 | 156 | 25 |
| 2 | 292 | 26 |
| 3 | 1322 | 27 |
| 4 | 326 | 28 |
| 5 | 196 | 29 |

Figure 4:
FIG. 4 is a diagram of plasmid pSGE6543 that includes an intronylated BleR gene (SEQ ID NO:2) that includes five introns (SEQ ID NOs:25-29) of the RPS4 gene with as summary of construct components in the table below, including the RPS4 promoter (SEQ ID NO:1) and RPS4 terminator (SEQ ID NO:7). Positions of AscI and NotI restriction enzyme sites are indicated.

A new construct, pSGE6543, was engineered in which the BleR gene was "intronylated" by insertion of introns from the RPS4 gene (FIG. 4) in the same order in which they occur in the native *Parachlorella* RPS4 gene. The construct was similar to that of pSG6530 (FIG. 3A), except that introns 1-5 of the *Parachlorella* RPS4 gene (Table 4) were introduced into the codon-optimized sequence of the BleR gene (SEQ ID NO:2). Intron 1 of the RPS4 gene (SEQ ID NO:25) was inserted immediately after nucleotide 67 of SEQ ID NO:2; intron 2 of the RPS4 gene (SEQ ID NO:26) was inserted immediately after nucleotide 168 of SEQ ID NO:2; intron 3 of the RPS4 gene (SEQ ID NO:27) was inserted immediately after nucleotide 208 of SEQ ID NO:2; intron 4 of the RPS4 gene (SEQ ID NO:28) was inserted immediately after nucleotide 260 of SEQ ID NO:2; and intron 5 of the RPS4 gene (SEQ ID NO:29) was inserted immediately after nucleotide 337 of SEQ ID NO:2. In addition, in generating the intronylated version of the codon-optimized BleR gene (SEQ ID NO:30), a single nucleotide change from "T" to "A" was introduced with respect to SEQ ID NO:2 at the nucleotide corresponding to nucleotide position 210 of SEQ ID NO:2.

Figure 5:
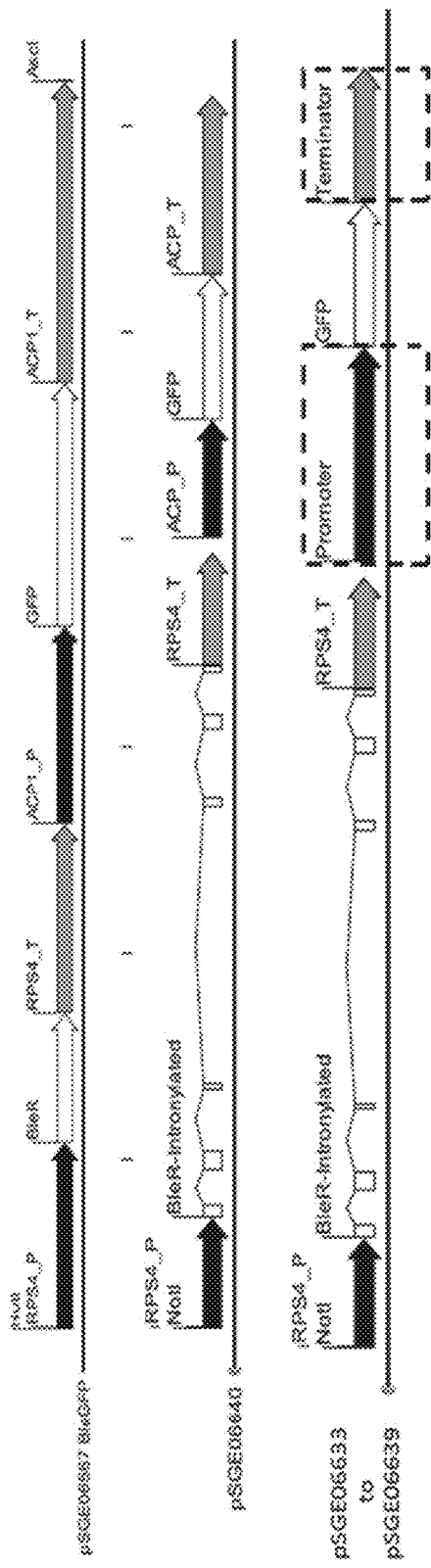
FIG. 5 provides diagrams of constructs, including control plasmid pSGE6567 (upper diagram) where the ACP1 promoter (SEQ ID NO:8) and ACP1 terminator (SEQ ID NO:9) elements are positioned to drive the expression of GFP, and are adjacent to the BleR selection marker which is operably linked to the RPS4 promoter (SEQ ID NO:1) and the RPS4 terminator (SEQ ID NO:7). pSGE6640 (middle) has the same organization as pSGE6567, except that the BleR selection marker is intronylated with the five introns (SEQ ID NOs:25-29) of the RPS4 gene as in pSGE6543 (FIG. 4). The bottom diagram is a generalized diagram for plasmids pSGE6633 to pSGE6639, in which the promoter and terminator regions flanking GFP (and surrounded by dashed boxes) vary (see Table 1). As described in Example 7, seven promoter/terminator combinations were tested in this construct that harbored the intronylated BleR selectable marker expression cassette derived from plasmid pSGE6543.

Construct pSGE6543 that included the intronylated version of the codon-optimized BleR gene (SEQ ID NO:30) demonstrated dramatically higher transformation efficiency with respect to construct pSG6530 that included the non-intronylated codon-optimized BleR gene (SEQ ID NO:2) (Table 5). This indicates that addition of multiple introns (that are heterologous with respect to the transgene) derived from a gene endogenous to the host organism to an open reading frame of an introduced gene (transgene) can increase the expression level of the transgene.

the impact of using an intron-free or intronylated version of the BleR open reading frame, the ACP1 control elements validated in plasmid pSGE6531 (Example 5, FIG. 3B) were also used to drive GFP expression on plasmids pSGE6567 and pSG06640, respectively (FIG. 5).

The results are summarized in Table 6. All seven promoters tested were functionally validated by their ability to drive GFP expression in transformed WT-1185 strains. Variation was observed with respect to the percent of strains exhibiting high and low level expression with complete GFP penetrance of all strains tested.

TABLE 6

Transformation results of constructs with GFP gene operably linked to seven additional promoter/terminator pairs.

| Plasmid ID | GFP Promoter/terminator abbreviation | Promoter Sequence ID in appendix | Terminator sequence ID in appendix | Annotated promoter/terminator source gene name | number of transgenic colonies with Complete GFP penetrance; High expression | number of transgenic colonies with Complete GFP penetrance; low expression |
|---|---|---|---|---|---|---|
| pSGE06633 | OCP-A | 11 | 12 | Organellar oligopeptidase A | 6/92 | 25/92 |
| pSGE06634 | 195188 FBP-C1 | 13 | 14 | FBPase | 23/92 | 13/92 |
| pSGE06635 | 191515 EF2 | 15 | 16 | Elongation factor 2 | 20/92 | 45/92 |
| pSGE06636 | 188580 30SRP-S17 | 17 | 18 | 30S Ribosomal protein S17 | 31/92 | 14/92 |
| pSGE06637 | 191264 mitoATPSD | 19 | 20 | Mitochondrial ATP synthase | 2/92 | 48/92 |
| pSGE06638 | 196997 RBCS1 | 21 | 22 | Rubisco Sma I subunit isoform 1 | 14/92 | 16/92 |
| pSGE06639 | 196998 RBCS2 | 23 | 24 | Rubisco Sma I subunit isoform 2 | 15/92 | 11/92 |
| pSGE06640 | 1185 ACP | 8 | 9 | Acyl Carrier protein | 22/92 | 43/92 |
| pSGE06567 | 1185ACP (Non-Intronylated) | 8 | 9 | Acyl-Carrier protein | 2/11 | 0/11 |

TABLE 5

No. of colonies from Transformation: Intron-free v. Intronylated BleR Constructs.

| DNA | Linearized Vector or Fragment | Zeocin resistant colonies observed |
|---|---|---|
| pSGE6530 | Fragment | 100 |
| pSGE6530 | Linearized | 70 |
| pSGE6543 | Linearized | 5376 |
| No DNA control | N/A | 0 |

Example 7. Construction and Testing of Additional Expression Cassettes

Figure 6A:
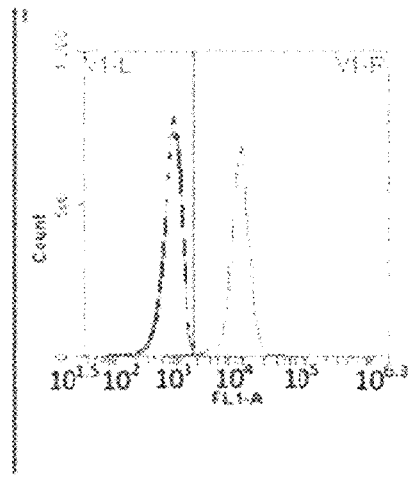
FIGS. 6A-6D shows exemplary flow cytometry data for GFP fluorescence histograms of transformed lines indicating A) High level GFP expression with complete penetrance; B) Low level GFP expression with complete penetrance; C) No GFP fluorescence above wildtype; and D) Partial penetrance of GFP expression. Dark traces are from untransformed WT-1185 cells (background fluorescence), which are overlayed with light traces from different transgenic GFP-expressing strains generated from the experiment described in Example 6.
Figure 6B:
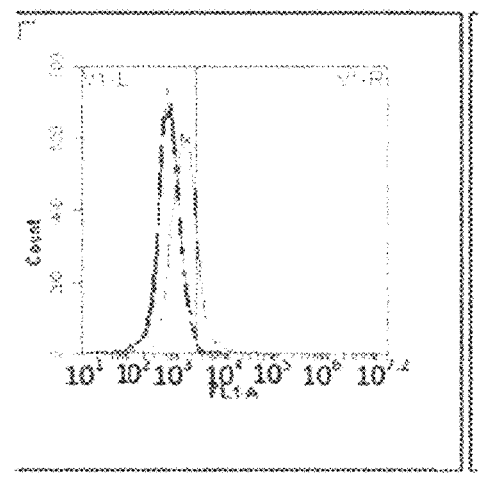
Figure 6C:
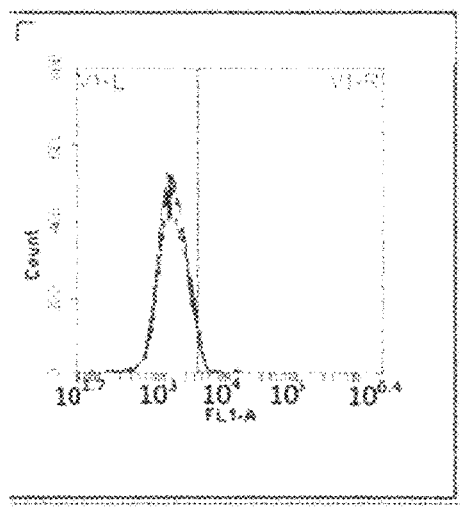
Figure 6D:
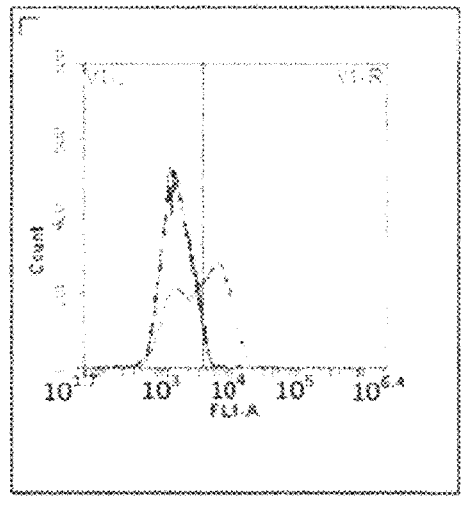

Additional potential promoter and terminator control elements were tested that could be used in constructs to drive the expression of transgenes of interest such as, for example, a reporter gene, RNAi constructs, RNA-guided endonucleases, regulators such as transcription factors, or genes involved in metabolic pathways related to lipid biosynthesis or photosynthetic efficiency. Seven promoter/terminator pairs (see Table 1) from endogenous genes were selected based on covering a wide range of gene structures with respect to open reading frame size, intron number, and expression strength. Genes were only considered if the upstream and downstream genes were present on the same strand of DNA, and if deduced 5' and 3' untranslated regions were available from RNA-Seq cDNA assemblies. Promoter/terminator pairs for the seven genes were cloned into the same construct containing an intronylated, codon-optimized BleR (bleomycin/Zeocin resistance) cassette, where the promoters and terminators being tested were positioned to drive the expression of GFP (FIG. 5). As a control to account for High and low level expression of GFP were assessed by measuring GFP fluorescence on an Accuri Flow cytometer and separated into two categories, based on whether they were observed to demonstrate a high or low level of "fully penetrant" of gene expression as shown in FIG. 6A-D. FIG. 6A provides an overlay of a histogram of fluorescence of wild type cells (black curve) with the fluorescence histogram of transformed cells (gray curve), where the transformed cells give rise to a single peak that is shifted to the right (higher fluorescence) with respect to the wild type cells. This transformant line—demonstrating in flow cytometry a single peak shifted to the right relative to the fluorescence peak of control cells—is said to gray curve shifted to the right with respect to the black wild type curve) and wild-type cells in which the peak is closer to that of the wild type cells but nonetheless is a single peak, shifted to the right (higher fluorescence) with respect to the background fluorescence of wild type cells. The transformant line whose flow cytometry fluorescence profile is shown in FIG. 6A is classified here as having "high" fully penetrant expression of GFP, whereas the transformant line whose flow cytometry fluorescence profile is shown in FIG. 6B is classified here as having "low" fully penetrant expression of GFP. The majority of the transformants tested showed no GFP fluorescence above wild type background (see FIG. 6C as an example), with the exception of two strains which exhibited partial GFP penetrance (see FIG. 6D as an example of partial penetrance, where the transformed cell line exhibits more than one peak, one of which is coincident with the wild type background fluorescence peak). (Methods of isolating fully penetrant cell lines are also disclosed in U.S. Ser. No. 14/986,492, filed Dec. 31, 2015 and corresponding PCT application published as WO 2016/109840, incorporated by reference herein.)

The data provided in Table 6 shows that all of the promoter/terminator pairs tested, OCP-A, FBPasem EF2, 30SRP-S17, mitoATPSD, RBCS1, RBCS2, and ACP, effected fully penetrant expression of the GFP gene to which they were operably linked, with some promoter/terminator pairs more frequently resulting in high levels of GFP expression in transformed lines and other promoter/terminator pairs more frequently resulting in low levels of GFP expression in transformed lines.

Plasmids pSG6633 to pSG6640 also included a unique cloning site, a sequence recognized by PmeI (SEQ ID NO:31), between the BleR and GFP expression cassettes. This site allows for convenient insertion of a transgene to generate an expression cassette for any gene of interest driven by any of the validated promoter/terminator elements described in Table 1 and Table 7.

Example 8. Intronylated Blasticidin Resistance Gene

An intronylated version of the blasticidin resistance gene (BsdR, SEQ ID NO:32) was also synthesized and used to generate a vector similar to pSGE6640, with the exception that the selectable marker is the BsdR intronylated gene (SEQ ID NO:33) rather than the BleR-intronylated gene. In this construct, in which the BsdR transgene includes five introns of a single Parachlorella gene, intron 1 of the Parachlorella RPS4 gene (SEQ ID NO:25) was inserted immediately after nucleotide 93 of SEQ ID NO:32; intron 2 of the Parachlorella RPS4 gene (SEQ ID NO:26) was inserted immediately after nucleotide 135 of SEQ ID NO:32; intron 3 of the Parachlorella RPS4 gene (SEQ ID NO:27) was inserted immediately after nucleotide 187 of SEQ ID NO:32; intron 4 of the Parachlorella RPS4 gene (SEQ ID NO:28) was inserted immediately after nucleotide 238 of SEQ ID NO:32; and intron 5 of the Parachlorella RPS4 gene (SEQ ID NO:29) was inserted immediately after nucleotide 315 of SEQ ID NO:32.

Figure 7:
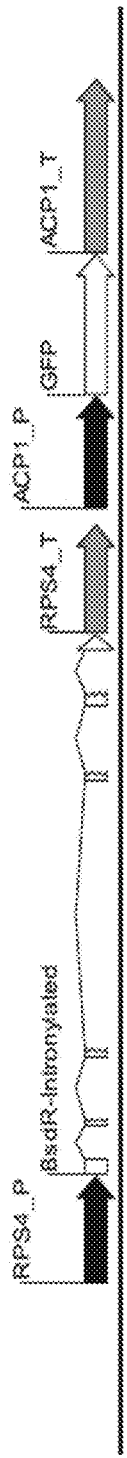
FIG. 7 is a diagram of a construct that includes an intronylated version of the blaticidin resistance gene (BsdR; SEQ ID NO:26). This construct was used successfully in transformations (Example 8).

The resulting vector, pSGE6676, is shown schematically in FIG. 7. This construct was also functionally validated as demonstrated in Examples 7 and 8 for the intronylated BleR construct, and was observed to give rise to blasticidin resistant colonies that express GFP.

Example 9. Intronylated Nourseothricin Resistance Gene

Figure 8A:
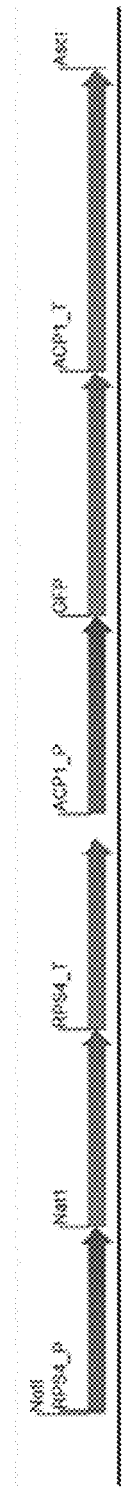
FIGS. 8A-8B provides diagrams of constructs that include A) non-intronylated and B) intronylated engineered nourseothricin resistance genes (nail).
Figure 8B:
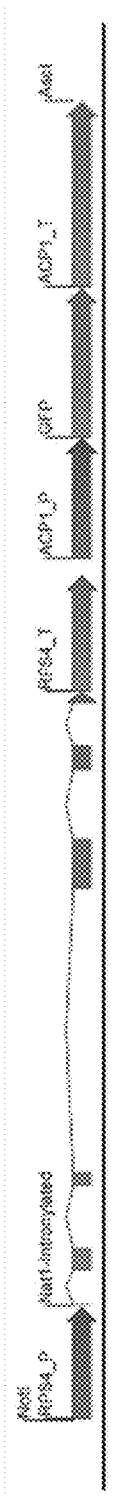

A gene for nourseothricin acetyltransferase (nat1) from Streptomyces noursei was codon optimized for Parachlorella (SEQ ID NO:50) and intronylated with the same five introns of the Parachlorella RPS4 gene as were used in Example 8, above, for intronylation of the BsdR gene. The resulting intronylated nat1 gene (SEQ ID NO:51) was cloned in a vector flanked by the RSP4 promoter at the 5' end of the nat1 gene and the RPP4 terminator at the 3' end of the nat1 gene as shown in FIG. 8B. The construct linearized with PvuI and, separately, the intronylated nat1 gene expression cassette (promoter—intronylated nat1 gene—terminator) as an isolated Asc/Not fragment were transformed into Parachlorella WT-1185 cells by particle bombardment as disclosed in Example 3. Tranformants were selected on plates that included 300 mg/mL nourseothricin.

The non-intronylated, codon-optimized nat1 gene (SEQ ID NO:50) was also cloned in the same vector, also flanked by the RSP4 promoter at the 5' end of the nat1 gene and the RPP4 terminator at the 3' end of the nat1 gene (FIG. 8A) and transformed into Parachlorella WT-1185 cells by particle bombardment. In this case the construct, linearized with PvuI, and, separately, the promoter—Nat1 gene—terminator cassette (as an isolated Asc/Not fragment) were transformed into Parachlorella WT-1185 cells as disclosed in Example 3, and tranformants were selected on plates that included 300 mg/mL nourseothricin.

Even accounting for the fact that twice as many cells were plated from the transformations with the intronylated nat1 gene that included five introns from the same Parachlorella gene (RPS4) than were plated from the transformations with the non-intronylated version of the nat1 gene, proportionately more colonies (and more PCR-verified transformants) resulted from transformation with the intronylated nat1 gene. For the linearized construct, for example, 8 transformants (of 34 colonies resulting from $10^9$ plated cells) were positive for the transgene that was intronylated, versus only one transformant (of twelve colonies from $5 \times 10^8$ plated cells) that was positive for the non-intronylated tansgene (Table 8).

TABLE 7

Number of colonies from Transformation with Intron-free and Intronylated BleR Constructs.

|  | Nat1 - No Introns | | Nat1 - 5 Introns | |
| --- | --- | --- | --- | --- |
|  | Asc/Not Fragment | Linearized Construct (PvuI) | Asc/Not Fragment | Linearized Construct (PvuI) |
| # cells plated | $5 \times 10^8$ | $5 \times 10^8$ | $1 \times 10^9$ | $1 \times 10^9$ |
| Colonies | 9 | 12 | 6 | 34 |
| PCR+ | 0 | 1 | 1 | 8 |

Example 10. Transformation Via Electroporation

Transformation of WT-1185 was also achieved by electroporation using a procedure as describe herein. To prepare culture for transformation, a 100 mL seed culture inoculated to $1 \times 10^6$ cells/mL six days before transformation was used to inoculate a 1 L culture to $1 \times 10^6$ cells/mL two days before transformation. On the day of transformation, cells were pelleted by centrifugation at 5000×g for 20 minutes, washed three times with 0.1 µm filtered 385 mM sorbitol, and resuspended to $5 \times 10^9$ cells/mL in 385 mM sorbitol.

Electroporation of 100 µL concentrated cells was performed in 0.2 cm cuvettes in a BioRad Gene Pulser Xcell™ under varied conditions. The DNA used for optimization of electroporation was linearized pSG6640 including ble and TurboGFP expression cassettes. The ble cassette included the RPS4 promoter operably linked to the ble gene (SEQ ID NO:2) and the RPS4 terminator. The TurboGFP cassette included the ACP promoter operably linked to the TurboGFP gene (SEQ ID NO:5) and the ACP terminator Immediately after electroporating pre-chilled cells and cuvettes, 1 mL cold sorbitol was added and used to transfer cells into 10 mL PM074. After overnight recovery, cells were concentrated and spread onto 13 cm-diameter PM074 media containing zeocin at 250 mg/L and grown under the conditions listed in the biolistics section.

Figure 9A:
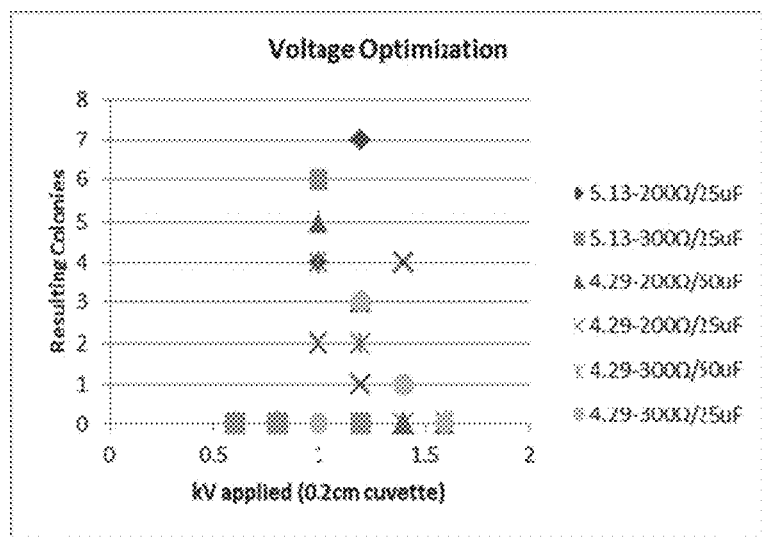
FIGS. 9A-9C shows data from the optimization of the WT-1185 electroporation protocol. A) Graph depicting colony number generated while determining the optimal voltage for electroporation of WT-1185. 1 ug pSGE06640 DNA was mixed with 5×10^8 cells in 100 uL 385 mM sorbitol. Indicated voltages were applied to 0.2 cm cuvettes with 200 or 300 ohm resistance and 25 or 50 uF capacitance as indicated. Data were generated from transformations on two separate days. Colonies were counted two weeks after transformation and selection. B) Graph depicting colony number generated while determining the optimal resistance and capacitance for transformation of WT1185 by electroporation. 1 ug pSGE06640 DNA was mixed with 5×10^8 cells in 100 uL 385 mM sorbitol and electroporated at 1 kV applied to a 0.2 cm cuvette under the indicated resistances and capacitances. Colonies were counted two weeks after transformation and selection. C) Graph depicting colony number generated while determining the optimum quantity of pSGE06640 DNA to electroporate for transformation of WT1185. Varying amounts of DNA were mixed with 5×10^8 cells in 385 mM sorbitol in 0.2 cm cuvettes and electroporated at 1 kV 200 ohms 25 uF. Colonies were counted two weeks after transformation and selection.
Figure 9B:
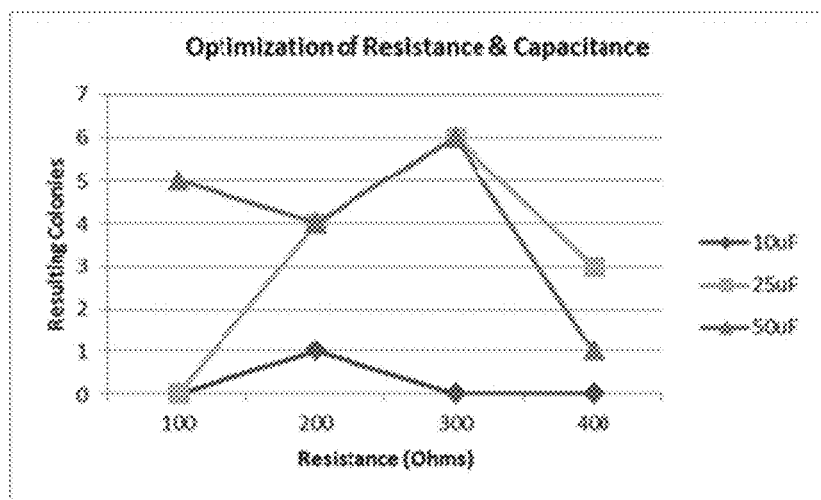
Figure 9C:
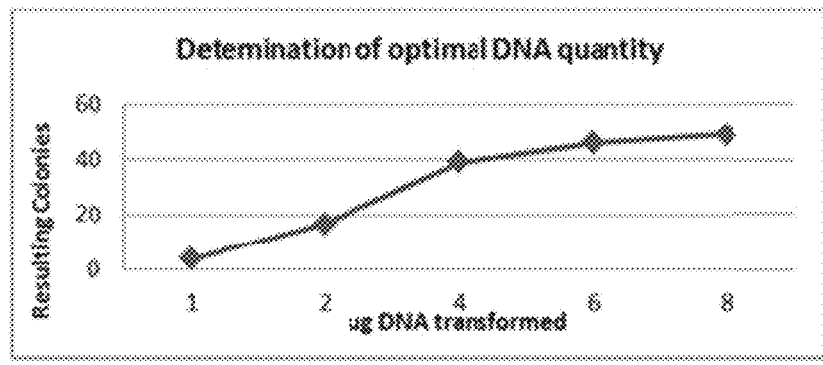

After testing a range of voltages, resistances, and capacitances as detailed in FIGS. 9A-C and counting the colonies present two weeks after transformation, the optimal electroporation conditions were determined to be 1.0-1.2 kV (5000-6000 V/cm), 200-300 ohms, and 25-50 µF. Use of larger quantities of DNA increased the resulting number of zeocin-resistant colonies, though the effect plateaued at amounts larger than 4 μg.

Example 11. Generation of Cas9 Expression Cassette

Figure 10:
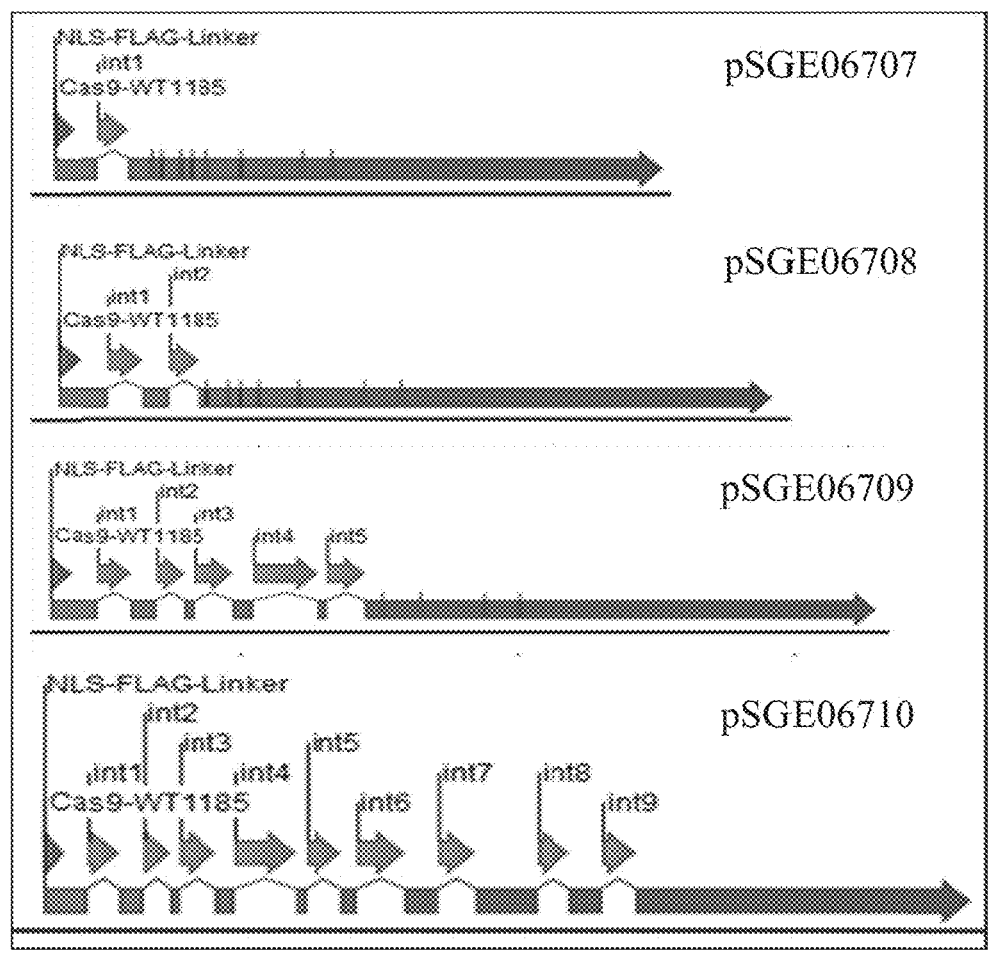
FIG. 10 provides diagrams of four constructs for expression of a codon-optimized, intronylated Cas9 gene. The first construct, pSGE6707, included one FBPase intron, the second construct, pSGE6708, included two FBPase introns, the third construct, pSGE6709, included five FBPase introns, and the fourth construct, pSGE6710, included nine FBPase introns. Introns are shown as arrows.

The Cas9 gene of *Streptococcus pyogenes* with an N-terminal nuclear localization sequence (NLS) and C terminal FLAG tag was codon-optimized for expression in *Parachlorella* and four different constructs were designed, each of which had a different number of introns of the FBPase gene inserted into the codon-optmized Cas9 gene. The intronylated Cas9 genes in each case were operably linked to the *Parachlorella* RPS17 promoter (SEQ ID NO:17) at the 5' end of the gene and the RPS17 terminator (SEQ ID NO:18) at the 3' end of the gene. The constructs included the codon-optimized Cas9 gene with the first 1, 2, 5, or 9 introns from the endogenous *Parachlorella* FBPase gene (FIG. 10). The first intron was inserted 330 base pairs into the coding sequence. These plasmids were transformed into WE-1185.

TABLE 8

Introns of the *Parachlorella* FBPase gene.

| Intron number | SEQ ID NO | Size of Intron (bp) |
|---|---|---|
| 1 | 35 | 221 |
| 2 | 36 | 184 |
| 3 | 37 | 266 |
| 4 | 38 | 429 |
| 5 | 39 | 256 |
| 6 | 40 | 338 |
| 7 | 41 | 259 |
| 8 | 42 | 232 |
| 9 | 43 | 237 |

The plasmids, pSGE6707, pSGE6708, pSGE6709, and pSGE6710, also included the TurboGFP gene (Evrogen, Moscow, Russia) codon-optimized for *Parachlorella* (SEQ ID NO:5) driven by the ACP promoter (SEQ ID NO:8) and terminated by the ACP terminator (SEQ ID NO:9).

TABLE 9

Constructs with Intronylated Cas9 gene.

| Construct | Number of FBPase introns | SEQ ID NOs of inserted introns |
|---|---|---|
| pSGE06707 | 1 | SEQ ID NO: 35 |
| pSGE06708 | 2 | SEQ ID NOs: 35 & 36 |
| pSGE06709 | 5 | SEQ ID NOs: 35, 36, 37, 38, and 39 |
| pSGE06710 | 9 | SEQ ID NOs: 35, 36, 37, 38, 39, 40, 41, 42, & 43 |

Figure 11:
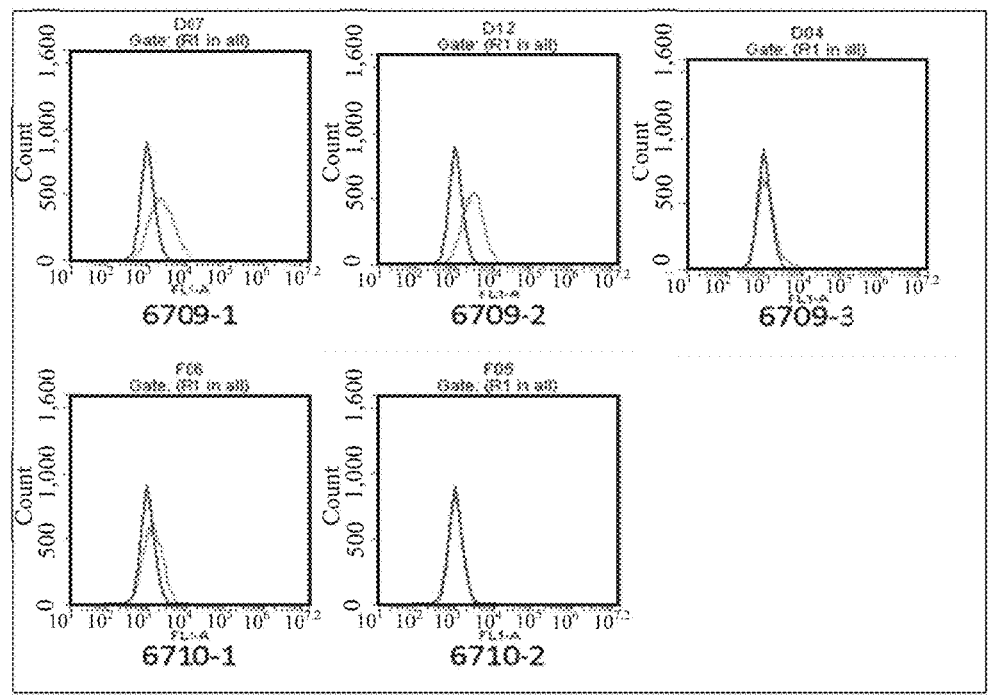
FIG. 11 Flow cytometry histograms show GFP fluorescence of putative transformants for Cas9 expression. 6709-1 and 6709-2 were the only two fully penetrant lines with strong GFP shifts. The black peaks represent the wild type strain WE-1185 background level of fluorescence; the gray peaks correspond to respective transformants.
Figure 12:
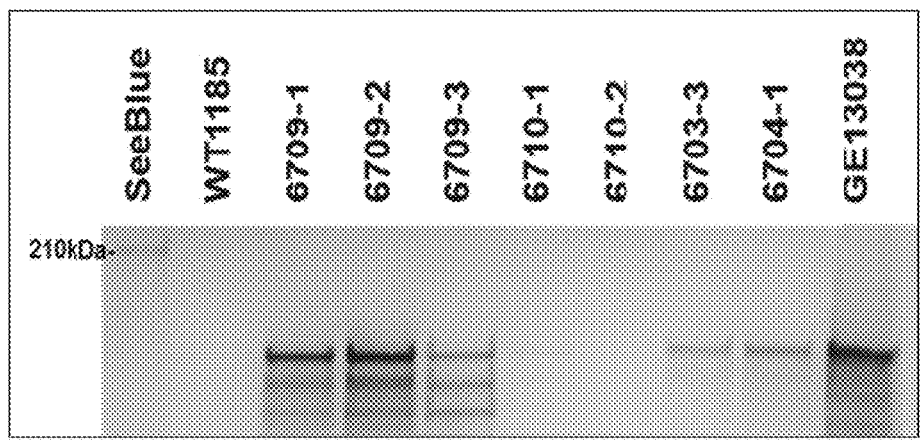
FIG. 12 Anti-Cas9 Western Blot analysis of transformants. 6709-1 and 6709-2 had strong Cas9 expression; the band intensities are about 50% of the expression level observed in our *Nannochloropsis* Cas9 control strain GE-13038. Strain 6709-2 was given strain name GE-15699.

*Parachlorella* cells were transformed by electroporation and transformant colonies arising from transformation with all four constructs were expanded and tested by flow cytometry for penetrance. Two fully penetrant transformants with strong GFP shifts were obtained from pSGE6709 (five intron construct) transformations; three other transformants using other constructs had weak GFP expression, while all others showed no GFP fluorescence shifts at all (examples shown in FIG. 11). All five transformed lines with GFP expression were carried forward for anti-Cas9 Western Blot analysis. The two fully penetrant lines, 6709-1 and 6709-2, had good Cas9 expression; the Western Blot band intensities are approximately 50% of the expression level observed in *Nannochloropsis* Cas9 control strain GE-13038 (FIG. 12). Strain 6709-2 was given a new strain ID, GE-15699, and carried forward to test for Cas9 functionality.

Figure 13:
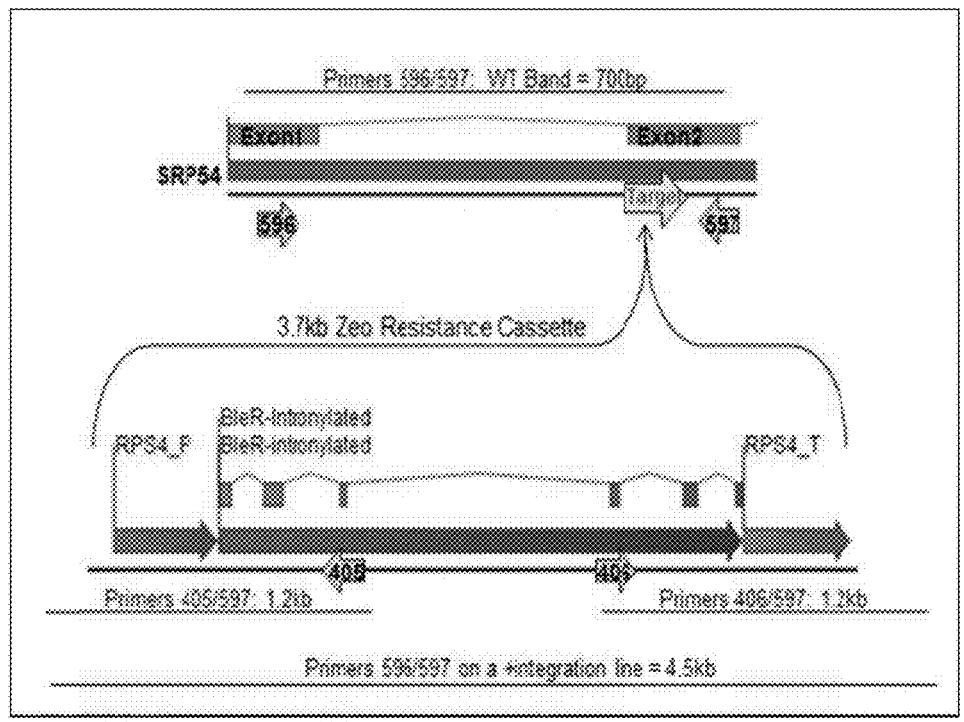
FIG. 13 Overview of the colony PCR screening approach to detect insertion of the BleR cassette into the SRP54 locus.
Figure 14:
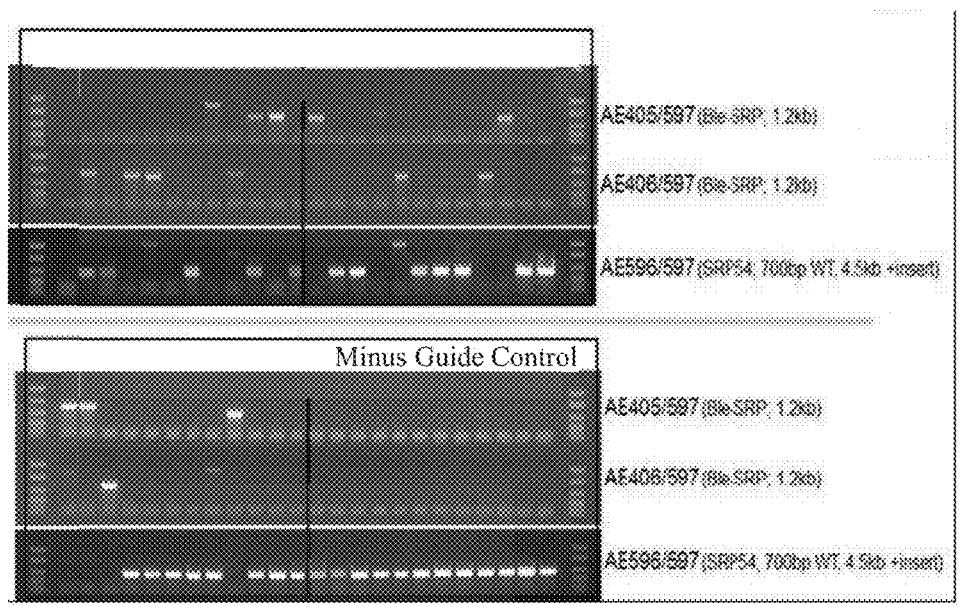
FIG. 14 Colony PCR results. Transformants were screened using primers designed to amplify across the native targeted locus (AE596/AE597), which will produce a 700 bp band if there is no integration or "knock-in" of the BleR cassette at the targeted locus, or a 4.3 kb band if there is knock-in of a single BleR cassette. Colony PCR was also done using primers designed to amplify from the SRP54 gene (AE597), into our selectable marker (AE405/AE406). Depending on orientation of the integrated BleR cassette, a 1.2 kb band will result from either amplification by primers 405/597 or 406/597 spanning from within the BleR cassette out to the SRP54 gene. The minus gRNA control gel shows amplification of the native locus but no integration PCR products.

To test strain GE-15699 for genome editing capability, the *Parachlorella* chloroplastic SRP54 gene was targeted for knockout (cpSRP54, protein-encoding sequence provided as SEQ ID NO:10). *Parachlorella* mutants created by classical mutagenesis with mutations in this gene had a pale green phenotype. Since mutation of this target leads to viable transgenic lines with a phenotype that is easily observable by eye, SRP54 was selected as a target for testing Cas9 editing capability in *Parachlorella*. A zeocin resistance selection cassette (containing a bleomycin resistance "BleR" gene codon-optimized for *Parachlorella* that included introns from *Parachlorella* (SEQ ID NO:30) operably linked to the *Parachlorella* RPS4 promoter (SEQ ID NO:1) and terminated by the *Parachlorella* RPS4 terminator (SEQ ID NO:7) was co-transformed into GE-15699 as a donor or editing DNA for insertion into the target site with a guide RNAs (gRNA) targeting SRP54 (target sequence, including PAM, provided as SEQ ID NO:45) by electroporation as disclosed herein, and the transformed cells were plated onto media containing zeocin. Pale colonies were observed for most of the gRNAs tested; transformants from a single gRNA were analyzed by colony PCR for the altered SRP54 locus. Colonies were screened using primers designed to amplify across the native targeted locus (AE596 (SEQ ID NO:46)/AE597 (SEQ ID NO:47)), designed to produce a 700 bp band if no integration into the target site occurred or a 4.3 kb band if a single BleR cassette was integrated into the target locus. For more complete and thorough analysis, colony PCR was also done using primers designed to amplify from the SRP54 gene (AE597; SEQ ID NO47:) into the BleR selectable marker (either primer AE405 (SEQ ID NO:48) or primer AE406 (SEQ ID NO:49). Depending on the orientation of the integrated BleR cassette, the primers were designed to produce a 1.2 kb band from amplification by either primer pair 405/597 or primer pair 406/597 spanning from within the BleR cassette out to the SRP54 gene (FIG. 13). The results show knock-in of the BleR cassette into the targeted locus (FIG. 14) occurred at a high frequency of at least 40% of transformed (ZeoR) colonies (demonstrating a 1.2 kb band generated by either primer set 405/597 or primer pair 406/597). Sequence analysis of the PCR products confirmed disruption of SRP54 with the BleR cassette. Additional transformants that resulted in pale colonies but did not demonstrate insertion of the BleR cassette in the PCR screen were in many cases found to have indels at the targeted site of the SRP54 gene, indicating the Cas9 enzyme had been active in these transformants as well.

Although the disclosure has been described with reference to the above examples, it will be understood that modifications and variations are encompassed within the spirit and scope of the disclosure. Accordingly, the disclosure is limited only by the following claims.

What is claimed is:

1. An isolated DNA molecule comprising a promoter that comprises a nucleotide sequence having at least 80% identity to at least 100 contiguous nucleotides of a sequence selected from the group consisting of SEQ ID NO:1, SEQ ID NO:4, SEQ ID NO:8, SEQ ID NO:11, SEQ ID NO:13, SEQ ID NO:15, SEQ ID NO:17, SEQ ID NO:19, SEQ ID NO:21, and SEQ ID NO:23 operably linked to a heterologous sequence encoding a polypeptide or functional RNA.

2. The isolated DNA molecule of claim 1, comprising a terminator.

3. The isolated DNA molecule of claim 2, wherein the terminator is derived from the same species as the promoter.

4. The isolated DNA molecule of claim 3 wherein the terminator comprises a sequence having at least 80% identity to at least 100 contiguous nucleotides of a sequence selected from the group consisting of SEQ ID NO:7, SEQ ID NO:9, SEQ ID NO:12, SEQ ID NO:14, SEQ ID NO:16, SEQ ID NO:18, SEQ ID NO:20, SEQ ID NO:22, and SEQ ID NO:24.

5. The isolated DNA molecule of claim 1, wherein the heterologous sequence encoding a polypeptide or functional RNA comprises at least one heterologous intron.

6. The isolated DNA molecule of claim 5, wherein the at least one heterologous intron is derived from the same species as the promoter.

7. The isolated DNA molecule of claim 5, comprising at least three heterologous introns.

8. The isolated DNA molecule of claim 7, comprising at least five heterologous introns.

9. The isolated DNA molecule of claim 7, wherein the at least three heterologous introns are derived from the same species as the promoter.

10. The isolated DNA molecule of claim 9, wherein the at least three heterologous introns are derived from the same gene.

11. The isolated DNA molecule of claim 10, wherein the at least three heterologous introns and the promoter are derived from the same gene.

12. The isolated DNA molecule of claim 1, wherein the heterologous sequence encodes a functional RNA selected from the group consisting of an antisense sequence, a micro RNA, a shRNA, an siRNA, a gRNA, and a ribozyme.

13. The isolated DNA molecule of claim 1, wherein the heterologous sequence encodes a polypeptide.

14. An expression cassette comprising the isolated DNA molecule of claim 13, wherein the heterologous sequence encodes a polypeptide selected from the group consisting of: (a) a protein associated with lipid biosynthesis, (b) a lipase, (c) a protein that participates in photosynthesis, (d) a protein associated with carbon fixation, (e) a transporter protein, (f) a dehydrogenase, (g) a transcription factor, (h) a transcriptional activator, (i) a cell signaling protein, (j) a metabolic enzyme, (k) a reporter protein, and (l) a selectable marker.

15. A method of transforming an algal cell, comprising introducing a vector comprising an expression cassette of claim 14 into an algal cell and selecting for a transformant.

16. The method of claim 15, wherein the expression vector is introduced by particle bombardment.

17. The method of claim 15, wherein the expression vector is introduced by electroporation.

18. The method of claim 17, wherein the algal cell is a Chlorophyte algal cell.

19. The method of claim 18, wherein the algal cell is of the Trebouxiophyceae class.

20. The method of claim 17, wherein the algal cell is of a genus selected from the group consisting of *Auxenochlorella, Chlorella, Heveochlorella, Marinichlorella, Parachlorella, Pseudochlorella*, and *Tetrachlorella*.

* * * * *